(12) United States Patent
Jung et al.

(10) Patent No.: US 12,174,164 B2
(45) Date of Patent: Dec. 24, 2024

(54) DEVICES, SYSTEMS, AND METHODS FOR DETECTING TARGETED COMPOUNDS

(71) Applicant: PURDUE RESEARCH FOUNDATION, West Lafayette, IN (US)

(72) Inventors: Byunghoo Jung, West Lafayette, IN (US); Babak Ziaie, West Lafayette, IN (US); Wuyang Yu, West Lafayette, IN (US); Weeseong Seo, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 780 days.

(21) Appl. No.: 16/085,523

(22) PCT Filed: Jan. 19, 2017

(86) PCT No.: PCT/US2017/014160
§ 371 (c)(1),
(2) Date: Sep. 14, 2018

(87) PCT Pub. No.: WO2017/160399
PCT Pub. Date: Sep. 21, 2017

(65) Prior Publication Data
US 2020/0088701 A1    Mar. 19, 2020

Related U.S. Application Data

(60) Provisional application No. 62/423,929, filed on Nov. 18, 2016, provisional application No. 62/308,848, filed on Mar. 15, 2016.

(51) Int. Cl.
*G01N 31/22* (2006.01)
*A61F 13/42* (2006.01)
*G01N 33/52* (2006.01)

(52) U.S. Cl.
CPC ........... *G01N 31/227* (2013.01); *A61F 13/42* (2013.01); *G01N 33/528* (2013.01); *A61F 2013/424* (2013.01)

(58) Field of Classification Search
CPC .... G01N 31/227; G01N 33/528; G01N 31/22; A61F 13/42; A61F 2013/424
See application file for complete search history.

(56) References Cited

U.S. PATENT DOCUMENTS 7,250,547 B1 * 7/2007 Hofmeister ............. A61F 13/42
340/573.5
2004/0220538 A1 * 11/2004 Panopoulos ............ A61F 13/42
604/361

(Continued)

FOREIGN PATENT DOCUMENTS

WO    2005111679 A1    11/2005
WO    2016028497 A1    2/2016

OTHER PUBLICATIONS

Seo et al (Diaper-embedded urinary tract infection monitoring system powered by a urine-powered battery, 2015 IEEE Biomedical Circuits and Systems Conference (BioCAS), Oct. 24, 2015 (Year: 2015).*

(Continued)

*Primary Examiner* — Paul S Hyun
*Assistant Examiner* — Jean C. Caraballo-Leon
(74) *Attorney, Agent, or Firm* — Reichel Stohry Dean LLP; Natalie J. Dean; Mark C. Reichel

(57) ABSTRACT

Systems, devices, kits, and methods for detecting and quantifying targeted compounds within a liquid (such as urine) are provided. Such systems, devices, and methods may be autonomous, noninvasive, and provide quick and accurate results. The systems and devices are at least partially disposable (single-use) and configured to be embedded within or applied to a conventional diaper or the like. Methods for (Continued)

using the systems and devices hereof include receiving a liquid to be tested within a portion of a disposable device, allowing the liquid to traverse through one or more channels defined within the device in a controlled fashion, reacting the liquid with one or more chemical reagents, using a sensing unit to collect photocurrent data regarding the chemical reach on(s), and wirelessly transmitting that data to a computing unit for storage and quantitative analysis.

20 Claims, 38 Drawing Sheets

(56) References Cited

U.S. PATENT DOCUMENTS

| | | |
|---|---|---|
| 2006/0092030 A1 | 5/2006 | Povenmire |
| 2008/0266117 A1 | 10/2008 | Song et al. |
| 2010/0041161 A1 | 2/2010 | Ferraeo De Paiva Martins et al. |
| 2014/0121487 A1* | 5/2014 | Faybishenko ..... A61F 13/15723 600/365 |
| 2015/0192512 A1 | 7/2015 | Srivastava |
| 2015/0194817 A1* | 7/2015 | Lee .......................... H02J 50/00 73/61.41 |

OTHER PUBLICATIONS

International Searching Authority, International Search Report, PCT Patent Application Serial No. PCT/US17/14160, dated May 25, 2017.

International Searching Authority, Written Opinion of the International Searching Authority, PCT Patent Application Serial No. PCT/US17/14160, dated May 25, 2017.

Seo, W. et al., Diaper-embedded Urinary Tract Infection Monitoring System Powered by a Urine-powered Battery, IEEE, 2015, pp. 1-4. URL: <http://ieeexplore.ieee.org/document/7348431/>.

Honrado, C. et al. A Capacitive Touch Screen Sensor for Detection of Urinary Tract Infections in Portable Biomedical Devices. Sensors, 2014, pp. 9-10. URL: <http://www.mdpi.com/1424-8220/14/8/13851>.

Yu, W. et al. Optical Nitrite Sensor and Urine-Activated Electrochemical Power Source on Paper Through Laser-Assisted Patterning and Lamination. 18th International Conference on Miniatureized Systems for Chemistry and Life Sciences, 2014, pp. 1-3. URL: <www.rsc.org/images/loc/2014/PDFs/Papers/755_0887.pdf>.

European Patent Office, Extended European Search Report for Application No. 17767102.1, Dec. 13, 2019, EU.

European Patent Office, Communication pursuant to Article 94(3) EPC for Application No. 17767102.1, Sep. 22, 2022, EU.

* cited by examiner

|  | Sensitivity* (95% confidence interval) | Specificity* (95% confidence interval) |
|---|---|---|
| Total dipstick urinalysis† | 94 (87–98) | 26 (21–31) |
| Blood | 86 (77–93) | 46 (40–51) |
| Leukocytes or nitrites | 82 (72–89) | 84 (80–88) |
| Leukocytes | 72 (62–82) | 86 (82–90) |
| Protein | 71 (61–81) | 53 (47–59) |
| Nitrite | 48 (37–59) | 96 (93–98) |

(a) Patterning  (b)  (c)

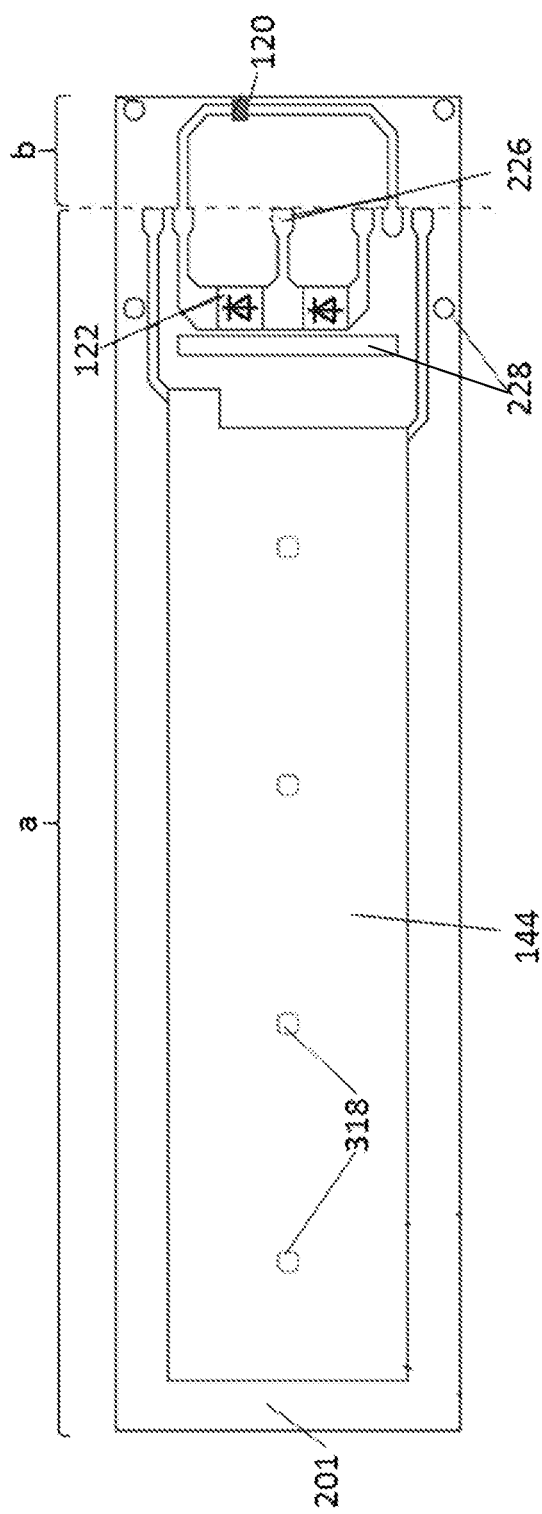
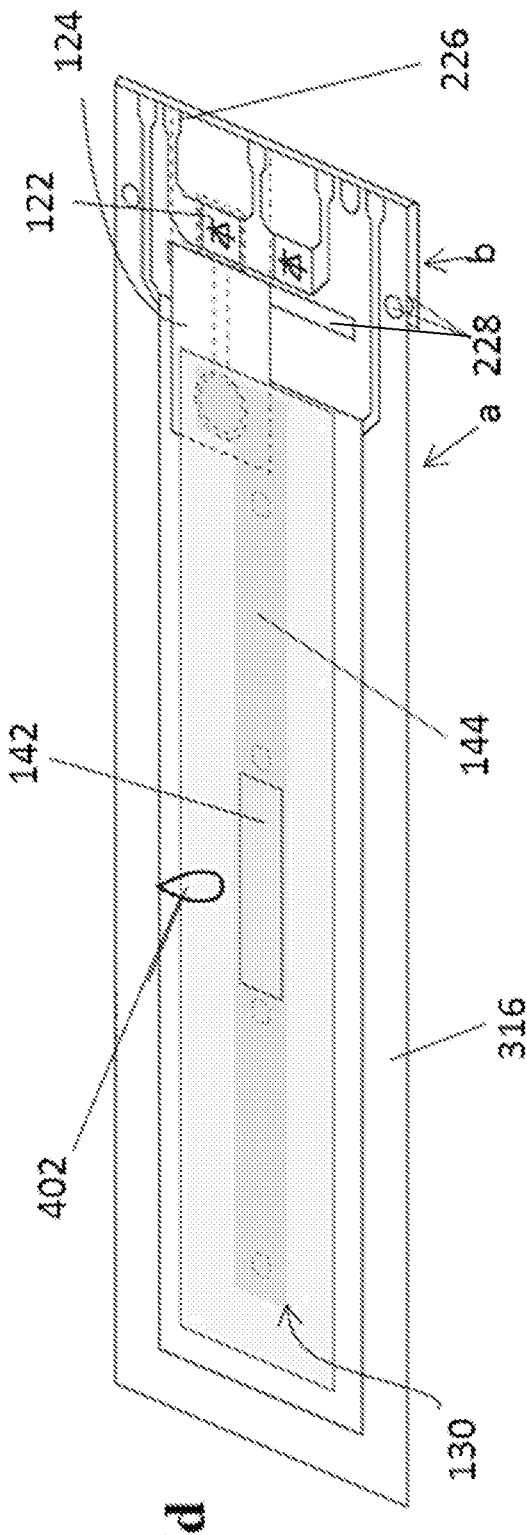
FIG. 5c
FIG. 5d

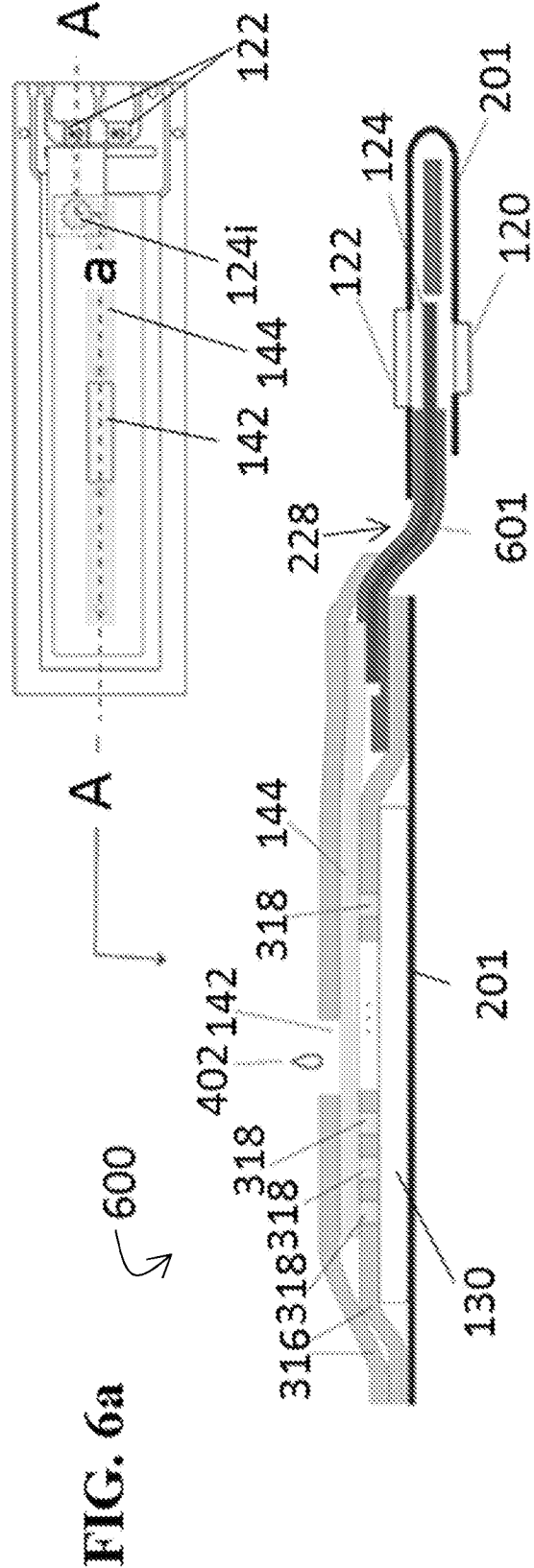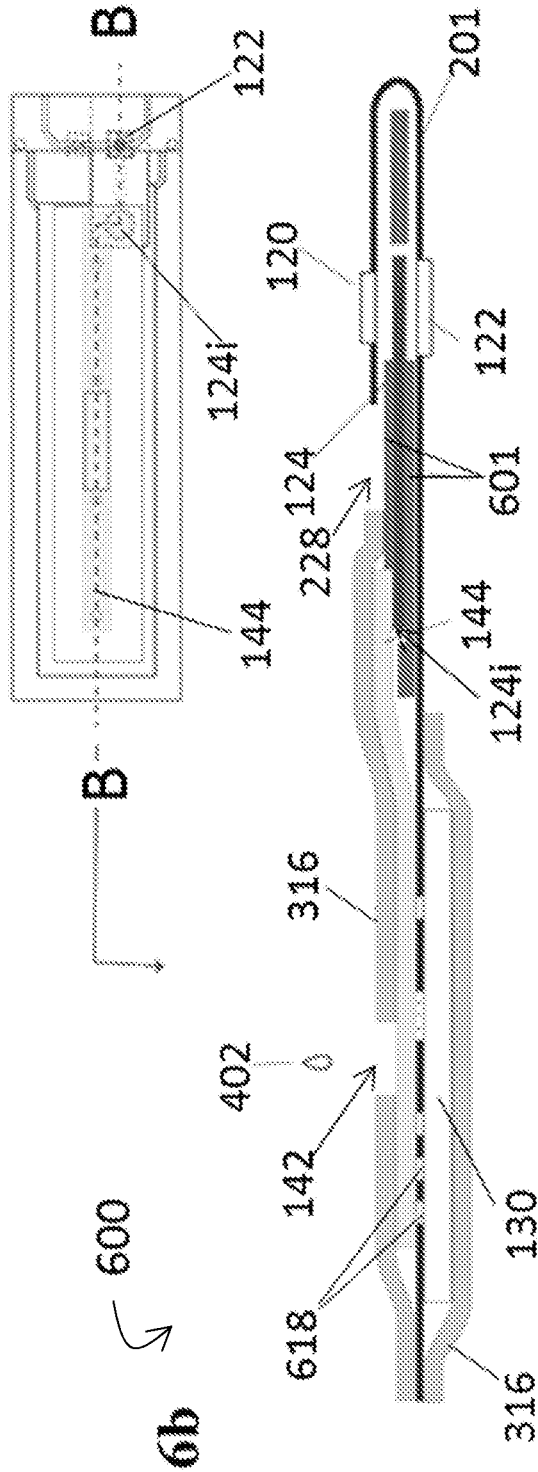
FIG. 6a
FIG. 6b

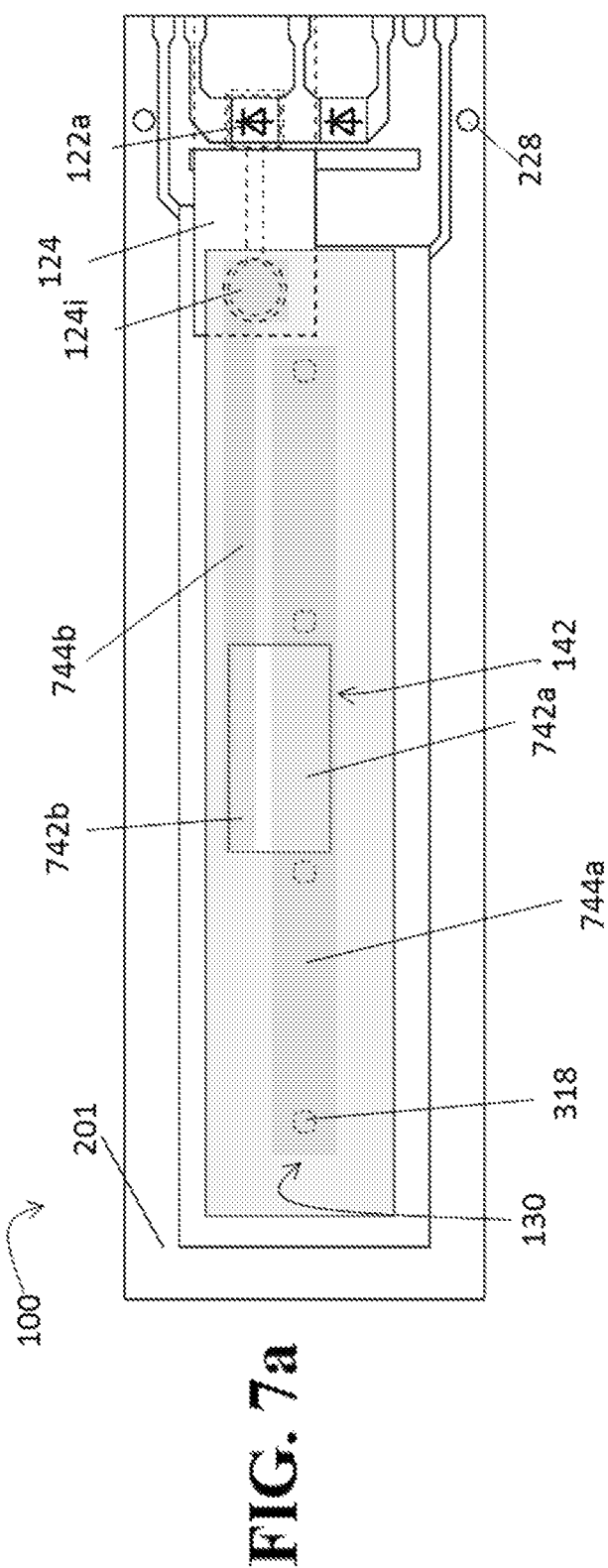
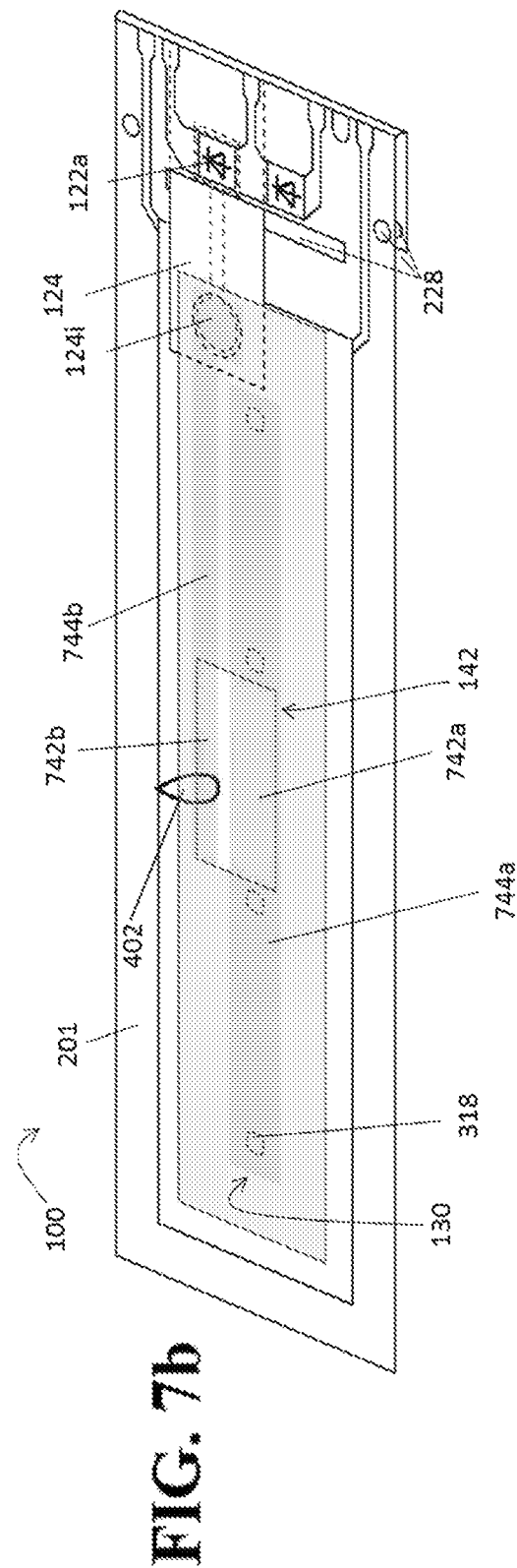

DEVICES, SYSTEMS, AND METHODS FOR DETECTING TARGETED COMPOUNDS

PRIORITY

The present application is related to, claims the priority benefit of, and is a 35 U.S.C. 371 national stage application of International Patent Application Serial No. PCT/US2017/014160 to Jung et al., filed Jan. 19, 2017, which is related to, and claims the priority benefit of: 1) U.S. Provisional Patent Application Ser. No. 62/308,848 to Jung et al. filed Mar. 15, 2016; and 2) U.S. Provisional Patent Application Ser. No. 62/423,929 to Jung et al. filed Nov. 18, 2016. The entire contents of each of the aforementioned priority applications are hereby expressly incorporated by reference in their entireties into this disclosure.

STATEMENT REGARDING FEDERALLY SPONSORED RESEARCH OR DEVELOPMENT

This invention was made with government support under Contract No. ECCS-1128169 awarded by the U.S. National Science Foundation. The United States Government has certain rights in the invention.

BACKGROUND

Urinary tract infection (UTI) is the second most common infection caused by bacterial pathogens, accounting for more than 8 million visits to health care providers and 100,000 hospitalizations in the United States annually. UTI is predominantly bacterial with coliform bacteria, with *Escherichia coli* (*E. coli*) in particular being responsible for most cases. It is also the most prevalent infection in the residents of long-term-care facilities with 15-50% of the cases being asymptomatic.

Generally, if identified and treated early, most UTIs are uncomplicated and easily treatable using antibiotics. However, if not found and left untreated, UTI can be a major source of serious complications such as ascending infections (e.g., pyelonephritis), loss of kidney function, bacteremia, and sepsis. Consequently, early identification and treatment of UTI is vital to prevent major sequelae or death.

Infants and geriatric patients suffering from neurodegenerative diseases such as dementia are especially vulnerable to the deleterious effects of undetected UTI. Both groups use diapers and have difficulties understanding and/or communicating their urinary discomfort and UTI associated symptoms (if not asymptomatic) to their care providers, which makes early stage identification of UTI quite challenging.

Traditionally, an accurate diagnosis of UTI is made with a urine culture test in a laboratory. This test allows for quantification of the bacterial growth, but takes 2 to 3 days between specimen collection and final diagnosis due to the time period required for cell cultivation. Furthermore, the urine culture test is not ideal for early detection of UTI. Primarily, the relatively high cost for a hospital visit (to collect the specimen) and the urine culture test itself is cost-prohibitive and, in most cases, prevents multiple and/or frequent urine culture tests from being performed. Second, a hospital visit for a urine culture test implies that the caregiver or patient already recognizes the symptoms of UTI, which often happens only after serious complications have surfaced, particularly for asymptomatic patients.

For these reasons, urine dipsticks have been widely used to detect UTI in early stages. A conventional urine UTI dipstick comprises a variety of chemical pads or reagents that react when immersed in, and then removed from, a urine sample. UTI dipsticks specifically detect the presence of nitrite, which is a surrogate of UTI. While urine dipsticks do allow for quick detection and are low-cost, this method is somewhat less accurate than conventional culture testing techniques with nitrite sensitivity falling within an 80-85% range. Moreover, collecting a urine specimen for the dipstick test from an infant or a disabled elderly is often painful, time-consuming, and privacy-sensitive. It becomes particularly challenging when multiple tests are required to filter out false alarms.

In light of this, several conventional UTI detection systems have been developed. Using the same chemical factors leveraged by a conventional UTI dipstick, one example of such a conventional approach includes printing a UTI dipstick on a commercial diaper using a hand-held printer to guarantee that a specific chemical factor is printed in a specific square area. When the reaction between the detection chemicals and urine occurs, a user (such as a caregiver) uses a camera of a smartphone to record the change in color(s), and process the images with a mobile application (using smartphone imaging analysis technology). Accordingly, although this approach eliminates the time required to collect individual urine samples, it does not offer a quantitative analysis and, more importantly, still requires a manual component to record the change in colors and process the images, thereby prohibiting completely autonomous operation. Additionally, this method also suffers from color fading and contamination issues that can significantly affect the methodology's ability to provide accurate results. Perhaps more specifically, unless a caregiver is immediately notified that the test subject has urinated, a time gap will occur between urination and the photo event. This time gap is often unpredictable and the color of the sensing part fades over time when it dries up. Another issue is the contamination by stool that may prohibit photo-based analysis.

Other conventional methods provide allow for measurement of mutual-capacitance to detect the presence of *E. coli* using a capacitance touch screen (CTS with surface-electrodes modified to have *E. coli* receptors. With CTS, errors often result from process variations such as capacitance variation in the CTS and the offset variation in the charge amplifier. Moreover, the CTS method is not autonomous because a caregiver places the urine sample on the CTS surface manually.

In light of the shortcomings of conventional methods, an alternative, more accurate method for early-stage identification of UTI is needed, as is a better screening method that can alert caregivers about UTI with minimal manual effort. Ideally, such methods should be autonomous, automatic, minimally invasive, and provide the patient with privacy, all while being easy to implement, affordable, and capable of providing accurate and timely results.

BRIEF SUMMARY

The present disclosure provides systems and methods relating to a novel detection system and related devices that allow for the early detection and noninvasive screening of UTI and other disorders. In at least one exemplary embodiment, a detection system hereof comprises a first disposable device for embedding or placement within a diaper, a second device for removable attachment to a diaper, the second device in wired communication with the first disposable device, and a computer readable program code executable to analyze the one or more output signals received from the second device (i.e. the data transmission unit thereof) and to calculate a concentration of a targeted compound in liquid received through a transport path of the first device based on the one or more output signals. In at least one embodiment, the liquid comprises urine or soil. Likewise, the targeted compound may comprise a nitrite or a nitrate, and the concentration of the targeted compound calculated may be used to detect a urinary tract infection.

Perhaps more specifically, in such embodiments, the first disposable device comprises: a sensing unit comprising a light source, a sensing strip comprising a reagent strip containing one or more colorimetric reagents for reacting with a targeted compound, and at least one sensor for measuring photocurrent data from the reagent strip; a power source unit in electrical communication with the sensing unit, the power source unit comprising at least one battery operable to power at least the sensing unit; and a transport path unit defining at least one open area configured for receiving liquid therethrough and comprising a transport path comprising a channel (microfluidic or otherwise) extending a length between the sensing unit and the power source unit. Furthermore, the second device comprises: a signal processing unit comprising a sensor interface circuit in operative communication with a microprocessor and configured to convert photocurrent data received from the sensing unit into one or more output signals; and a data transmission unit in operable communication with the signal processing unit. In at least one embodiment, the microprocessor of the signal processing unit is operable to execute the computer readable program code.

The first device may be disposable such that it can be thrown away or otherwise disposed of after the underlying diaper is soiled or otherwise used, while the second device can be removed from the discarded diaper and attached to and reused with a new (clean) diaper with a new first device embedded therein or attached thereto.

In certain embodiments of the detection system hereof, the transport path comprises parameters selected such that liquid received through the at least one open area and absorbed into the transport path travels along the length of the transport path to reach the at least one battery of the power source prior to reaching the reagent strip of the sensing unit. Additionally or alternatively, the transport path unit may further comprise a first transport path extending between the at least one open area and the sensing unit, and a second transport path extending between the at least one open area and the power source unit. In addition, the transport path unit may optionally comprise a pad positioned at or near the at least one open area. There, the pad comprises an absorbent material.

Additional embodiments of the detection system may further comprise a computing unit. The computing unit may comprise a processor operable to execute the computer readable program code. In at least one embodiment, the computer readable program code is accessible by or stored on computing unit and comprises: a computer readable program code means for receiving data from the data transmission unit of the second device, and a computer readable program code means for analyzing data received from the data transmission unit. Additionally or alternatively, the computing unit comprises a mobile device and the computer readable program code comprises a mobile application. The computer readable program code may be further executable to issue a notification if the concentration of the targeted compound is outside of a defined parameter.

Now referring to the sensors of the first disposable device, at least one of the at least one sensors may be configured to measure photocurrent data (e.g., at least one optic output signal) from the reagent strip when the reagent strip is dry, when the reagent strip is wet from absorbing a liquid, and after the one or more reagents of the reagent strip have reacted with the liquid. In such embodiments, the concentration of a targeted compound may be calculated using the difference between a first output signal corresponding with photocurrent data from the wet reagent strip and a second output signal corresponding with photocurrent data from the reagent strip that has reacted with the liquid. The targeted compound may be selected from a group consisting of nitrite, nitrate, protein, red blood cells, albumin, hemoglobin, white blood cells, and leucocyte esterase.

The light source of the sensing unit may comprise a light emitting diode or a laser. Additionally or alternatively, the at least one sensor may comprise an active photodetector or active photodiode. In certain embodiments, the system may further comprise a second photodetector. Still further, the at least one sensor of the sensing unit may comprise two photodetectors embedded within a flexible substrate and connected in series.

Again referring to the first disposable device, the reagent strip thereof may be aligned with and laterally offset from both the at least one sensor and the light source. Additionally, the at least one sensor may be positioned as to receive light emanating from the light source through the reagent strip. In at least one exemplary embodiment, the sensing unit of the detection system is positioned on a flexible substrate such that, when the substrate is folded, the reagent strip is positioned between the at least one sensor and the light source. The reagent strip may comprise a reagent impregnated matrix. Additionally or alternatively, the sensing strip may be packaged by at least one hydrophobic seal (such as, for example, a hermetic seal).

The power source unit of the detection system may comprise at least one liquid-activated battery such that when liquid is received within the at least one liquid-activated battery, the liquid-activated battery generates power and the sensing unit measures photocurrent data from the reagent strip. For example, the liquid-activated battery may comprise a urine-activated battery. Certain embodiments comprise at least two liquid-activated batteries connected in parallel or series. The at least one battery of the power source may be positioned within or separate and apart from the first disposable device (e.g., external to the diaper). Additionally or alternatively, the power source unit may further comprise a power stage for regulating voltage produced by the at least one battery. Still further, the second device may optionally comprise a power monitoring unit.

The detection system may further comprise a barrier positioned around at least part of the power source unit. The barrier may be a flexible, hydrophobic substrate, for example. In at least one embodiment, the barrier defines at least one opening through which liquid can pass into an interior of the first disposable device and contact the at least one battery. The at least one open area of the path transport unit may be substantially centered over the at least one opening defined in the barrier.

Now referring to the second device of the detection system, the sensor interface circuit of the signal processing unit may be selected from a group consisting of a pulse width modulation adjustable circuit and a transimpedance amplifier. Additionally or alternatively, the data transmission unit of the detection system may employ Bluetooth technology.

Yet additional embodiments of the second device further comprise a power control unit operatively coupled with one or more of the sensing unit, the sensor signal processing unit, and the data transmission unit. There, the power control unit is configured to periodically initiate an operative sleep mode comprising a temporary reduction or cessation of power to the units with which the power control unit is coupled to disable functionality thereof. Additionally, the power control unit may be further configured to periodically restore power to the one or more units with which the power control unit is coupled and activate the functionality thereof.

Methods for measuring a concentration of a targeted compound within a bodily fluid are also provided. In at least one embodiment, such a method comprises the steps of: receiving a liquid from a patient within at least one open area of a transport path unit and allowing the liquid to absorb into and flow along a transport path of the transport path unit; activating at least one battery with the liquid to supply power to a sensing unit comprising at least one light source, at least one reagent strip containing one or more colorimetric reagents for reacting with a targeted compound, and at least one sensor for measuring photocurrent data from the at least one reagent strip; measuring dry photocurrent data from the at least one reagent strip using the at least one sensor; wetting the at least one reagent strip with the liquid through flow of the liquid through the transport path and the sensing unit; measuring initial photocurrent data from the at least one wet reagent strip using the at least one sensor; measuring after-reaction photocurrent data from the at least one wet reagent strip using the at least one sensor; converting the dry photocurrent data, the initial wet photocurrent data, and the after-reaction photocurrent data into a dry output signal, a wet output signal, and an after-reaction output signal; and executing a computer readable program code, using a processor, to analyze the output signals and to calculate a concentration of a targeted compound in the liquid based on the output signals. There, the step of activating at least one battery with the liquid occurs before the step of measuring dry photocurrent data due to the flow of the fluid through the transport path.

Additionally, the computer readable program code may be executed by a microprocessor of the signal processing unit. In such embodiments, the method may further comprise the steps of: transmitting, using the data transmission unit, the calculated concentration of the targeted compound to a computing unit for storage and/or display; and comparing the calculated concentration with a predefined standard associated with a health condition. In such cases, the calculated concentration that falls outside of the predefined standard is indicative of the patient experiencing the health condition.

The methods hereof may further comprise the step of transmitting, using a data transmission unit, the output signals to a computing unit. In such cases, the step of executing a computer readable program code may be performed by a processor of the computing unit. Additionally or alternatively, the step of activating at least one battery with the liquid may occur before the step of measuring dry photocurrent data due to one or more parameters of the transport path. Such parameter(s) may be selected such that liquid received through the at least one open area and absorbed into the transport path reaches the at least one battery prior to reaching the reagent strip of the sensing unit.

Additional detection system embodiments are also provided, for example (but in no way limiting), for use in connection with a targeted compound selected from a group consisting of nitrite, nitrate, protein, hemoglobin, white blood cells, and leucocyte esterase. Additionally or alternatively, the subject liquid being assessed by the system may comprise urine or soil deposited within a diaper in which at least a portion of the detection system is embedded or attached. In such cases, the targeted compound may comprise a nitrite or a nitrate for example, and the concentration of the targeted compound calculated may be used to detect a urinary tract infection.

In at least one such exemplary embodiment, the detection system comprises a first disposable device for embedding or placement within a diaper, the first disposable device comprising: a sensing unit comprising a light source, a sensing strip comprising a reagent strip containing one or more colorimetric reagents for reacting with a targeted compound and an open area where the sensing strip may receive liquid, and at least one sensor for measuring photocurrent data from the reagent strip; and a transport path unit defining at least one open area configured for receiving liquid therethrough and comprising a transport path comprising a channel extending at least between the at least one open area and the sensing unit. In addition to the first disposable device, the detection system additionally comprises a second device for removable attachment to a diaper. There, the second device is in wired communication with the first disposable device and comprises: a signal processing unit comprising a sensor interface circuit in operative communication with a microprocessor and configured to convert photocurrent data received from the sensing unit into one or more output signals, and a data transmission unit in operable communication with the signal processing unit.

In addition to the first and second devices, the detection system additionally comprises a power source unit in electrical communication with the first and second devices, a power control unit communicatively coupled with one or more of the sensing unit, the sensor signal processing unit, and the data transmission unit, and a computer readable program code executable to analyze the one or more output signals received from the data transmission unit and to calculate a concentration of a targeted compound in liquid received through the transport path based on the one or more output signals. In such embodiments, the power source unit may comprise a power source for providing power to the sensing unit and a power stage for regulating voltage produced by the power source. Additionally, the power control unit may be configured to initiate one or more sleep mode events, with each sleep mode event comprising a reduction or cessation of power to the units with which the power control unit is communicatively coupled to disable functionality thereof. There, when the sensing unit receives power from the power source, the at least one sensor measures photocurrent data from the reagent strip.

The power control unit may further be configured to conclude a sleep mode event by restoring power to the one or more units with which the power control unit is communicatively coupled. In such cases, the conclusion of the sleep mode event activates the functionality to the one or more units to which power is restored. In at least one embodiment, if the sensing unit measures photocurrent data from the reagent strip when the reagent strip is dry, the power control unit is configured to initiate and cycle through one or more sleep mode events. In such cases, the conclusion of each sleep mode event may allow for at least the measurement of photocurrent data by the at least one sensor and/or activation of the data transmission unit.

In at least one embodiment of the detection system of the present disclosure, the power stage comprises a DC-DC converter. Additionally or alternatively, the power source may be selected from the group consisting of a wall outlet, a generator, and an external battery. In certain embodiments, the power control unit further comprises a switch positioned between the power supply unit and the one or more units with which it is communicatively coupled. The transport path unit may further (optionally) comprise a pad positioned at or near (e.g., positioned over) the at least one open area, with the pad comprising an absorbent material.

The microprocessor of the signal processing unit may be operable to execute the computer readable program code. In yet other embodiments, the detection system may further comprise a separate computing unit. There, the computing unit may comprise a processor operable to execute the computer readable program code, wherein the computer readable program code is accessible by or stored on the computing unit.

The computer readable program code may comprise a computer readable program code means for receiving data from the data transmission unit of the second device, and a computer readable program code means for analyzing data received from the data transmission unit. In such cases, in at least one embodiment, the computing unit may comprise a mobile device and the computer readable program code may comprise a mobile application. Furthermore, at least one of the at least one sensors may be configured to measure photocurrent data from the reagent strip when the reagent strip is dry, when the reagent strip is wet from absorbing a liquid, and after the one or more reagents of the reagent strip have reacted with the liquid. Still further, the concentration of a targeted compound may be calculated using the difference between a first output signal corresponding with photocurrent data from the wet reagent strip and a second output signal corresponding with photocurrent data from the reagent strip that has reacted with the liquid. In additional embodiments, the computer readable program code is further executable to issue a notification if the concentration of the targeted compound is outside of a predefined standard.

Certain detection systems of the present disclosure may comprise a wet sensor in fluid communication with the transport path of the transport path unit and communicatively coupled with the power source, the microprocessor of the signal processing unit, and the power control unit. The wet sensor may be configured to cause the power source unit to conclude a sleep mode event upon receiving liquid from the transport path. In at least one embodiment of a system comprising a wet sensor, the transport path comprises parameters selected such that liquid received through the at least one open area and absorbed into the transport path travels along the transport path to reach the wet sensor prior to reaching the reagent strip of the sensing unit. In yet another embodiment, the transport path unit further comprises a pad positioned at or near (or over) the at least one open area, the pad comprising an absorbent material and configured to deliver received liquid to the sensing strip and the wet sensor. Such a detection system may comprise a microprocessor configured to store the photocurrent data and corresponding output signal(s) converted therefrom. In one or more of the embodiments of the system comprising a set sensor, after the wet sensor causes the power source unit to conclude a sleep mode event, the power source unit may cycle through a series of sleep mode events such that the sensing unit receives power from the power source and the at least one sensor periodically and, in response, measures photocurrent data from the reagent strip.

Additional methods for measuring a concentration of a targeted compound within a bodily fluid using the detection systems hereof are also provided. In at least one embodiment, such a method comprises the steps of: (a) providing power to the sensing unit using the power supply; (b) measuring dry photocurrent data from the reagent strip when in a dry state using the at least one sensor; (c) initiating a sleep mode event using the power control unit; (d) concluding the sleep mode event using the power control unit; (e) measuring photocurrent data from the reagent strip using the at least one sensor; (f) repeating steps (c)-(f) periodically; (g) converting the photocurrent data into one or more output signals; and (h) executing the computer readable program code to analyze the one or more output signals and to calculate a concentration of a targeted compound in the liquid based on the one or more output signals. In at least one embodiment, the step of executing a computer readable program code is performed by the microprocessor of the signal processing unit and comprises calculating the difference between a first output signal corresponding with photocurrent data measured from the reagent strip after the one or more colorimetric reagents thereof completed a reaction with the liquid and a second output signal corresponding with photocurrent data obtained from the reagent strip when wet.

Additionally or alternatively, the methods hereof may further comprise the step of transmitting, using the data transmission unit, the one or more output signals to a computing unit for storage, analysis, and/or display. There, the step of executing a computer readable program code may be performed by a processor of the computing unit and further comprise calculating the difference between a first output signal corresponding with photocurrent data measured from the reagent strip after the one or more colorimetric reagents thereof completed a reaction with the liquid and a second output signal corresponding with photocurrent data obtained from the reagent strip when wet.

Embodiments of the methods hereof may additional comprise the step of comparing the calculated concentration with a predefined standard associated with a health condition, wherein the calculated concentration falling outside of the predefined standard is indicative of the patient experiencing the health condition. There, the step of comparing the calculated concentration with a predefined standard may be performed by executing a computer readable program code, using a processor.

Additional methods are also provided for measuring a concentration of a targeted compound within a bodily fluid using one or more of the detection systems hereof, such methods comprising the steps of: (a) providing power to the sensing unit using the power supply; (b) measuring dry photocurrent data from the reagent strip when in a dry state using the at least one sensor; (c) initiating a first sleep mode event using the power control unit; (d) receiving a liquid from a patient within the at least one open area of the transport path unit and allowing the liquid to absorb into and flow along the transport path; (e) activating the wet sensor with the liquid such that the wet sensor transmits a wake-up signal to the power control unit; (0 in response to the wake-up signal, concluding the sleep mode event using the power control unit; (g) measuring photocurrent data from the reagent strip using the at least one sensor; (h) initiating a second sleep mode event using the power control unit; (i) after a predefined period of time, concluding the second sleep mode event using the power control unit; (j) measuring photocurrent data from the reagent strip in a wet state using the at least one sensor; (k) repeating steps (h)-(j) periodically; (l) converting the measured photocurrent data into one or more output signals; and (m) executing the computer readable program code to analyze the one or more output signals and to calculate a concentration of a targeted compound in the liquid based on the one or more output signals.

In at least one embodiment, the wet sensor comprises at least one liquid-activated battery integrated within the first disposable device.

Kits for the autonomous detection of a health condition within a patient are also provided in the present disclosure. In at least on embodiment, a kit comprises: one or more first disposable devices for embedding or placement within a diaper, each of the first disposable devices comprising: a sensing unit comprising a light source, a sensing strip comprising a reagent strip containing one or more colorimetric reagents for reacting with a targeted compound, and at least one sensor for measuring photocurrent data from the reagent strip, a power source unit in electrical communication with the sensing unit, the power source unit comprising at least one battery operable to power at least the sensing unit, and a transport path unit defining at least one open area configured for receiving liquid therethrough and comprising a transport path comprising a channel extending a length between the sensing unit and the power source unit; and a second device for removable attachment to a diaper, the second device in wired communication with the first disposable device and comprising: a signal processing unit comprising a sensor interface circuit in operative communication with a microprocessor and configured to convert photocurrent data received from the sensing unit into one or more output signals, and a data transmission unit in operable communication with the signal processing unit. Additionally, the kit may further comprise one or more diapers and/or a computer readable program code executable by the microprocessor of the second device to analyze the one or more output signals received from the data transmission unit and calculate a concentration of a targeted compound in liquid received through the transport path based on the one or more output signals, the computer readable program code stored on a storage device.

Where a kit comprises a computer readable program code, the computer readable program code may be further configured to compare the calculated concentration with a predefined standard associated with a health condition, wherein the calculated concentration falling outside of the predefined standard is indicative of the patient experiencing the health condition. In certain embodiments, the second device of the kit may be configured to be communicatively coupled with a computing unit comprising a computer readable program code executable to analyze the one or more output signals received from the data transmission unit and calculate a concentration of a targeted compound in liquid received through the transport path based on the one or more output signals, the computer readable program code stored on a storage device, the computer readable program code comprising a mobile application for use with a mobile device. Additionally or alternatively, the computer readable program code may be further configured to compare the calculated concentration with a predefined standard associated with a health condition. In such cases, the calculated concentration falling outside of the predefined standard may be indicative of the patient experiencing the health condition.

Furthermore, additional embodiments of multisensory detection systems are also described in the present disclosure. One such example comprises a system comprising: a first disposable device for embedding or placement within a diaper, the first disposable device comprising: a sensing unit comprising a sensing strip comprising a first end and a second end, the second end comprising: a first light source, a first reagent strip containing one or more colorimetric reagents for reacting with a first targeted compound, and at least one first sensor for measuring photocurrent data from the first reagent strip, and a second light source, a second reagent strip containing one or more colorimetric reagents for reacting with a second targeted compound, and at least one second sensor for measuring photocurrent data from the second reagent strip; a power source unit in electrical communication with the sensing unit, the power source unit comprising at least one battery operable to power at least the sensing unit, and a transport path unit defining at least one open area configured for receiving liquid therethrough and comprising a transport path comprising a channel extending a length between the first end of the sensing unit and the power source unit; a second device for removable attachment to a diaper, the second device in wired communication with the first disposable device and comprising: a signal processing unit comprising: a microprocessor, a sensor interface circuit in operative communication with the microprocessor and configured to convert photocurrent data received from the sensing unit into one or more multichannel output signals, and a multiplexer in operative communication with the microprocessor, the multiplexer configured to switch between channels of the multichannel output signals such that a distinction can be made between the photocurrent data received from each of the first and second reagent strips of the sensing unit, and a data transmission unit in operable communication with the signal processing unit; and a computer readable program code executable to analyze the one or more output signals received from the data transmission unit and calculate a first concentration of the first targeted compound in liquid received through the transport path based on the one or more output signals received from the first reagent strip, and a second concentration of the second targeted compound in the liquid received through the transport path based on the one or more output signals received from the second reagent strip. In such cases, the second end of the sensing unit may also comprise a third light source, a third reagent strip containing one or more colorimetric reagents for reacting with a third targeted compound, and at least one third sensor for measuring photocurrent data from the third reagent strip. Additionally or alternatively, the distinction between the photocurrent data received from each of the reagent strips of the sensing unit is based on a timing protocol. In at least one exemplary embodiment, the microprocessor may be configured to decode the multichannel output signals based on the timing protocol.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIG. 3b shows an alternative multisensory embodiment of the sensing strip of FIG. 3a;

FIGS. 4a-4c show top (FIGS. 4a and 4b) and a cross-sectional view (FIG. 4c) of a power source unit and the liquid-activated batteries thereof of an exemplary embodiment of the detection system of FIG. 1a;

FIGS. 5c and 5d show a top view and a perspective view, respectively of two disposable devices of the detection system of the present disclosure;

FIGS. 6a and 6b show top (upper images) and cross-sectional (lower images) views of exemplary embodiments of the detection system of the present disclosure, with the cross-sectional view of FIG. 6a taken along line A-A of the top view shown in FIG. 6a and the cross-sectional view of FIG. 6b taken along line B-B of the top view shown in FIG. 6b;

FIGS. 7a and 7b show a path unit of the system of the present disclosure comprising two transport paths;

FIG. 17a is a flow chart of an operational sequence associated with the detection system of FIG. 1a, and FIG. 17b is a timing diagram associated with the method shown in FIG. 17a;

FIG. 20b is a flow chart of a method for using the detection system of FIG. 20a;

Figure 1A:
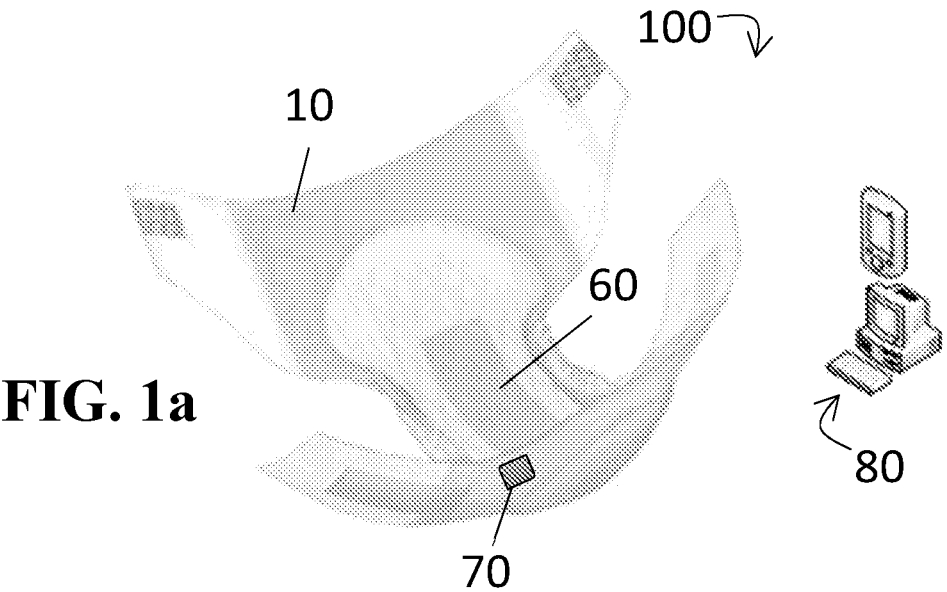
FIGS. 1a-1c show exemplary embodiments of a detection system and the devices thereof pursuant to the present disclosure.

The flow charts and schematics depicted in the figures are representative in nature and actual embodiments of the systems and methods hereof may include further features or steps not shown in the drawings. The exemplification set out herein illustrates an embodiment of the systems and methods, in one form, and such exemplifications are not to be construed as limiting the scope of the invention in any manner. An overview of the features, functions and/or configurations of the components depicted in the various figures will now be presented. It will be appreciated that not all of the features of the components of the figures are necessarily described. Some of these non-discussed features, as well as discussed features, are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings and specific language will be used to describe the same. It will nevertheless be understood that no limitation of scope is intended by the description of these embodiments. On the contrary, this disclosure is intended to cover alternatives, modifications, and equivalents as may be included within the spirit and scope of this application as defined by the appended claims. As previously noted, while this technology may be illustrated and described in one or more preferred embodiments, the compositions, systems and methods hereof may comprise many different configurations, forms, materials, and accessories.

In the following description, numerous specific details are set forth in order to provide a thorough understanding of the present disclosure. Particular examples may be implemented without some or all of these specific details and it is to be understood that this disclosure is not limited to particular biological systems, which can, of course, vary.

Various techniques and mechanisms of the present disclosure will sometimes describe a connection or link between two components. Words such as attached, linked, coupled, connected, and similar terms with their inflectional morphemes are used interchangeably, unless the difference is noted or made otherwise clear from the context. These words and expressions do not necessarily signify direct connections, but include connections through mediate components and devices. It should be noted that a connection between two components does not necessarily mean a direct, unimpeded connection, as a variety of other components may reside between the two components of note. Consequently, a connection does not necessarily mean a direct, unimpeded connection unless otherwise noted.

Furthermore, wherever feasible and convenient, like reference numerals are used in the figures and the description to refer to the same or like parts or steps. The drawings are in a simplified form and not to precise scale. It is understood that the disclosure is presented in this manner merely for explanatory purposes and the principles and embodiments described herein may be applied to devices and/or system components that have dimensions/configurations other than as specifically described herein. Indeed, it is expressly contemplated that the size and shapes of the composition and system components of the present disclosure may be tailored in furtherance of the desired application thereof.

Unless defined otherwise, all technical and scientific terms used herein have the same meaning as commonly understood by one of skill in the relevant arts. Although any methods and materials similar to or equivalent to those described herein can be used in the practice or testing of the subject of the present application, the preferred methods and materials are described herein. Additionally, as used in this specification and the appended claims, the singular forms "a", "an" and "the" include plural referents unless the content clearly dictates otherwise.

As used herein, the phrase "communicatively connected" means any type of connection, wired or wireless, for communicating data between two or more components or devices (including, without limitation, between components of the detection system 100 and the computing unit 112 and/or between external devices/databases and the computing unit 112).

As used herein, the term "user" means and includes a user who is monitoring and/or screening a patient or other individual for a UTI, another disorder, or otherwise using the systems, devices, and methods hereof to evaluate a patient's health. The user may be the patient his or herself, or a healthcare provider or caregiver.

As used herein, the term "patient" means and includes an individual wearing the devices and systems of the present disclosure to provide liquid/urine for analysis.

Figure 1B:
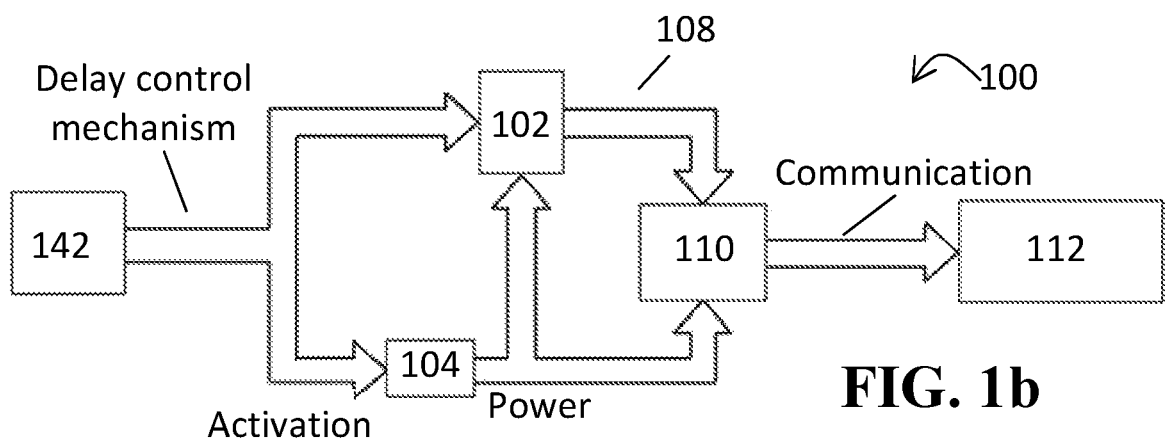
Figure 1C:
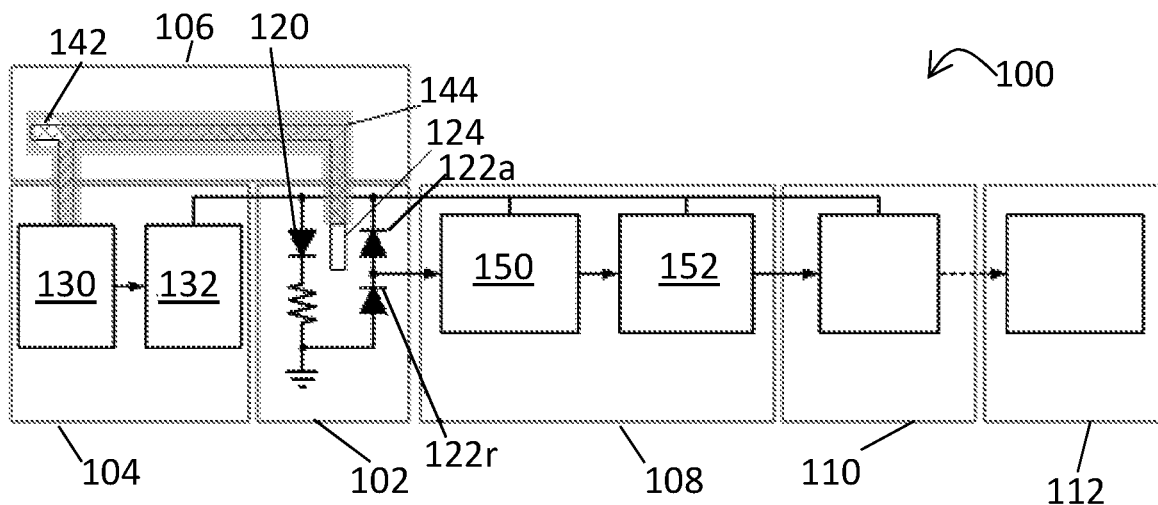

Generally, the present disclosure provides systems and methods relating to a novel detection system and related devices that allow for the early detection and screening of UTI and other disorders in a noninvasive and easy to implement manner. Referring to FIGS. 1a-1c, a detection system 100 comprises a disposable device 60, a reusable device 70, and software 80 running on a computing unit 110 (often positioned remotely relative to devices 60, 70 and the diaper 10). The disposable device 60 may either be embedded in a diaper 10 (or other similar garment) during the manufacturing process or attached as an added unit to a commercially available diaper 10 (i.e. "add-on" or retrofit embodiments). The disposable device 60 is positioned within the diaper 10 at a location conducive to receiving urine or liquid therein and, in at least one embodiment, is concealed within the material of the diaper 10 itself. Embedding or adding the disposable device 60 to the diaper 10 facilitates the autonomous monitoring functionality provided by the detection system 100.

The disposable device 60 is configured for single-use application and comprises a sensing unit 102, a power source unit 104, and a transport path unit 106 extending therebetween. The sensing unit 102 comprises a sensor configured to detect photocurrent data associated with a targeted ion or compound (collectively, the "targeted compound") present (or lacking) in urine or other liquid collected within the diaper 10 and received into the disposable device 60 through open area(s) 142. The sensing unit 102 is fabricated on a flexible substrate and may be configured to detect nitrite, nitrate, protein, hemoglobin, erythrocytes or hematuria (red blood cells), white blood cells, leucocyte esterase, excessive amounts of protein, or any other targeted compounds within the urine/liquid as desired and for which reactive colorimetric reagents/chemicals are available. In addition, in certain embodiments described in additional detail below, the sensing unit 102 may also be configured to comprise multi-parameter sensing to increase diagnostic sensitivity and specificity, while also reducing the incidence of false negatives.

Due at least in part to cost and environmental issues, the disposable device 60 is self-powered. Accordingly, in at least one exemplary embodiment, the power source unit 104 is urine- and/or liquid-activated.

The disposable device 60 is in wired communication with the reusable device 70 of the detection system 100. The reusable device 70 can removably affixed to the exterior of the diaper 70 either by a user or the patient/individual wearing the diaper 70. In at least one embodiment, a wire (not shown) in electronic communication with the disposable device 60 extends just beyond the exterior of the diaper 70 and allows for convenient electronic coupling (and therefore communication) with the reusable device 70.

The reusable device 70 comprises the electrical componentry of the detection system 100, including a sensor signal processing unit 108, a data transmission unit 110 and, optionally, a power control unit (not shown). The sensor processing unit 108 comprises embedded firmware for sensor signal processing. Perhaps more specifically, the sensor processing unit 108 receives the data collected by the sensor of the sensing unit 102 and converts the same to digital form. The digital data is thereafter sent for analysis to the software 80 running on a remote device by the data transmission unit 110, which may employ wired or wireless technologies. In at least one exemplary embodiment, the data transmission unit 110 employs Bluetooth (BLE) technology to transfer the digital data and otherwise communicate with a remote device.

The power source unit 104 of the disposable device 60 provides power to operate the components of the reusable device 70. In an exemplary embodiment, the sensor signal processing unit 108 utilizes power-efficient, pulse width modulation techniques to provide a design that facilitates continuous operation of the system 100 using only liquid-activated battery cells such that the detection system 100 is self-powered and allows for autonomous operation.

The optional power control unit of the reusable device 70 comprises a microcontroller or microprocessor communicatively connected with the sensing unit 102, the sensor signal processing unit 108, and the data transmission unit 110. When used in connection with the detection system 100, the power control unit can be configured to implement sleep modes in connection with operation of the system 100 to reduce power consumption and increase efficiency.

The software 80 running on the computing unit 112 is configured to store, track, display, and quantitatively evaluate data received from the reusable device 70 (on a case by case basis or cumulatively, over time). The software 80 can also be used to detect if the patient is presenting with an infection or other health issue—such as a UTI—based on the data received and the quantitative analysis performed. This analysis and detection is performed quickly; for example, within a few minutes following urination or the like.

Additional features of such software 80 may include performing calibration algorithms, providing notifications to the user or another healthcare provider or caregiver based on the evaluated data (e.g., if the diaper 10 is wet or if a targeted compound is present within the urine/liquid at a concentration outside of a predefined threshold), providing reminders of upcoming doctor's appointments to the patient and/or reminders to take medication, providing doctor's office referrals in the event a disorder is detected based on the data received, providing health related information to the user related to the patient (e.g., regarding demographics, diet/vitamin deficiencies, current therapies, training, etc.), and interfacing with medical health information networks to add to and/or provide a comprehensive view of a patient's health information. The functionality of the software 80 may be easily expanded as desired and the foregoing list is not intended to be limiting in any way. In at least one exemplary embodiment, the computing unit 112 comprises a smartphone and the software 80 comprises a mobile application.

The dual-module, disposable and reusable design of the detection system 100 not only delivers quick and accurate results, but also provides a fully autonomous system suitable for daily monitoring over an extended period. The detection system 100 does not present privacy or dignity issues for the patient, does not inhibit movement or inconvenience when worn, and is low cost. Furthermore, after urination or the diaper 10 is soiled, the reusable device 70 can be easily removed and the diaper 10 replaced (with the disposable device 60 disposed of with the soiled diaper 10).

While the detection system 100 and related devices and methods of the present disclosure are described herein predominantly in connection with urine and the detection of UTIs, it will be appreciated that the novel concepts hereof may be applied to additional liquids and/or the detection and analysis of other health-related data points. For example, the detection system 100 may be additionally or alternatively designed to detect for the excretion of red blood cells and/or other substances or compounds present within the urine, which can be indicative of kidney disease, kidney stones, tumors, or other disease states or physiological conditions. Furthermore, while many of the systems and devices described are designed for autonomous patient use, this need not necessarily be the case. Indeed, the concepts underlying the systems, devices, and methods hereof may be utilized in connection with an in-office detection device/system or the like.

The specific components of the systems, devices, and methods hereof, as well as notable variations, will now be described in detail.

Now referring to FIG. 1c, a schematic diagram of at least one embodiment of the detecting system 100 is shown. The system 100 may be configured to be capable of self-wake-up, self-power, detection of UTI or other targeted disease or disorder, and the wireless transmission of information. In at least one exemplary embodiment and as previously stated, the system 100 comprises a disposable device 60 comprising a sensing unit 102, a power source unit 104, and a path unit 106; a reusable device 70 comprising a sensor signal processing unit 108 and a data transmission unit 110; and software 80 running on a computing unit 112. Each of the foregoing units/devices 60, 70 are in operative communication with at least one other unit/component of the system 100.

Figure 6C:
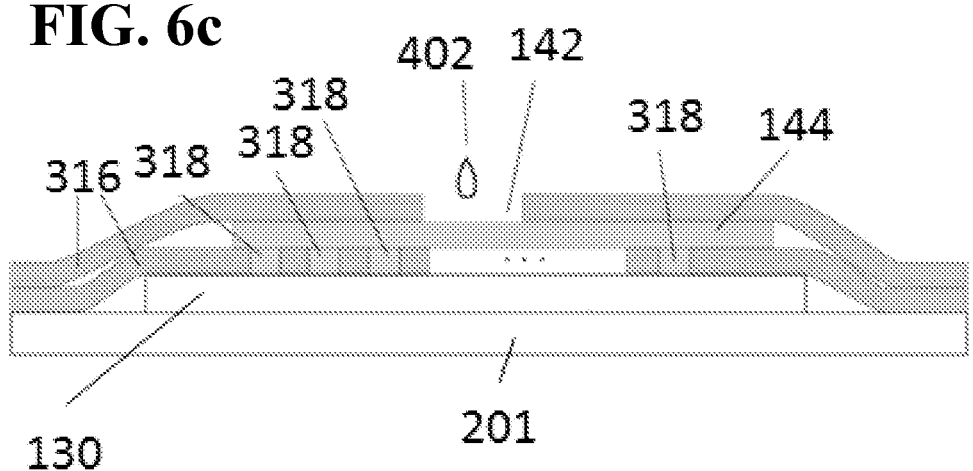
FIGS. 6c and 6d show a cross-sectional view and a top view, respectively of two disposable devices of the detection system of the present disclosure.

The units of the disposable device 60 are positioned on and/or at least partially within a hydrophobic substrate 201 (see also FIGS. 6a-6c). The disposable device 60 may be hermetically sealed for insulation and to minimize irritation to the patient. In at least one embodiment, the overall size of the disposable device 60 is generally bandage size, such that it can comfortably fit within a diaper 10.

Sensing Unit

The sensing unit 102 is the portion of the system 100 that actively senses a concentration of one or more targeted compounds present within a liquid being tested (for example, nitrate and/or nitrate present within urine). The sensing unit 102 comprises at least one light source 120, at least one photodetector 122, a sensing strip 124, and metallic traces for electrical connection to an external interface and/or RF circuit ("electrical connections 226").

Figure 2A:
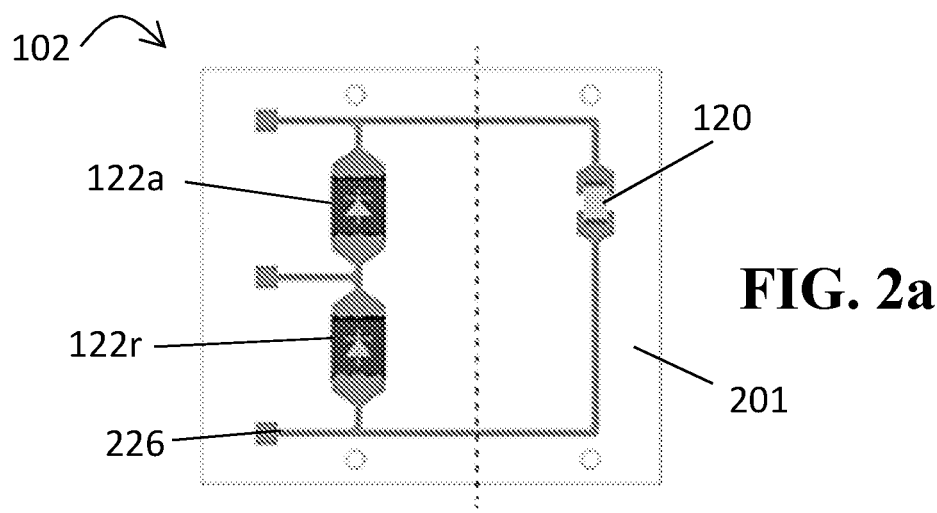
FIGS. 2a-2d show a top view, a perspective view, and two schematic views (respectively) of a sensing unit of the detection system of the present disclosure.
Figure 2B:
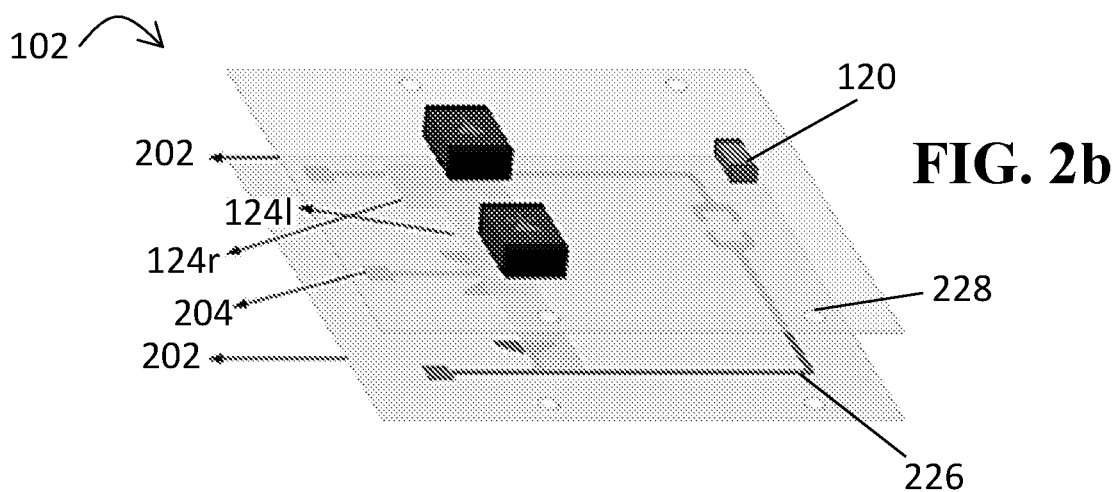

As previously noted, the components of the sensing unit 102 may be integrated onto a flexible substrate 201 as shown in FIGS. 2a and 2b. The flexible substrate 201 comprises a wax paper or the like and exhibits expansibility and a high degree flexibility. In at least one embodiment, the flexible substrate 201 is hydrophobic.

The flexible substrate 201 may define one or more openings 228 either formed therein or due to the position thereof when the device 60 is assembled (e.g., where an opening 228 is purposefully defined between an edge of the flexible substrate 201 and another material used to define an external boundary of the system 100) (see FIGS. 6a and 6b). The openings 228 may be configured for passing and positioning the sensing strip 124 between the photodetector(s) 124 and the light source 120 and/or aligning the photodetector 124 and the light source 120 during manufacture as described below. An opening 228 may also define the junction between the battery 130 and the photodetector(s) 124/light sources 120 and, in at least one embodiment, may be insulated to prevent the battery 130 from shorting out during operation of the disposable device 60.

The light source 120 may be any light source suitable for the present application that is now known or hereinafter developed such as, for example, a light emitting diode ("LED"), a laser, or the like. FIGS. 2a and 2b show details of the sensing unit 102 on a flexible substrate 201 and an exploded view of the sensing unit 102, respectively. While a single light source 120 is provided in FIGS. 2a and 2b, it will be appreciated that the system 100 may comprise any number of light sources 120 as may be preferred by a user and/or advantageous, with each of the light sources 120 positioned on the substrate 201 to be in alignment with at least one photodetector 122 and/or a sensing strip 124.

The at least one photodetector 122 comprises at least one an active photodetector 122a and one or more reference photodetectors 122r connected in series thereto, if desired (see FIG. 2a). The active photodetector 122a is operable to sense the color density of the sensing strip 124, which can be further facilitated through illumination of the light source 120. Likewise, a reference photodetector 122r in the sensing unit 102 may be used to cancel out the dark current of the active photodetector 122a and to provide high impedance. Notably, when dark current is not significant, reference photodetectors 122r need not be employed in the sensing unit 102. In at least one embodiment, the reference photodetector 122r may be removed and replaced with a capacitor.

Figure 2C:
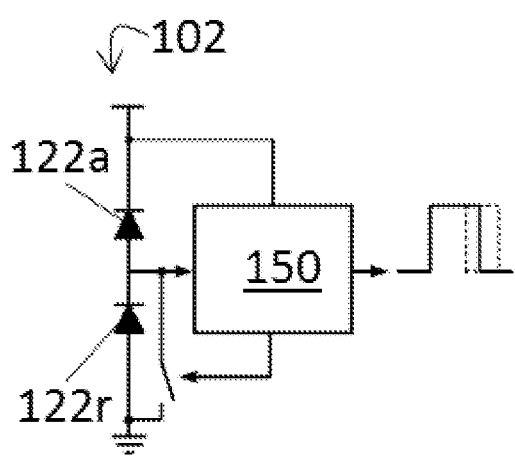
Figure 2D:
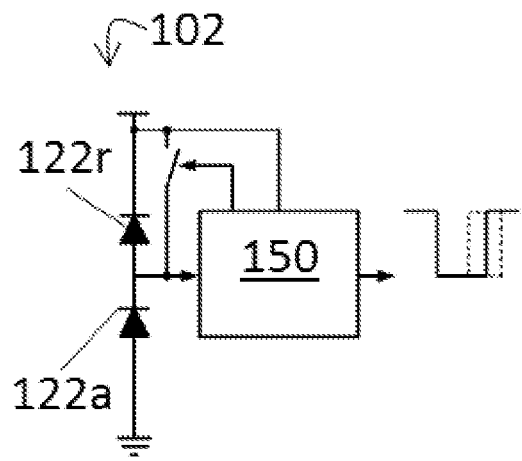

The roles of the photodetectors 122 are changeable. In at least one embodiment where the sensor interface circuit 150 comprises a PWM adjustable circuit, if the top photodetector 122 is used as the active photodetector 122a, the high pulse width of the PWM circuit 150 is modulated (see FIG. 2c). Alternatively, if the bottom photodetector 122 is used as the active photodetector 122a (see FIG. 2d), the low pulse width of the PWM circuit 150 is modulated. Staking at least two photodetectors 122 in series helps to cancel out any dark current for most sensor interface configurations. By way of example, FIGS. 2c and 2d show two photodetectors 122a, 122r stacked in two different ways and coupled with a pulse width modulation ("PWM") sensor interface circuit 150.

Figure 3A:
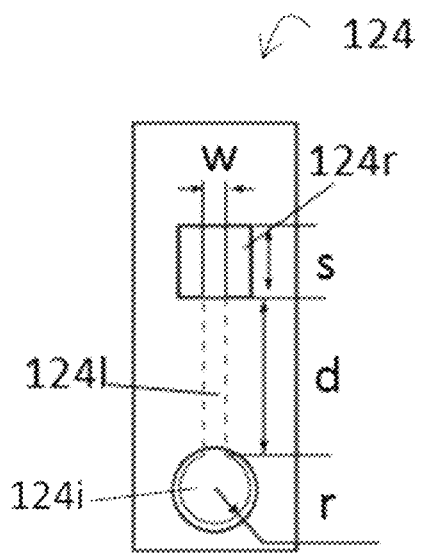
FIG. 3a shows an exemplary embodiment of a sensing strip associated with the sensing unit of FIGS. 2a-2c

FIG. 3a shows at least one embodiment of a sensing strip 124 pursuant to the present disclosure. The sensing strip 124 comprises a liquid-absorbing strip 1241 (which comprises an inlet 124i) and a reagent strip 124r that contains at least one chemical for reacting with one or more targeted compounds or ions and providing a visual indication if present. In at least one exemplary embodiment, the sensing strip 124 comprises a liquid-absorbing (e.g., paper), colorimetric strip configured to display a certain color dependent upon the nitrite and/or nitrate concentration present within a substance being tested, with the reagent strip 124r comprising a reagent impregnated matrix. For example, as in UTI dipstick, when the sensing strip 124 is wetted, a reaction proceeds along the reagent strip 124r and the color of the reactants (liquid and reagents, for example, a "Griess reagent" for nitrite and/or a "Griess+reducing" agent for nitrate, with the reducing agents being cadmium redactor, nitrate reductase, or others) therein develop and the color(s) of the reagent strip 124r may change (e.g., from white to pink) when a targeted ion or compound (e.g., nitrate and/or nitrite) is present within the liquid (i.e. urine) absorbed by the sensing strip 124. Furthermore, the color density of the sensing strip 124 may also be a function of the concentration of the ion/compound detected within the liquid being tested. The geometry of the sensing strip 124 may be modified to adjust the duration of dry measurement that is achievable, which is discussed in additional detail below. For example and with reference to FIG. 3a, to secure at least 10 seconds of dry measurement in the sensing strip 124 (i.e. enough time for the battery 130 to generate sufficient power to turn on the measurement circuit), the dimensions of the sensing strip 124 may be as follows: r=7 mm, d=27 mm, w=1.6 mm, and s=5 mm.

Referring back to FIG. 2a, the sensing strip 124 is positioned such that, when the flexible substrate 201 is folded along the dashed line of FIG. 2a, the sensing strip 124 is sandwiched between the light source 120 and at least one of the photodetectors 122 (i.e. active photodetector 122a). In this manner, both the light source 120 and photodetector 122a are adjacent to the reagent strip 124r of the sensing strip 124. In operation, when a liquid absorbs into the liquid-absorbing strip 1241 of the second layer, as previously noted, the liquid spreads until it arrives at the reagent strip 124r of the third layer that contains the desired reagent. The liquid then reacts with the reagent present within the reagent strip 124r to produce a positive indicator—such as a specific color—if the substance being tested for is present within the liquid. In at least one embodiment, the positive indicator is also able to reflect the concentration of the identified substance. Due to the placement of the active photodetector 122a relative to the sensing strip 124/reagent strip 124r, the color and/or color density of the sensing strip 124 affects the intensity of the light that can reach the active photodetector 122a and, thus, the photocurrent generated thereby (i.e. output).

Notably, light from the light source 120 need not reach the reference photodetector 122r; instead, photodetector 122r is utilized by the system 100 to compensate for any leakage dark current. Due to the weak sensitivity of the leakage dark current to the bias voltage, the leakage dark current of the photodetectors 122 is almost the same. Because the photodetectors 122 are connected in series, the balanced leakage dark currents cancel each other out and do not affect the output of the sensor signal processing unit 108 (described in additional detail below). Additionally, the photodetectors 122 also provide a high impedance node required for charge accumulation.

Figure 3B:
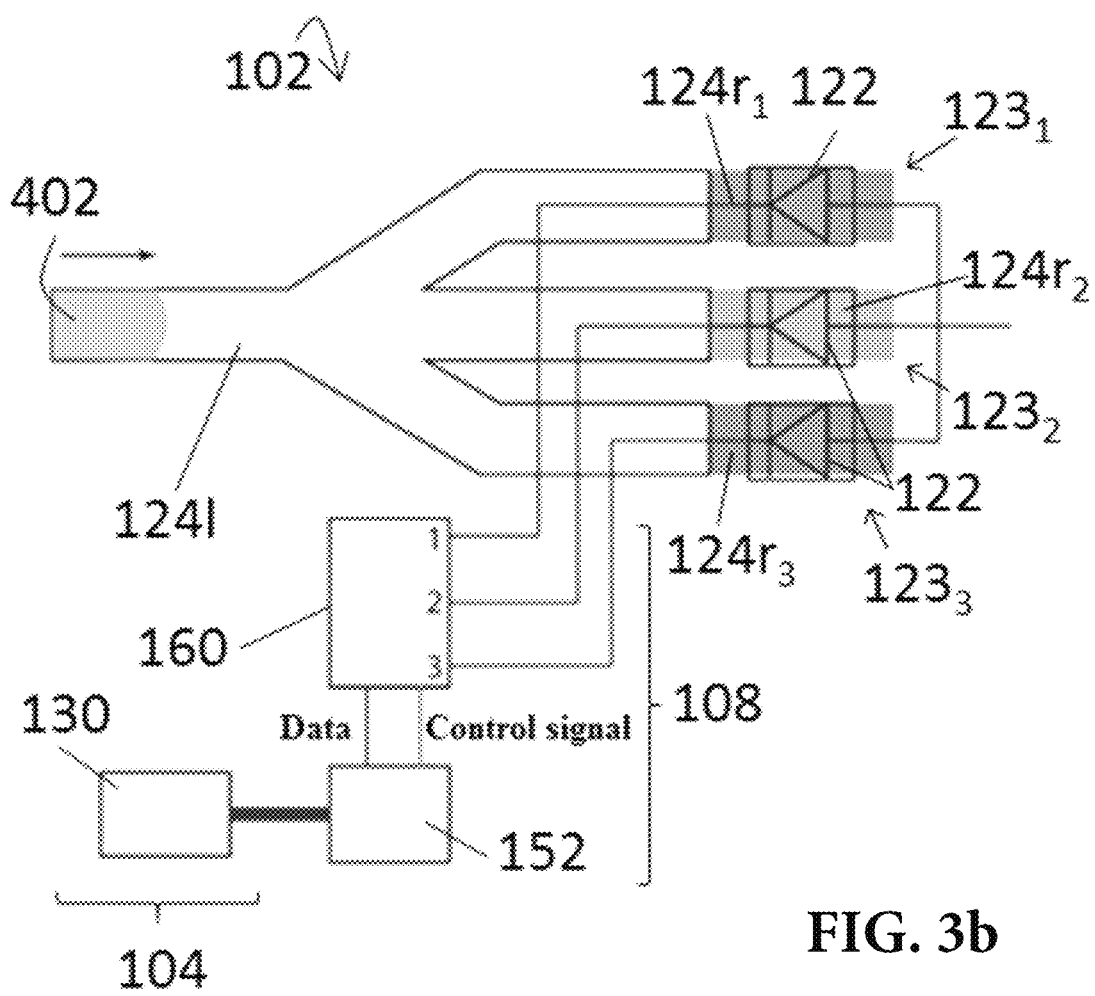

Now referring to FIG. 3b, in at least one embodiment, the sensing unit 102 may comprise a multisensory embodiment. Here, the sensing unit 102 and components thereof are configured as previously described; however, the sensing unit 102 comprises multiple light sources 120 and photodetectors 122 (comprising the same or different colors, depending on the targeted assay color change) that are each associated with a different reagent strip $124r_{1,2,3}$ and turned on sequentially. Each of the reagent strips $124r_{1,2,3}$ may comprise different reagents to concurrently test for various substances within the liquid absorbed into the sensing strip 124. For example, the first reagent strip $124r_1$ may comprise reagents for detecting red blood cells (or hematuria), the second reagent strip $124r_2$ may comprise reagents for detecting the presence of an elevated amount of protein (albumin), and the third reagent strip $124r_3$ may comprise reagents for detecting the presence of nitrite. While three different reagent strips are shown in FIG. 3b, it will be appreciated that any number of reagent strips may be utilized as desired and such example is not intended to be limiting.

In operation, when a liquid 402 absorbs into the liquid-absorbing strip 1241 of the second layer, as previously noted, the liquid 402 spreads until it arrives at the reagent strips $124r_{1,2,3}$ of the third layer that contain the desired reagents. The liquid 402 then reacts with the reagent present within each reagent strip $124r_{1,2,3}$ to produce a positive indicator—such as a specific color—if the substance being tested for is present within the liquid 402. The positive indicator may also able to reflect the concentration of the identified substance. As in previously described embodiments, due to the placement of the active photodetectors 122a relative to the sensing strip 124/reagent strips $124r_{1,2,3}$, the color and/or color density of each reagent strip $124r_{1,2,3}$ affects the intensity of the light that can reach the associated active photodetector 122a and, thus, the photocurrent generated thereby (i.e. output). In this manner, a single sensing strip 124 can be used to collect data from the urine from regarding multiple conditions such that a multi-parameter diagnosis can be made. As previously noted, this may result in the reduction of false-negatives and false-positives since multiple data points are collected concurrently. Furthermore, as some reagents do not exhibit the same degree of sensitivity and/or specificity as others (see FIG. 3c), multi-parameter sensing can be employed to concurrently test for those with various ranges of sensitivities/specificities to increase the overall accuracy of the results.

Consider, for example, the at least one embodiment described above where the first reagent strip $124r_1$ comprises reagents for detecting red blood cells (or hematuria), the second reagent strip $124r_2$ comprises reagents for detecting the presence of an elevated amount of protein (albumin), and the third reagent strip $124r_3$ comprises reagents for detecting the presence of nitrite. Hemoglobin or myoglobin present within the liquid (urine) catalyzes the oxidation of a certain color indicator in the first reagent strip $124r_1$ (e.g., greenish-yellow=erythrocytes free, whereas dark blue=high concentration of erythrocytes) and the light source 120/photodetector 122 module may comprise a wavelength range of about 600-700 nm (red), with dipstick detection limits comprising 10 erythrocytes/μL (a healthy range being established at less than 5 erythrocytes/μL, for example). However, a positive indication of hematuria (or the excretion of red blood cells in the urine) on the first reagent strip $124r_1$ alone may result from numerous causes including a UTI, kidney disease, kidney stones, or tumors and, as such, may not be enough to positively diagnose any particular disorder. Where the multisensory embodiment is used, the second reagent strip $124r_2$ also tests for an elevated or excessive amount of protein in the liquid (urine), of which albumin may take up the largest portion. There, the light source 120/photodetector 122 module may comprise a wavelength around 610 nm, with dipstick detection limits comprising greater than about 6 mg/dL (a healthy range being established at less than 10 mg/L, for example). Because proteinuria or albuminuria is one of the earliest symptoms of kidney diseases, if the second reagent strip $124r_2$ identifies an elevated amount of protein within the urine, this result, especially taken with a positive result for hematuria from the first reagent strip $124r_1$, may be more conclusive of a kidney disease diagnosis. The third reagent strip $124r_3$ (or any additional number of strips $124r_n$) can also be used to further confirm and/or clarify the test results. It will be appreciated that any number and/or types of reagents/reagent strips $124r_n$ may be used in this multisensory design to achieve useful diagnostic and/or user-specific results.

Accordingly, the multi-parameter sensing provided by the multisensory embodiment of the sensing unit 102 can improve the overall diagnostic accuracy and usefulness of the noninvasive urine analysis of the present disclosure. The multisensory embodiment decreases the number of independent tests that a patient must undergo and decreases the overall amount of time required for a clinician or healthcare provider to arrive at a diagnosis. This may be especially advantageous for the subset of patients previously identified (e.g., infants and geriatric patients), and with diseases and/or conditions where timely diagnosis can make a significant impact on recovery (e.g., as with chronic kidney disease that can lead to kidney failure if not identified and treated in a timely fashion).

Power Source Unit

Figure 4A:
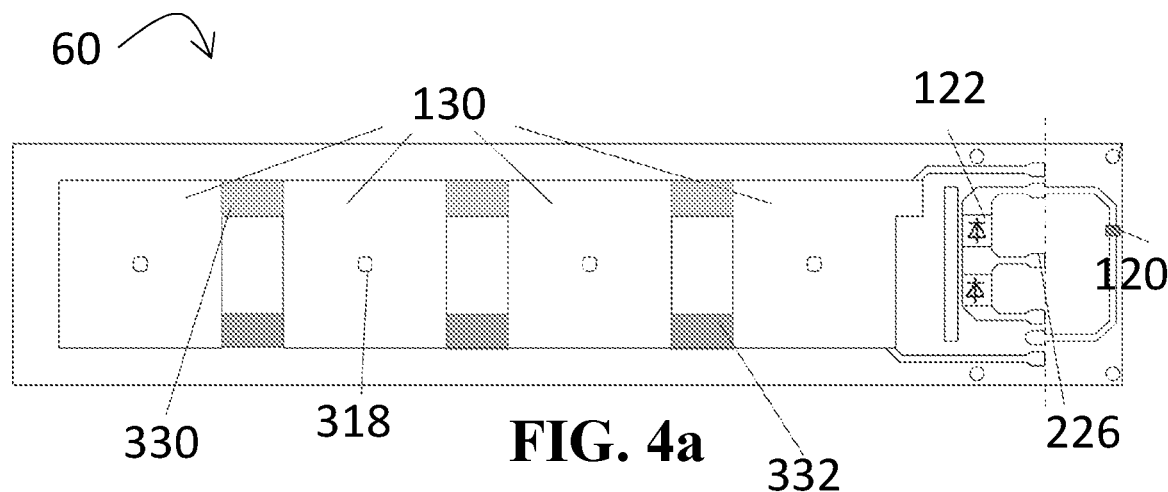
Figure 4B:
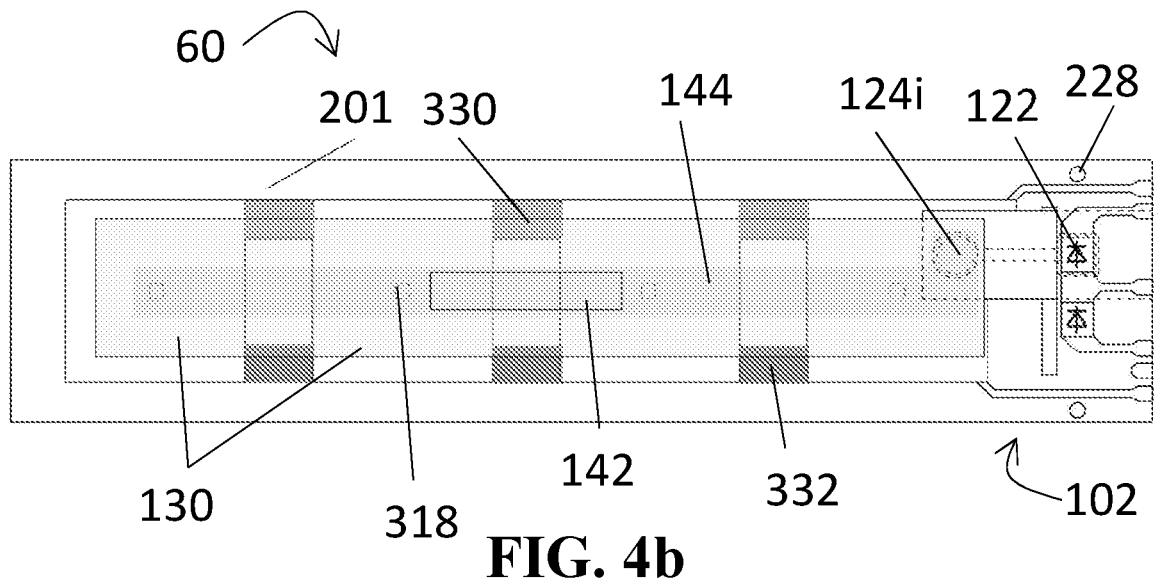
Figure 4C:
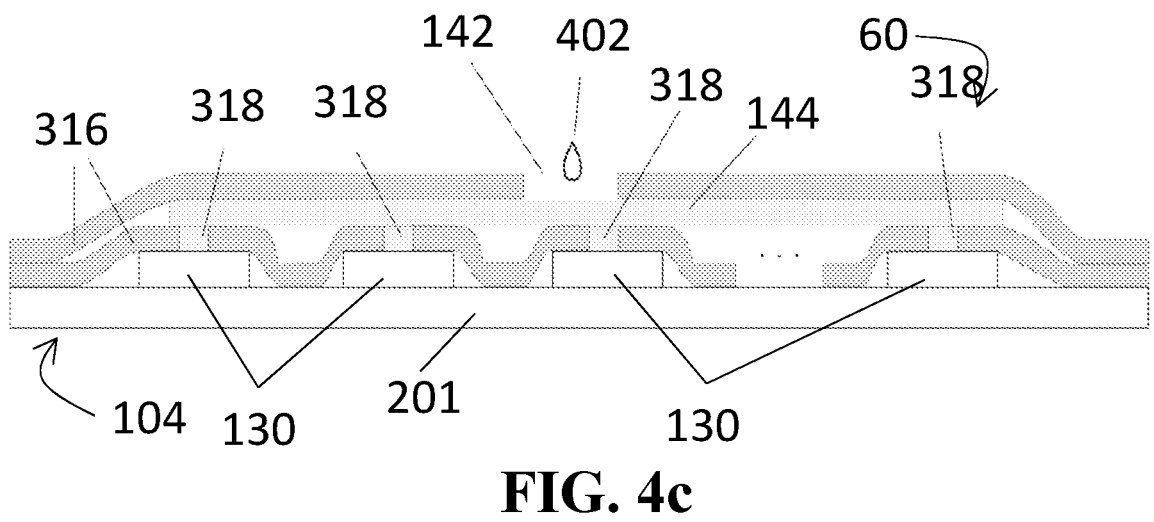

The power source 104 of the detection system 100 is electrically coupled with the sensing unit 102 and, in at least one embodiment, is part of at least the disposable device 60 and comprises at least one liquid-activated battery 130 and a power conditioning stage (power stage 132). The power source 104 may comprise a single, large cell, liquid-activated battery 130 (not shown) or, alternatively, two or more liquid-activated batteries 130 connected in parallel or series. As shown in FIGS. 4a and 4b, in at least one embodiment, the power source unit 104 comprises four (smaller) liquid-activated batteries 130 connected in parallel (connection between positive ends 330 and connection between negative ends 332). The parallel design enlarges the overall dimensions of the system 100/device, but increases its bendability, which is beneficial and may be preferable for deployment in a diaper. The multiple-battery 130 design also facilitates activation of the batteries 130 prior to liquid arriving at the sensing strip 124, with the path unit 106 connecting the sensing strip 124 and a series of battery openings 318 in fluid communication with the batteries 130. Despite the foregoing descriptions, it will be appreciated that any number or types of batteries may be employed (represented in FIG. 4c by the ellipsis between the parallel batteries 130) and/or connected in any manner appropriate.

Furthermore, in at least one alternative embodiment, the "battery 130" of the power source unit 104 may comprise an external power source (not shown) instead of or in addition to a liquid-activated battery 130 positioned within the disposable device 60. In this scenario, the external power source is positioned outside of a diaper in which the detection system 100 is embedded or positioned. This alternative embodiment is described in further detail below and in connection with FIGS. 12a and 12b.

The output voltage provided by the battery(ies) 130 need not be consistent, but instead may vary (e.g., between at or about 0.3V to at or about 0.9V). To facilitate the reliable function of the battery 130, its voltage may be boosted and/or regulated by the power stage 132. In at least one embodiment, if the voltage of the battery 130 is lower than the regulated voltage, a DC-DC or other boost converter may be used in the power stage 132, for example, to regulate voltage to at or about 2.0V and/or comprise a power conversion efficiency of between 50-60%. If the voltage of the battery 130 is higher than the regulated voltage, a buck converter may also be used in the power stage 132. It will be appreciated that the power stage 132 may be used in connection with embodiments where the battery 130 of the power source unit 104 comprises a liquid-activated battery 130 positioned within the disposable device 60 and/or with embodiments comprising an external power source. Additionally or alternatively, while the power stage 132 is in electrical communication with the liquid-activated battery 130 and/or external power source, the power stage 132 may be positioned in the reusable device 70 such that it need not be replaced each time a diaper 10 is soiled and/or otherwise replaced.

Figure 4D:
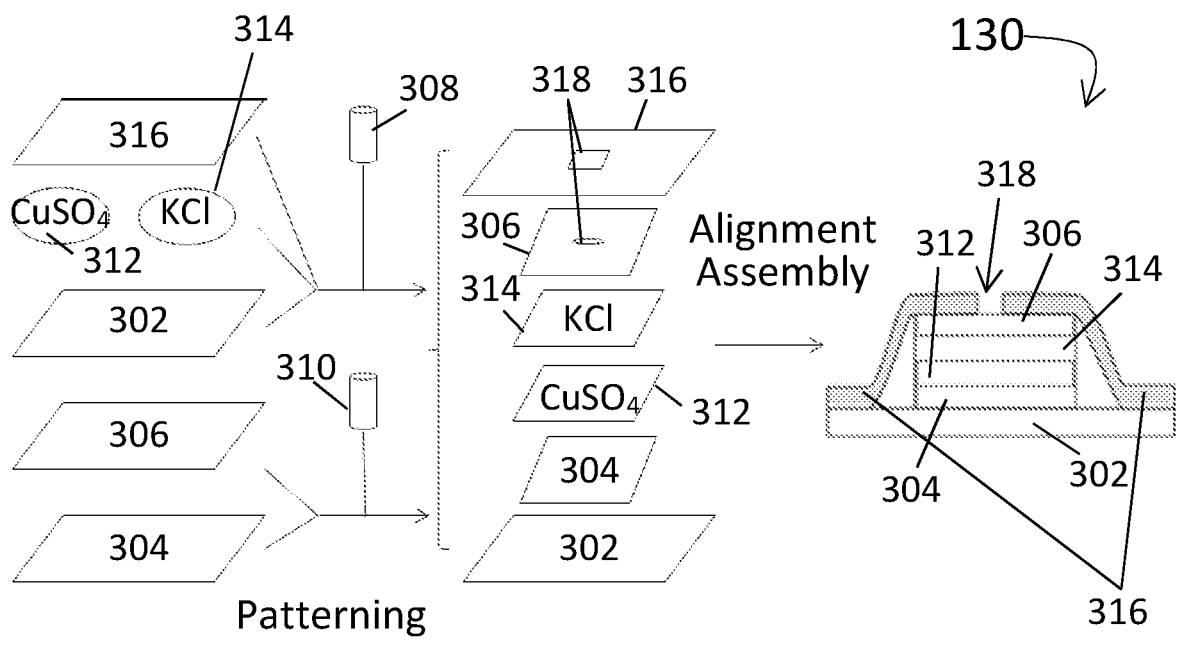
FIG. 4d shows a schematic diagram illustrating the process of manufacturing a liquid-activated battery of FIG. 4a-4c.

As previously noted, in at least one exemplary embodiment, the power source 104 comprises at least one liquid-activated battery 130. This is advantageous as it enables the system 100 to be self-powered and configured for self-wake-up as the power source 104 may be urine-activated. Indeed, urine/liquid-activation simplifies the design of the system 100 by eliminating the need for periodic wakeup for checking the event of urination, which is required for conventional systems that rely on a continuously powered battery. Urination-event driven automatic activation and wakeup also increases the shelf-life of the sensing unit 102 and eliminates color fading issues because the sensing is guaranteed to happen within a short time frame after the urination event.

Where a battery 130 is liquid-activated, in at least one exemplary embodiment, the battery 130 comprises a Zn—Cu electrochemical cell (having, for example, two half cells ($Cu/CuSO_4$ and $Zn/ZnCl_2$) and a salt bridge) that provides a theoretical potential difference of 1.1V. A schematic representation of an exemplary embodiment of a fabrication process for such battery 130 is shown in FIG. 4d. The process generally entails: (a) cutting a variety of active materials into patterns (i.e. laser-defining the substrate) and covering the same with polyimide tape; (b) aligning and assembling the patterned layers as desired, and (c) taping/laminating the layers together to ensure that at least one opening 318 is positioned on the outside of the layers such that liquid seep through and into the interior.

Perhaps more specifically, a $CO_2$ laser 310 (e.g., from Universal Laser Systems, PLS6MW, 10.6 µm $CO_2$ laser) may be used to machine a sheet of wax paper 302 (e.g., Reynolds Cut-Rite, 40 µm thick) into a 3 cm square substrate (notably, wax paper 302 may comprise the same material as substrate 201). Copper tape 304 and zinc tape 306 (at or about 50 µm and 100 µm thick, respectively), both with an adhesive backing, may also be carved into 2.5 cm squares having electrical connection protrusions (not shown) by a 1.06 µm fiber laser 308 or the like to create the metal electrodes. Filter papers 312 impregnated with $CuSO_4$ (e.g., Whatman, Qualitative, ϕ90 mm, 160 µm thick) may also be shaped using the $CO_2$ laser 310 into corresponding squares as electrolytes overlap the copper electrodes, as are papers 314 impregnated with KCl patterned as salt-bridges and the electrolytes for the zinc electrodes. Thereafter, a polyimide/Kapton tape 316 (or a similar material) may be machined by the $CO_2$ laser 310 (or a similar modality). The small openings 318 are laser cut on the polyimide tape 316 and Zn tape 306 as access holes for urine/liquid activation of the battery 130 (see FIG. 6a). The battery 130 is assembled through aligning and taping these patterned layers, with the packaging strengthened by high temperature lamination. In operation, when liquid (e.g., urine) reaches the battery 130 and wets the filter papers 312, 314, a redox reaction initiates via the moist salt bridge connecting both half-cells, which activates the battery 130 and supplies power to the system 100.

Transport Path Unit

Now referring to the transport path unit 106 of the disposable device 60, the path unit 106 is a channel (microfluidic or otherwise) extending between and/or coupled with both the power source unit 104 and the sensing unit 102. The path unit 106 comprises at least one exposed open area 142 in the disposable device 60 configured for receiving liquid 402 therethrough and a transport path 144 comprising a channel that delivers received liquid 402 to the sensing strip 124 and the liquid-activated battery 130. In at least one embodiment, the upside of the open area 142 is exposed to the transport path 144. Furthermore, the open area 142 may be centered over all battery openings 318 such that when liquid 402 enters, it visits all of the battery openings 318 prior to arriving at the sensing strip inlet 124i in fluid communication with the transport path 144.

The transport path 144 is fixed, sealed by tapes, and designed such that any liquid 402 received therein reaches the liquid-activated battery 130 in the power source unit 104 prior to reaching the sensing strip 124 of the sensing unit 102. In this manner, when liquid 402 enters the system 100 through the at least one open area 142, the battery 130 activates the system 100 for data collection purposes prior to the sensing strip 124 receiving the liquid 402 therein. This delay allows for the system 100 to obtain at least two readings—an initial dry measurement of the output of the sensing unit 102 (i.e. before the liquid 402 reaches the sensing strip 124 via the transport path 144) and a wet, post-reaction measurement of the output of the sensing unit 102 when the liquid-absorbing sensing strip 124 is wet (i.e. after the liquid 402 has reached the sensing strip 124 and the reactants (liquid 402 and reagents) have developed to a stable point), which may be useful for comparison purposes or otherwise. Additionally, this delay may also be useful to record and evaluate a pre-reaction wet measurement, which can be used to evaluate the influence of the intrinsic urine color. While using only a dry measurement and a post-reaction, wet measurement would be sufficient to screen UTIs, including a pre-reaction, wet measurement further enhances the accuracy and precision of the results.

At least the geometric parameters of the transport path 144 may be tuned to ensure that the battery 130 is activated prior to the liquid 402 reacting with the reagents of the reagent strip 124r and optimize the flow of liquid 402 through the transport path 144 and/or liquid-absorbing sensing strip 124l. For example, in at least one embodiment, the leg of the transport path 144 that leads to the sensing strip 124 may be longer than the leg that leads to the battery 130 such that the absorbed liquid 402 has a farther distance to travel. Additionally or alternatively, a liquid-absorbing material (such as filter paper, for example) may be used to form or be positioned within some or all of the transport path 144 (e.g., along the sensing strip 124 leg) to slow the transfer of the liquid 402 therethrough as compared to the liquid transferred through the battery 130 leg of the transport path 144. Additionally, the porosity of such material may be manipulated to achieve the same goal.

Figure 5A:
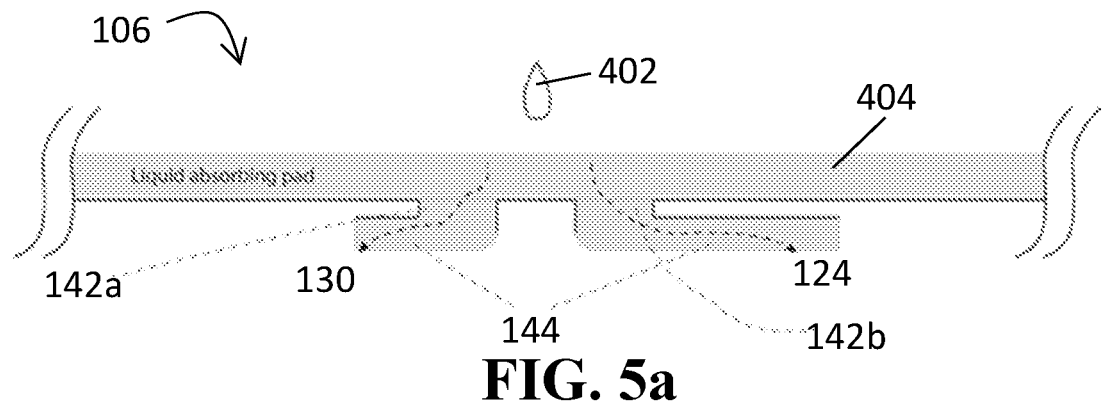
FIGS. 5a and 5b show cross-sectional views of a path unit 106 of the detection system of the present disclosure comprising a single transport path.
Figure 5B:
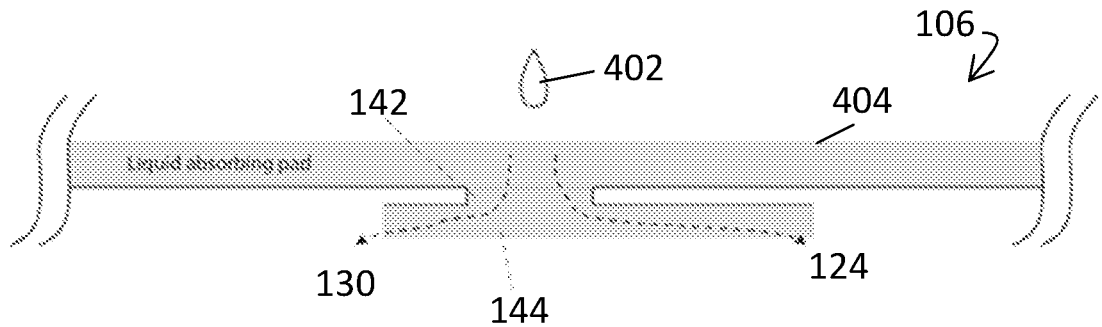

In at least one alternative embodiment and as shown in FIGS. 5a and 5b, the path unit 106 may further comprise an absorptive pad 404 comprising filter paper or the like. The absorptive pad 404 is positioned over/on top of the open area 142 of the system 100 such that liquid 402 absorbs therethrough prior to moving into the transport path 144. In such embodiments, the pad 404 functions to absorb the liquid 402 entering the system 100 through the open area 142 and distribute such liquid 402 to the battery 130 and the sensing strip 124. As shown in FIG. 5a, the use of an absorptive pad 404 may be beneficial where separate open areas 142 are employed for the battery 130 (open area 142a) and the sensing strip 124 (open area 142b) to ensure the battery 130 is activated prior to the liquid reaction with the reagent(s) of the sensing strip 124. In other embodiments, the pad 404 may only be positioned over open area 142b so that liquid 402 must flow therethrough to enter the transport path 144 to the sensing strip 124, but need not traverse the pad 404 to reach open area 142a to the battery 130. Alternatively, a single open area 142 may be used to connect to both the battery 130 and sensing strip 124 as shown in FIG. 5b. In the embodiments of both FIGS. 5a and 5b, the desired the dimensions, parameters, and/or absorptive properties of the pad 404 may be manipulated to achieve the desired delay in activation between the battery 130 and the sensing strip 124.

Liquid Transport Routes

FIGS. 5c-6c elucidate various embodiments of the liquid transport route within the disposable device 60 from top (FIG. 5c), perspective (FIG. 5d) and cross-sectional (FIGS. 6a-6c) views. As previously noted, the components of the disposable device 60 are integrated together and positioned within an outer covering of flexible substrate 201 and/or polyimide/Kapton tape 316 (or similar materials) to provide an external barrier therearound. In at least one embodiment, barrier surrounds the components of the disposable device 60, except for the open areas 142 (as described in further detail below). Hermetic sealing may also be employed, and the overall design of the disposable device 60 may be configured for comfort and/or to be unobtrusive when positioned within a diaper 10.

While the external barrier may, in at least one embodiment, comprise a hydrophobic barrier, the barrier need not necessarily be hydrophobic. In certain embodiments, the barrier need only comprise materials capable of providing a water-proof barrier to prevent liquid (i.e. urine) from disturbing the underlying device 60 components and, it will be appreciated that even somewhat hydrophilic materials can achieve this end. Accordingly, the external barrier prevents liquid from entering the interior of the disposable device 60 except through the one or more open areas 142.

The tape 316 defines the one or more open areas 142 of the path unit 106 and (optionally) provides an opening where the absorptive pad 404 may be positioned. The size and shape of the one or more open areas 142 are designed to facilitate ease of absorption of a liquid 402 into the system 100. Furthermore, the sensing strip 124 is packaged by at least one hydrophobic seal 601, which protects the sensing strip 124 from premature wetting such so battery 130 activation can occur first and various measurements can be recorded (dry, pre-reaction wet, and post-reaction wet). The hydrophobic seal 601 may be comprised of the same material as tape 316 and/or be formed by the tape 316 itself.

At least the light source 120 and photodetectors 122 are coupled with the substrate 201 of the sensing unit 102. In at least one embodiment, the substrate 201 also extends the length of the system 100 (either continuously or in an intermittent fashion) and provide a base for the battery 130 (see FIG. 6a). FIG. 6c shows a close-up, cross-sectional view of the power source unit 104 and the path unit 106 taken along line A-a of FIG. 6a, with the transfer path 144 coupling with the sensing strip 124 in a plane other than what is pictured (tape 316 is shown sealing the end of the transfer path 144 and seated on a substrate base 201. There, the tape 316 defines one or more openings 318 of the battery 130 as previously described with the power source unit 104.

Figure 6D:
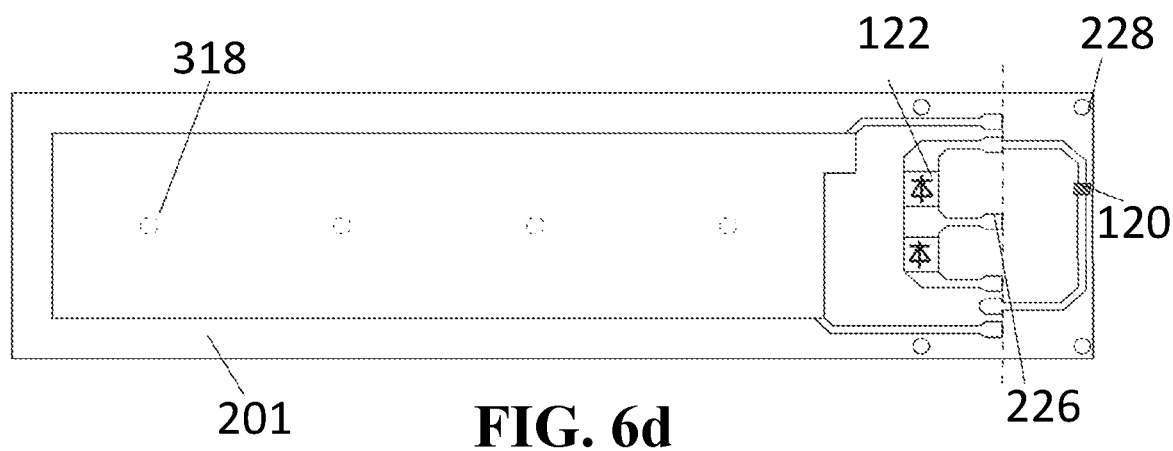
Figure 6E:
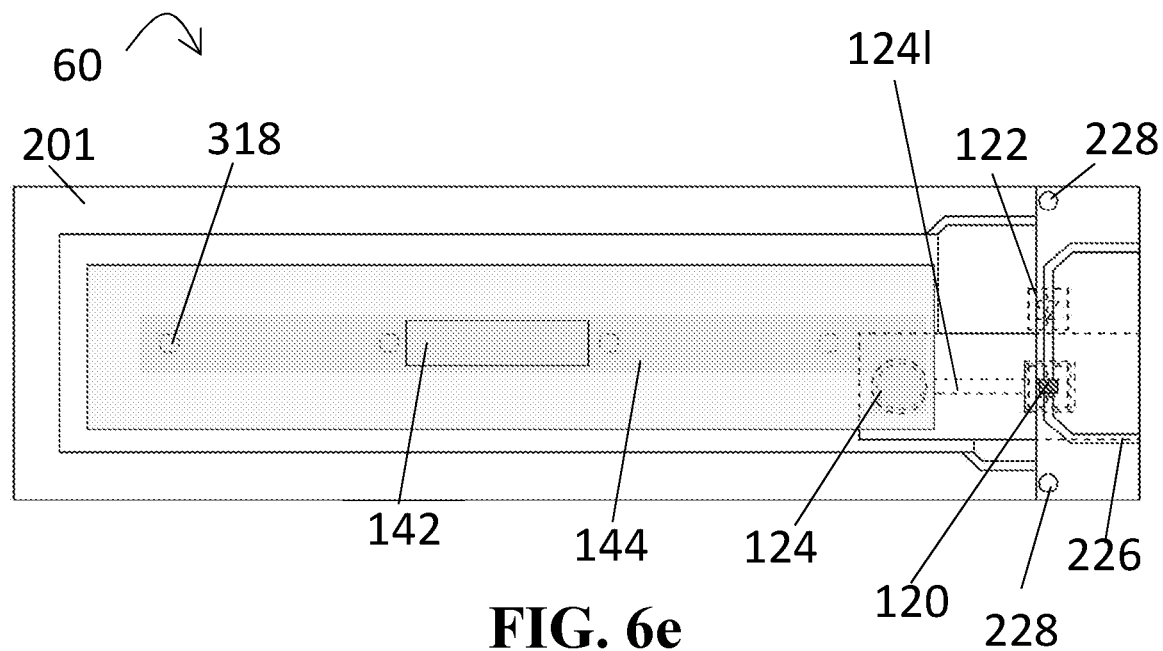
FIG. 6e shows a top view of the disposable device and detection system of FIG. 6d, illustrating the layers of components present throughout the device.

In at least one alternative embodiment, the substrate 201 may be positioned between the battery 130 and the path unit 106 as shown in FIGS. 6b, 6d, and 6e. In such embodiments, the substrate 201 defines one or more openings 618 that provide fluid access to the interior of the battery 130 (comparable to the openings 318 formed by tape 316 in other embodiments). Accordingly, the openings 618, the sensing strip inlet 124i, and the open area(s) 142 are exposed on the back side of the substrate 201 as shown in FIG. 6d. In this implementation, the sensing strip inlet 124i and the associated reagent strip 124r/detection region are on the same plane, which eases the assembly procedure of the system 100 as the sensing strip 124 does not pass through an opening 228 as in FIG. 6a.

Now referring to FIGS. 7a and 7b, at least one alternative embodiment of the path unit 106 of the system 100 is shown in a top view (FIG. 7a) and a perspective view (FIG. 7b). Here, the path unit 106 comprises a first transport path 744a and a second transport path 744b. Additionally, the open area 142 may comprise first open area 742a and second open area 742b (however it will be appreciated that the open area 142 may comprise only a single open area that provides access to multiple transport paths, if desired). Where multiple open areas 142 are employed, the first and second open areas 742a, 742b are configured as described in connection with open area 142, except that first open area 742a is in fluid communication with the first transport path 744a and the second open area 742b is in fluid communication with the second transport path 744b. Likewise, the first and second transport paths 744a, 744b are configured as previously described in connection with transport path 144 (and/or transport paths 142a, 142b of FIG. 5a); however, in this embodiment, the first transport path 744a leads to the battery 130 of the system 100 and the second transport path 744b leads to the sensing unit 102.

The two transport paths 744a, 744b are positioned adjacent to each other so that when liquid 402 reaches the opening 142, both paths 744a, 744b get wet at the same time. As previously described, the length, width, and various other parameters of the second transport path 744b and/or the liquid-absorbing strip 124l of the sensing strip 124 can be adjusted such that liquid 402 activates the battery 130 before the liquid 402 arrives at the reagent strip 124r portion(s) of the sensing strip 124.

Figure 8A:
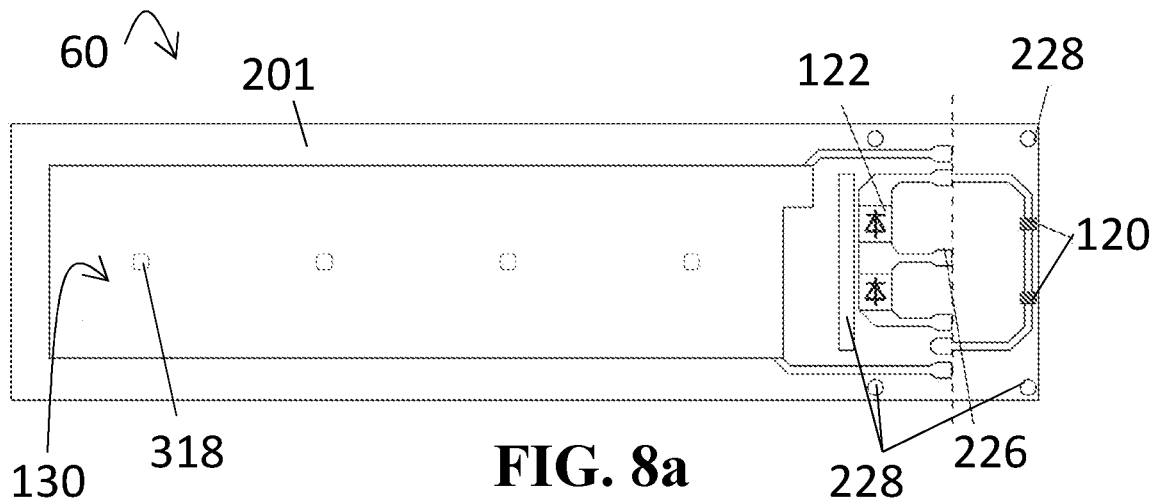
FIGS. 8a-8c show a sensing unit of the system of the present disclosure comprising two light sources.
Figure 8B:
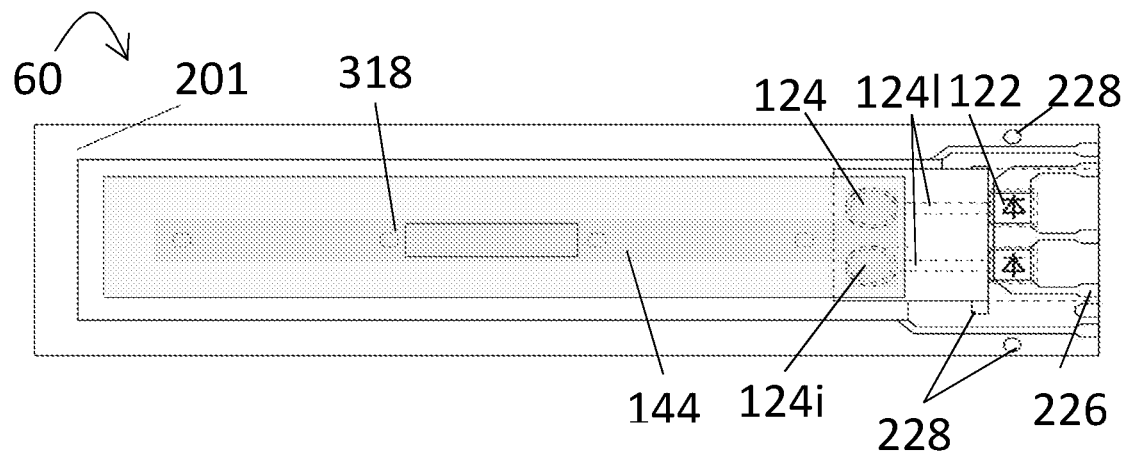
Figure 8C:
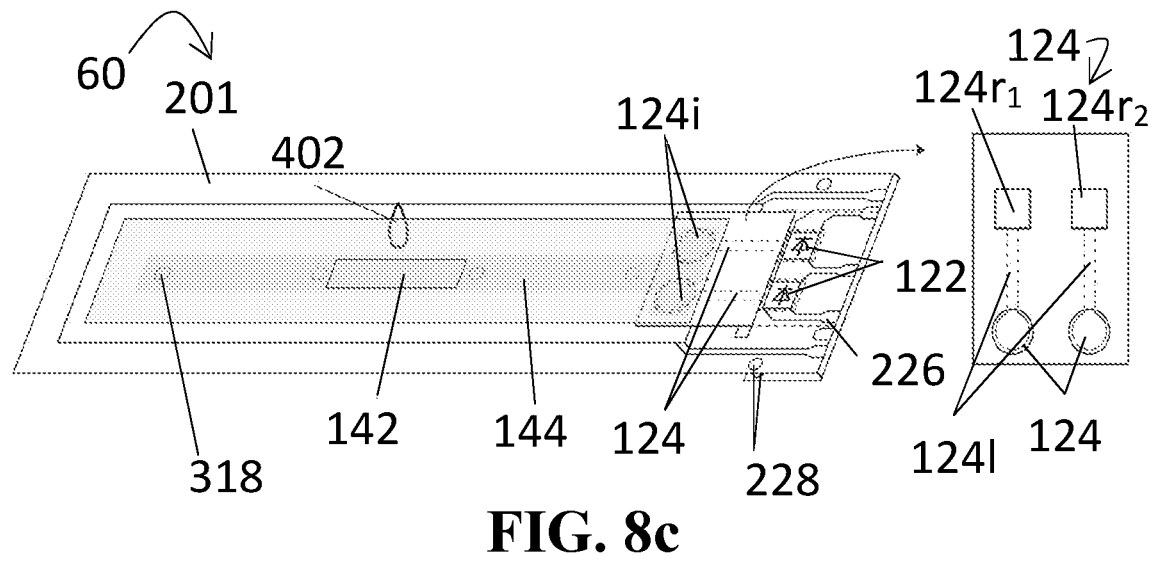

FIGS. 8a-8c illustrate at least one alternative multisensory embodiment of the sensing unit 102. In at least one embodiment, the sensing unit 102 may comprise at two light sources 120, two photodetectors 122 and two sensing strips 124 in fluid communication with a single transfer path 144 of the path unit 106. In at least one embodiment, one of the sensing strips 124 comprises a first reagent strip $124r_1$ comprising UTI (e.g., nitrite or nitrate)-sensing chemicals/reagents, while the other sensing strip 124 comprises a second reagent strip $124r_2$ that does not comprise UTI-sensing chemicals/reagents. In such cases, the sensing strip 124 without the chemicals/reagents ($124r_2$) can be used to provide a signal associated with the liquid 402 wetting the sensing strip 124 regardless of any potential colorimetric reaction from UTI surrogates (e.g., nitrite and/or nitrate), which can help reduce the influence from any intrinsic color associated with the liquid 402. Alternatively, the sensing strip 124 comprising the second reagent strip 124r2 may comprise a second reagent to detect a second parameter as previously described to further a diagnosis.

Sensor Signal Processing Unit

In addition to the disposable device 60, the detection system 100 also comprises reusable device 70 comprising electrical componentry. This device 70 is designed to be removably coupled with the exterior of the diaper 10 (and/or in another location) and is configured for reuse. In at least one embodiment, the reusable device 70 comprises at least the sensor signal processing unit 108, the power stage 132 (as previously described), and the data transmission unit 110.

To convert the light intensity signal(s) produced by the sensing unit 102 into an electrical signal using only the limited amount of energy available from the power source unit 104 when a liquid-activated battery 130 is employed, the detection system 100 further comprises a sensor interface—namely, the sensor signal processing unit 108. The sensor signal processing unit 108 comprises a sensor interface circuit 150 in operative communication with a microprocessor 152 and may employ a novel, simplified, semi-digital pulse width modulation ("PWM")-based design that significantly reduces the circuit complexity and power consumption, which his attractive for self-powered applications with a limited power budget. The binary two level nature of the PWM sensor interface output is also attractive for wireless transmission over a noisy environment. Alternatively, different types of sensor interface circuits 150—such as transimpedance amplifier ("TIA")—can be used instead of a PWM to convert current into voltage. Notably, where TIA and/or other designs are utilized an analog-to-digital converter ("ADC") may also be used to provide digital data representative of the voltage.

Where a PWM is used in connection with the sensor interface circuit 150, the pulse width of the binary output signal (received from the sensing unit 102) is inversely proportional to the photodiode current, and a digital counter configured to convert the pulse width into a digital signal. Due to its binary nature, the pulse width modulated signal is less sensitive to the supply voltage noise. Additionally, it also provides a wide dynamic range because the data is represented in the time domain measuring pulse width, rather than the voltage or current domain where its dynamic range is limited by the supply voltage. The architecture of the sensor signal processing unit 108 utilizing pulse width to digital conversion significantly improves the power efficiency and allows for the elimination of the complex and power-intensive TIA and ADC of conventional systems. Furthermore, the microprocessor 152 may also be employed as a (and optionally in lieu of) computing unit 112, if desired.

Figure 9A:
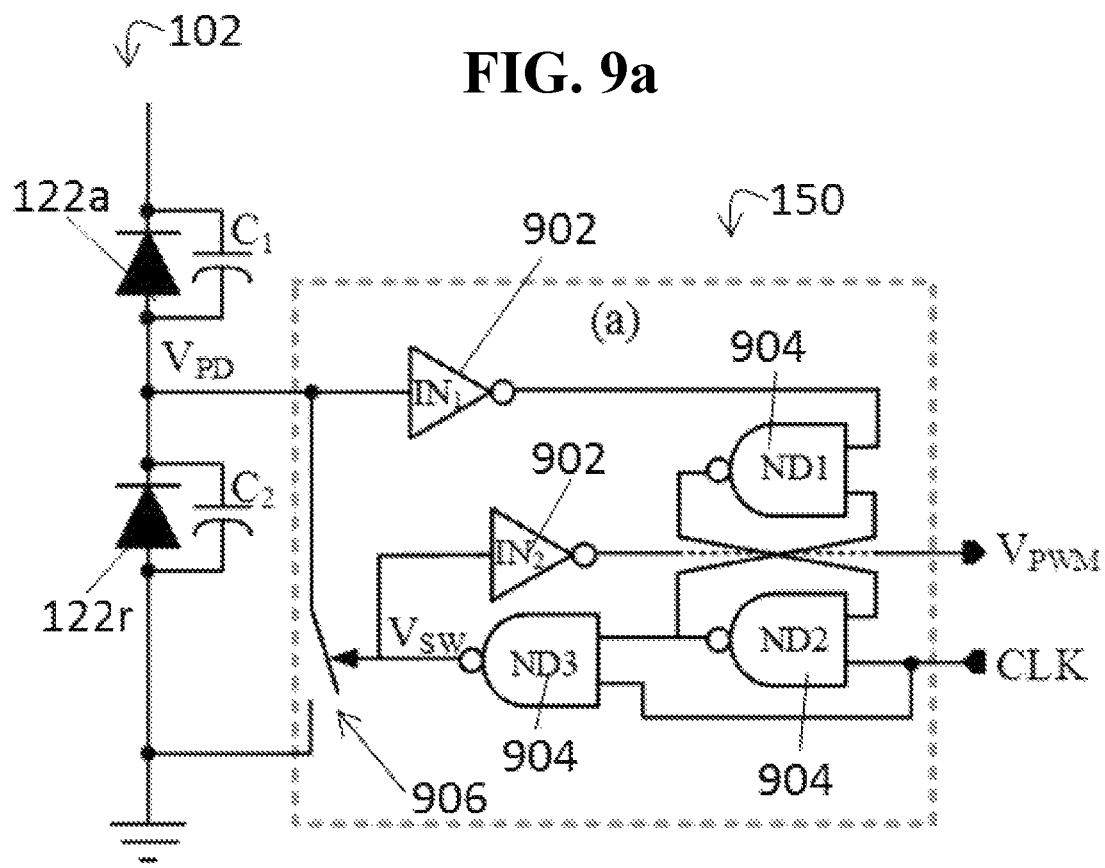
FIGS. 9a and 9b show a block diagram of a sensor interface circuit configuration (labeled (a)) according to an exemplary embodiment of the present disclosure and a timing diagram for the sensor interface circuit, respectively.
Figure 9B:
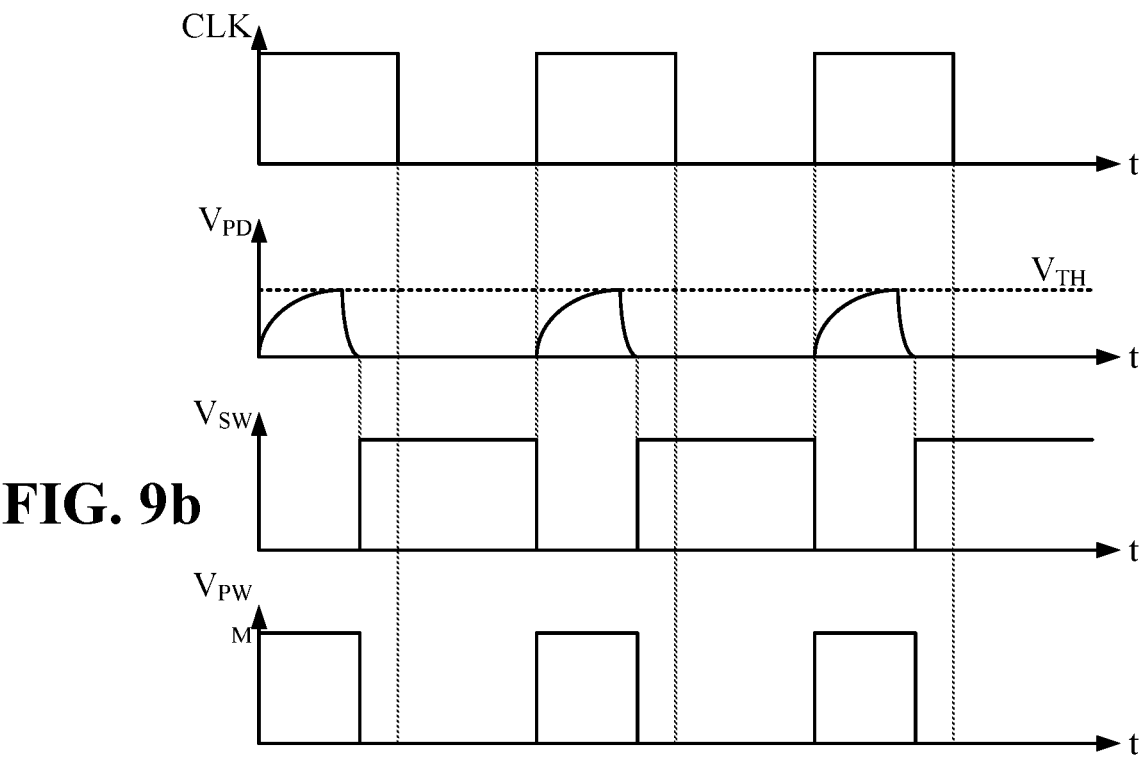

FIG. 9a shows a block diagram of at least one embodiment of a photodetectors 122 of the sensing unit 102 and a sensor interface circuit 150 configuration. Here, the sensor interface circuit 150 comprises two inverters 902, three NAND gates 904, and one analog (reset) switch 906. Two parasitic capacitors, $C_1$ and $C_2$, which are part of the two photodetectors 122a, 122r of the sensing unit 102, each have parasitic capacitance and, in this embodiment, act as a charging capacitor. FIG. 9b shows the signal response of the sensor interface circuit 150 operation at different stages (i.e. dry; wet, pre-reaction; wet, post-reaction). First, the active-high $V_{SW}$ signal changes from HIGH to LOW at the rising edge of the CLK signal coming from the data transmission unit 110 and turns the switch 906 off. The photocurrent ($I_{PD}$) initiates the charging of the node $V_{PD}$ positioned between the two photodetectors 122a, 122r and the $V_{PD}$ signal begins to increase. Once the $V_{PD}$ signal reaches a first inverter 902 (IN$_1$) threshold voltage, $V_{TH}$, which is a fraction of the supply voltage (e.g., $\alpha VDD$, where $\alpha$ is a constant smaller than 1), the first inverter 902 output pushes the $V_{SW}$ signal to HIGH, resetting the $V_{PD}$ signal to the ground. The $V_{PWM}$ signal is the inverse of the $V_{SW}$ signal.

Assuming that the parasitic capacitances are constant during the charging with the photocurrent $I_{PD}$, the relationship between the pulse width $T_{PW}$ of the $V_{PWM}$ signal and the photocurrent $I_{PD}$ can be analyzed as:

$$T_{PW} = \frac{(C_1 + C_2) \times \alpha VDD}{I_{PD}} \tag{1}$$

Figure 9C:
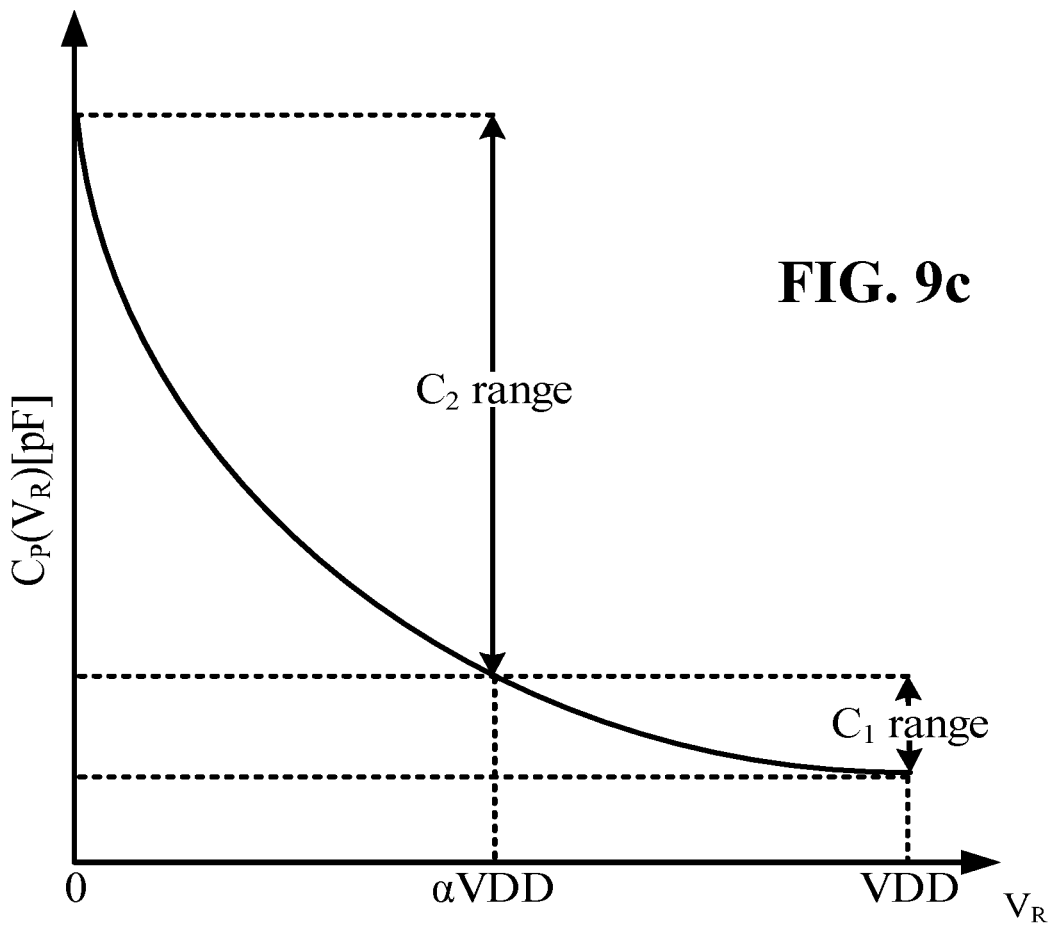
FIG. 9c shows a parasitic capacitance of a photodetector versus reverse bias voltage.

The parasitic capacitances, however, vary significantly during the charging process due to the dependency on its reverse bias voltage as illustrated in FIG. 9c. To obtain the pulse width $T_{PW}$ with voltage dependent capacitors, an abrupt pn-junction capacitance model and express the parasitic capacitance $C_P$ dependent on the reverse bias voltage were used as follows:

$$C_P(V_R) = \frac{\varepsilon_{SI}\varepsilon_0 A}{\sqrt{2\varepsilon_{SI}\varepsilon_0 A \mu \rho (V_R + \phi_{bi})}} \tag{2}$$

$$= \frac{K_0}{\sqrt{V_R + \phi_{bi}}}$$

$$\left(K_0 = \frac{\varepsilon_{SI}\varepsilon_0 A}{\sqrt{2\varepsilon_{SI}\varepsilon_0 A \mu \rho}}\right)$$

where $\varepsilon_{SI}$ is the silicon dielectric constant, $\varepsilon_0$ is the permittivity of free space, $\mu$ is the mobility of the electrons, $\rho$ is the resistivity of the silicon, $V_R$ is the applied reverse bias voltage, $\phi_{bi}$ is the built-injunction voltage, and A is the diffused area of the junction.

Figure 9D:
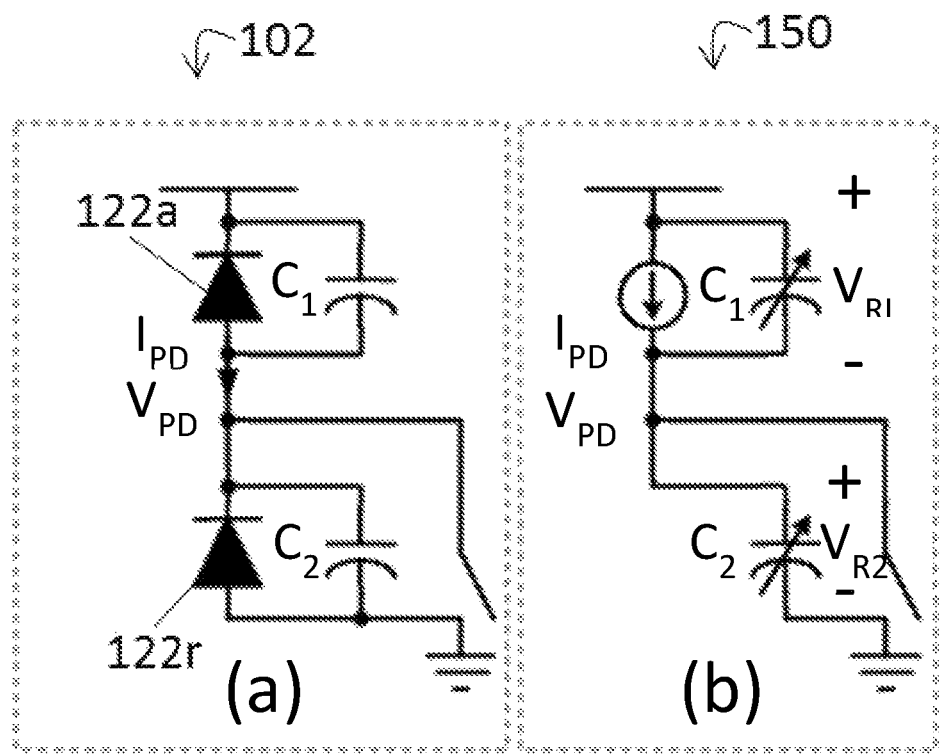
FIG. 9d shows active and reference photodetectors with parasitic capacitors (subpart (a)) and a circuit model with the voltage dependent parasitic capacitors (subpart (b))

FIG. 9d shows the circuit model of the two variable parasitic capacitors. To calculate $T_{PW}$, we add the contributions of each parasitic capacitor of the two photodiodes. From subpart (b) of FIG. 9d, the parasitic capacitance $C_1$ of the active photodiode can be described as $$C_1(V_{R1}) = C_P(VDD - V_{PD}) \tag{3}$$

where $V_{R1} = VDD - V_{PD}$.

In addition, the parasitic capacitance $C_2$ of the reference photodiode can be given as $$C_2(V_{R2}) = C_P(V_{PD}) \tag{4}$$

where $V_{R2} = V_{PD}$.

Using Equations (3) and (4), we can calculate $$I_{PD} = [C_P(VDD - V_{PD}) + C_P(V_{PD})]\frac{dV_{PD}}{dt} \tag{5}$$

Performing an integral, the relation between the pulse width $T_{PW}$ and the photocurrent $I_{PD}$ can be described as follows:

$$T_{PW} = \frac{1}{I_{PD}}\int_0^{\alpha VDD} [C_P(VDD - V_{PD}) + C_P(V_{PD})] \cdot dV_{PD} \tag{6}$$

$$= \frac{\beta}{I_{PD}}$$

where $$\beta = K_0 \cdot \sqrt{VDD + \phi_{bi}} - \sqrt{(1-\alpha)VDD + \phi_{bi}} +$$

$$= \sqrt{\alpha VDD + \phi_{bi}} - \sqrt{\phi_{bi}}.$$

Equation (6) shows that the pulse width $T_{PW}$ of the $V_{PWM}$ signal is inversely proportional to the photocurrent $I_{PD}$, even with the voltage dependent parasitic capacitances.

Various sources of noises exist the sensing unit 102 and sensor signal processing unit 108. The main noise sources that can potentially limit the performance of the sensing unit 102 are in the photodetectors 122 and the sensor interface circuits 150 (e.g., shot noise in the photodetectors 122, thermal noise of the constituent devices in the sensor interface circuits 150, and the random fluctuation of the power supply VDD). These noises can introduce jitter in the edges of the output $V_{PWM}$ signal. Assuming a white Gaussian random distribution, the root mean square (RMS) jitter and the standard deviation of jitter, $\sigma_T$, can be expressed as Jitter$_{rms}$=$\sigma_T$ and the noise $\mu_N$ can be defined as $\mu_N \sim N(0, \sigma^2_{V \text{ or } I})$, with a standard deviation $\sigma_V$ as the voltage or $\sigma_I$ as the current.

The rising edge of the $V_{PWM}$ signal is only affected by the noise from the inverter 902 and the NAND gate 904. The falling edge of the $V_{PWM}$ signal is affected by the noise from the photodetectors 122, the power source unit 102, the inverters 902, and the NAND gates 904. Since the inverter 902 and the NAND gate 904 carry digital signals with a high slew rate, the jitter generated by the inverter 902 and the NAND gate 904 is less significant. However, the noise voltage of the power source unit 102 and the noise current of the photodetectors 122 can significantly affect the $V_{PD}$ signal that changes slowly and determines the falling edge of $V_{PWM}$ signal. Consequently, more significant jitter may appear at the falling edges of the $V_{PWM}$ signal.

Figure 9E:
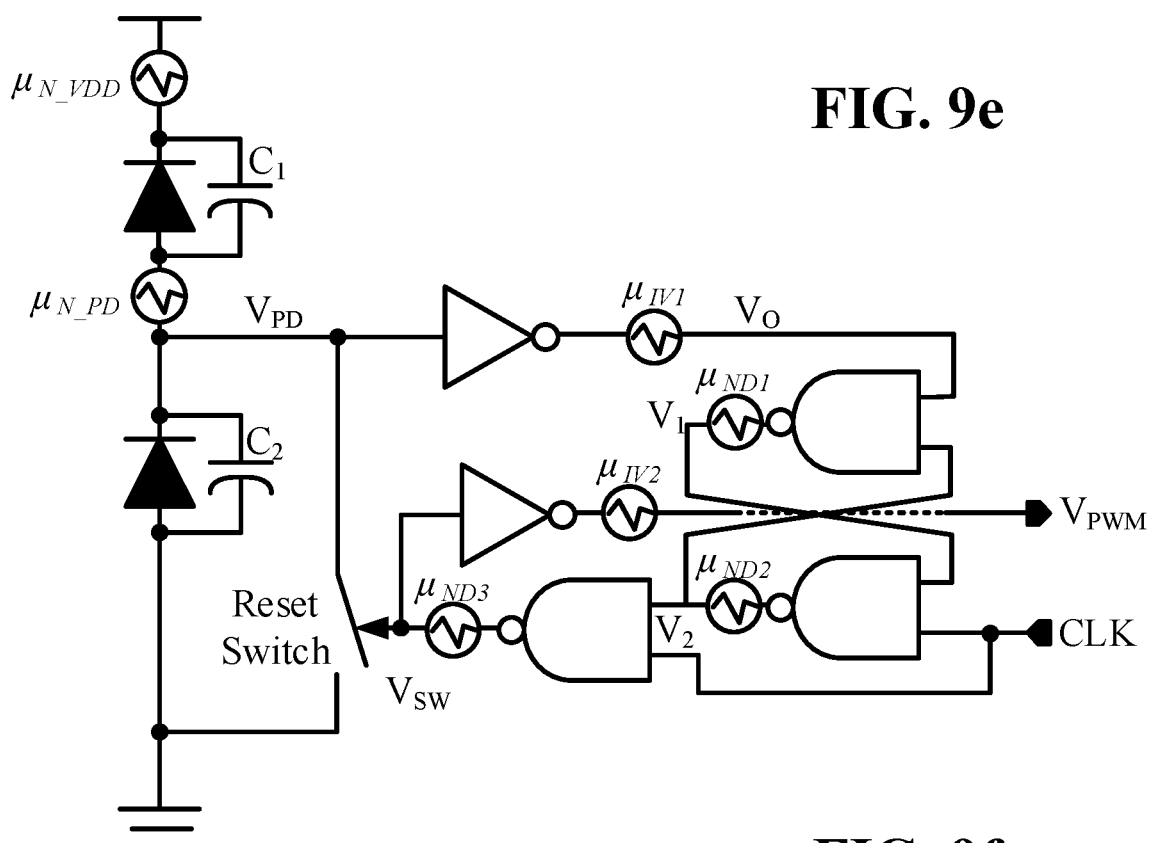
FIG. 9e shows a conceptual diagram of the noise sources of the system of the present disclosure.

The pulse width of the output signal is affected by the following noise sources as shown in FIG. 9e:

i. Noise voltage from VDD: $\mu_{N\_VDD} \sim N(0, \sigma^2_{N\_VDD})$.
ii. Noise current from the active photodiode: $u_{N\_PD} \sim N(0, \sigma^2_{N\_PD})$.
iii. Noise voltage from the inverters: $\mu_{N\_IV1} \sim N(0, \sigma^2_{N\_IV1})$, $\mu_{N\_IV2} \sim N(0, \sigma^2_{N\_IV2})$
iv. Noise voltage from the NAND gates: $\mu_{N\_ND1} \sim N(0, \sigma^2_{N\_ND1})$, $\mu_{N\_ND2} \sim N(0, \sigma^2_{N\_N\_D2})$, $\mu_{N\_ND3} \sim N(0, \sigma^2_{N\_N\_D3})$.

Figure 9F:
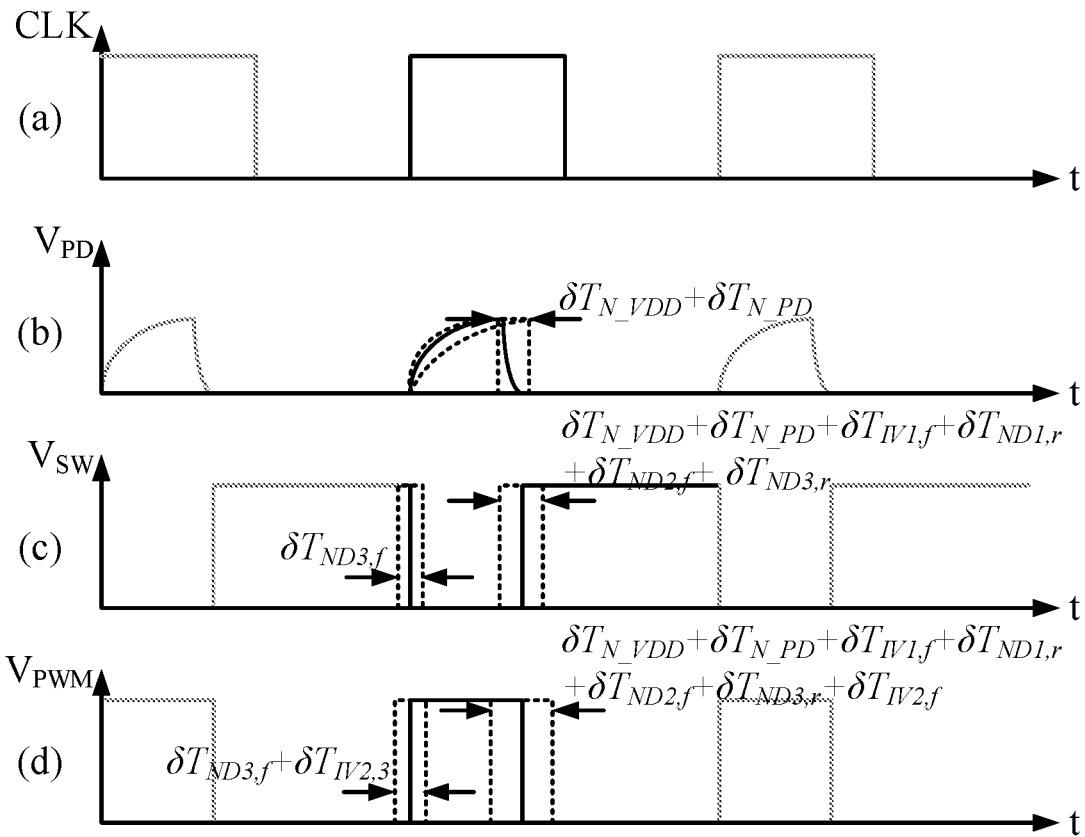
FIG. 9f shows a graphical representation of the effect of jitter at different stages, with (a) comprising a clock signal, (b) $V_{PD}$ signal at charging node, (c) $V_{SW}$ signal to control the analog switch, and (d) Output $V_{PWM}$ signal.

FIG. 9f depicts the effect of each noise source to each signal stage and the output $V_{PWM}$ signal. To find the jitter $\sigma_{T\_1st}$ on the output $V_{PWM}$ signal generated by the additive noise $\mu_{N\_PD}$, and $\mu_{N\_VDD}$, the additive noise current $\mu_{N\_PD}$, superimposed on the $V_{PD}$ signal, is primarily considered. The dominant noise in the active photodetector 122a is shot noise and can be modeled as the white Gaussian random noise process with a two-sided power spectral density (PSD), $S_{PD1}(f)$.

$$S_{PD1}(f) = qI_{PD} A^2/Hz \quad (7)$$

where q is the elementary charge of an electron. It can be expressed as $u_{N\_PD} \sim N(0, qI_{PD}\Delta f)$. In such a noisy environment, the $V_{PD}$ signal is the sum of a signal voltage $v_{pd}$ and a noise voltage $v_n$, i.e., $V_{PD} = V_{pd} + v_n$. Assuming the signal voltage is much larger than the noise voltage, the parasitic capacitances can be approximated as $C_1(VDD - V_{PD}) \approx C_p(VDD - v_{pd})$ and $C_2(V_{PD}) \approx C_p(VDD - v_{pd})$. With this approximation, the following can be obtained:

$$T_{PW} = \frac{1}{I_{PD} + u_{N\_PD}} \int_0^{\alpha VDD} [C_p(VDD - v_{pd}) + C_p(v_{pd})] \cdot dv_{pd} \quad (8)$$

$$= \frac{\beta}{I_{PD} + u_{N\_PD}}.$$

Assuming $y = I_{PD} + u_{N\_PD}$, the variance of jitter, $\sigma_{T\_PD}$, can be derived according to the variance of noise current, $qI_{PD}\Delta f$, as $$\sigma^2_{T\_PD} = Var[T_{PW}] \quad (9)$$

$$= \beta^2 \cdot Var\left[\frac{1}{I_{PD} + u_{N\_PD}}\right]$$

$$= \beta^2 \cdot \left\{ \int_{-\infty}^{\infty} \frac{1}{y^2} \cdot \frac{1}{\sqrt{2\pi qI_{PD}\Delta f}} \cdot e^{-(y-I_{PD})^2/2qI_{PD}\Delta f} dy - \left[\int_{-\infty}^{\infty} \frac{1}{y} \cdot \frac{1}{\sqrt{2\pi qI_{PD}\Delta f}} \cdot e^{-(y-I_{PD})^2/2qI_{PD}\Delta f} dy\right]^2 \right\}$$

In addition, $\sigma_T$ can be approximately expressed using Equation (10):

$$\sigma_T = \frac{\sigma_V}{SR} \quad (10)$$

where SR is the slew rate of the signal. Because the $V_{PD}$ signal is not linear, the slope of the $V_{PD}$ signal is calculated when the $V_{PD}$ signal reaches $\alpha VDD$ as follows:

$$\left.\frac{dV_{PD}}{dt}\right|_{V_{PD}@\alpha VDD} = \left.\frac{I_{PD}}{C_p(VDD - V_{PD}) + C_p(V_{PD})}\right|_{V_{PD}@\alpha VDD} \quad (11)$$

$$= \gamma \cdot I_{PD}$$

$$\left(\gamma = \frac{\left(\sqrt{(1-\alpha)VDD + \phi_{bi}} + \sqrt{\alpha VDD + \phi_{bi}}\right)}{K}\right)$$

Using Equations (8), (9), and (10), the jitter $\sigma_{T\_1st}$ can be obtained as $$\sigma_{T\_1st} = \sqrt{\sigma^2_{T\_PD} + \left(\frac{\sigma_{N\_VDD}}{\gamma I_{PD}}\right)^2} \quad (12)$$

$$= (\delta T_{N\_PD} + \delta T_{N\_VDD})_{rms}$$

Due to the slow change in the $V_{PD}$ signal, the $\sigma_{T\_1st}$ becomes the main jitter that is inversely proportional to the photodetector 122 current.

The jitter added onto the $V_{PWM}$ by the inverters are $$(\delta T_{IV1})_{rms} = \frac{\sigma_{IV1}}{SR_{IV}} \quad (13)$$

$$(\delta T_{IV2,r})_{rms} = \frac{\sigma_{IV2,r}}{SR_{IV}}; (\delta T_{IV2,f})_{rms} = \frac{\sigma_{IV2,f}}{SR_{IV}} \quad (14)$$

where $SR_{IV}$ is the slew rate at the output of the inverter 902.

The jitter introduced by the NAND gates 904 are $$(\delta T_{ND1,f})_{rms} = (\delta T_{ND3,f})_{rms} = \frac{\sigma_{ND1,f}}{SR_{ND}} \quad (16)$$

$$(\delta T_{ND2,r})_{rms} = (\delta T_{ND2,r})_{rms} = \frac{\sigma_{ND2,r}}{SR_{ND}} \quad (17)$$

where $SR_{ND}$ is the slew rate at the output of the NAND gate 904.

From Equations (11)-(17), it is significant that the rising edge jitter is smaller than the falling edge jitter and that the falling edge jitter is inversely proportional to the photodetector 122 current.

By adding the independent jitter sources, the time deviation from the ideal output pulse width of the $V_{PWM}$ signal can be calculated as $$\sigma_{T,total} = [(\delta T_{N\_VDD} + \delta T_{N\_PD})^2 + (\delta T_{IV1})^2 + (\delta T_{IV2,r})^2 + (\delta T_{IV2,f})^2 + 2(\delta T_{ND1,f})^2 + 2(\delta T_{ND2,f})^2]^{1/2} \quad (18)$$

Using the total jitter $\sigma_{T,total}$ and by differentiating Equation (6), the photodetector 122 current resolution $I_{PD,res}$ can be calculated as $$I_{PD,res} = \left| \sigma_{T,total} \cdot \frac{I_{PD}^2}{\beta} \right|_{@Maximum I_{PD}} \quad (19)$$

where the nitrite concentration of 0 mg/L provides the maximum photodetector 122 current. Equation (19) shows that photodetector 122 current resolution $I_{PD,res}$ can be improved by either reducing the photodetector 122 current $I_{PD}$ or the jitter $\sigma_{T,total}$. However, the photodetector 122 current $I_{PD}$ determines the detection range of the sensing unit 102; therefore, to achieve increased photodetector 122 current resolution $I_{PD,res}$, reduction of the jitter $\sigma_{T,total}$ is a better option. One of the sources of jitter $\sigma_{T,total}$ is the shot noise of the photodetector 122, which is white and can be reduced by averaging samples. In at least one embodiment of the detection system 100, a photodetector 122 resolution of 30 nA may be required for a targeted nitrite concentration detection sensitivity, 1.35 ms/(mg/L). Without averaging, the photodetector 122 resolution of the system 100 may be at or about 117 nA, which does not meet the target. The target resolution was achieved by averaging over 100 consecutive pulse width data.

Figures 3C, 3D:
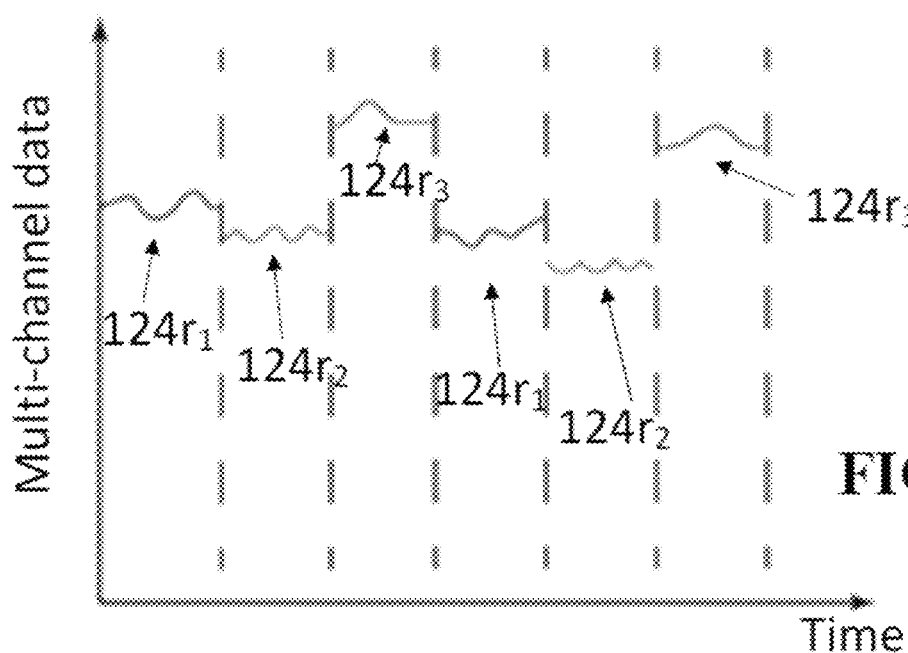
FIG. 3c shows a table depicting sensitivity and specificity values of various dipstick urinalysis markers/substances used to conventionally detect UTI.
FIG. 3d shows a graph depicting decoded multichannel data collected by the sensing strip of FIG. 3b.

As previously stated, while a specific configuration and componentry are used to describe the sensor signal processing unit 108 and the components thereof, such description is not intended to be limiting and any suitable configuration and/or components may be employed to achieve the desired functionality as is known in the art and/or hereinafter developed. For example, as shown in FIGS. 3b and 3d in connection with the multisensory embodiments of the sensing unit 102 described herein, the sensor signal processing unit 108 may further comprise a multiplexer 160 communicatively connected to the microprocessor 152, the power source unit 104 (and/or the battery 130 thereof), and the sensing unit 102. Perhaps more specifically, the multiplexer 160 may be individually connected to each unit of the sensing unit 102 comprising a light source(s) 120, photodetector(s) 122, and a particular reagent strip $124r_n$ (each a "detection unit $123_n$"). In at least one embodiment, the multiplexer 160 is connected to each detection unit $123_n$ via a wired connection comprising two wires—one for power input from the multiplexer 160 to the detection unit $123_n$ and one for signal output from the detection unit $123_n$ to the multiplexer 160.

The multiplexer 160 is controlled by the microprocessor 152 such that, in operation, the multiplexer 160 periodically switches the channel of the sensor signal processing unit 108 to power a specific detection unit $123_n$ and obtain its signal output (light intensity signals produced by the respective detection unit $123_n$/reagent strip $124r_n$) at the same time. Accordingly, each channel corresponds to a specific reagent strip $124r$ such that it is indicative of a particular reagent, disease biomarker or diagnostic test. For example, the multiplexer 160 of FIG. 3b will power/receive an output signal from detection unit $123_1$, then power/receive an output signal from detection unit $123_2$, then power/receive an output signal from detection unit $123_3$. The detection unit $123_{1, 2, 3 \ldots n}$ output signals are combined multichannel signal, which is then decoded by the microprocessor 152 (or other computing unit) based on the known timing protocol that was used to encode the multichannel signal (see FIG. 3d). For example, in at least one embodiment, the known timing protocol may comprise the following: if within a period $T = t_1 + t_2 + t_3$, then $0 \sim t_1$ is when channel 1 is on (powered and transmitting output signals to the multiplexer 160) while $t_2$ and $t_3$ are off (not powered or transmitting signals to the multiplexer 160). Likewise $t_1 \sim t_1 + t_2$ is when only channel 2 is on and $t_1 + t_2 \sim t_1 + t_2 + t_3$ is channel 3 duration (this protocol being known and programmed into the microprocessor 152 or the like). In such cases then decoding comprises taking the spanning $0 \sim t_1$ out of each single period T for channel 1, $t_1 \sim t_1 + t_2$ for channel 2, and so on, which is akin to down-sampling the signal of a channel if only that channel is on throughout the measurement activity.

Data Transmission Unit

In addition to the sensor signal processing unit 108, the reusable device 70 further comprises a data transmission unit 110 and, optionally, a computing unit 112 (certain embodiments of the system 100 may utilize the microprocessor 152 to perform the computing unit 112 functionality described herein). The data transmission unit 110 is operable to transmit the processed data from the sensor signal processing unit 108 to the computing unit 112 through a wireless or wired channel (such as network 1010) using modalities known in the art or hereinafter developed (for example, and without limitation, Bluetooth (via a Bluetooth low energy (BLE) link or otherwise), WiFi, etc. In at least one embodiment, the data transmission unit 110 is communicatively connected to the computing unit 112 via network 1010 (described below).

Figure 10:
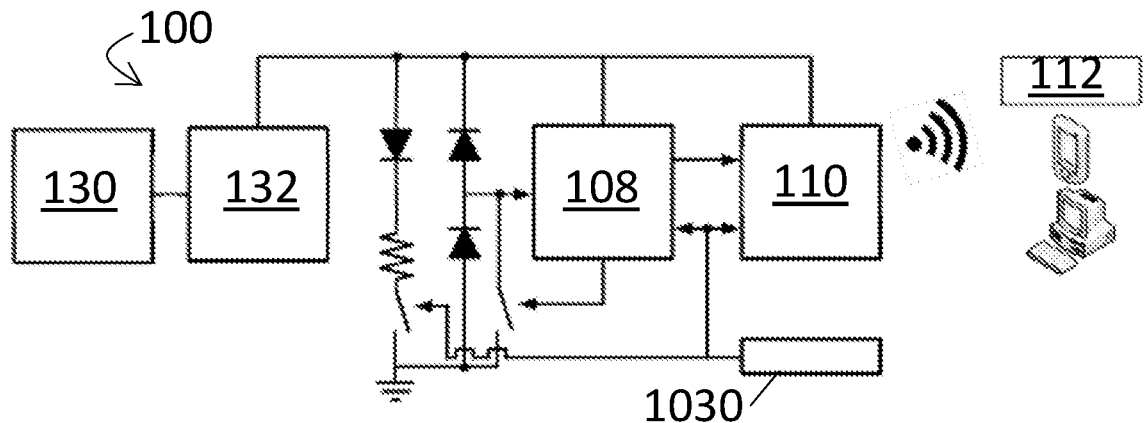
FIG. 10 shows an exemplary embodiment of the detection system of the present disclosure comprising a clock source.

Referring to FIG. 10, in at least one embodiment of the detection system, the data transmission unit 110 further comprises and/or is communicatively connected to an external clock source and/or a microcontroller for generating a clock signal (collectively, the "clock source 1030"). Additionally, a signal from the clock source 1030 feeds into the sensor signal processing unit 108 and, perhaps more specifically, the sensor interface circuit 150 and microprocessor 152 thereof. The clock source 1030 is beneficial for operation of the sensor unit 102, as well as power management applications as described in additional detail herein.

Computing Unit

The computing unit 112 is operable to analyze the data received from the data transmission unit 110 and compute at least the concentration of the targeted ion/compound present within the liquid 402. For example, the computing unit 112 is operable to automatically analyze data received from the sensor signal processing unit 108 (via the data transmission unit 110), compute a nitrate and/or nitrite concentration within the liquid/urine 402, and (optionally) provide a notification if such concentration level(s) fall outside of a pre-defined parameter range. In this manner, the detection system 100 provides a wireless and autonomous UTI detection system that allows for the early detection and screening of UTIs with minimally invasive efforts.

Figure 11:
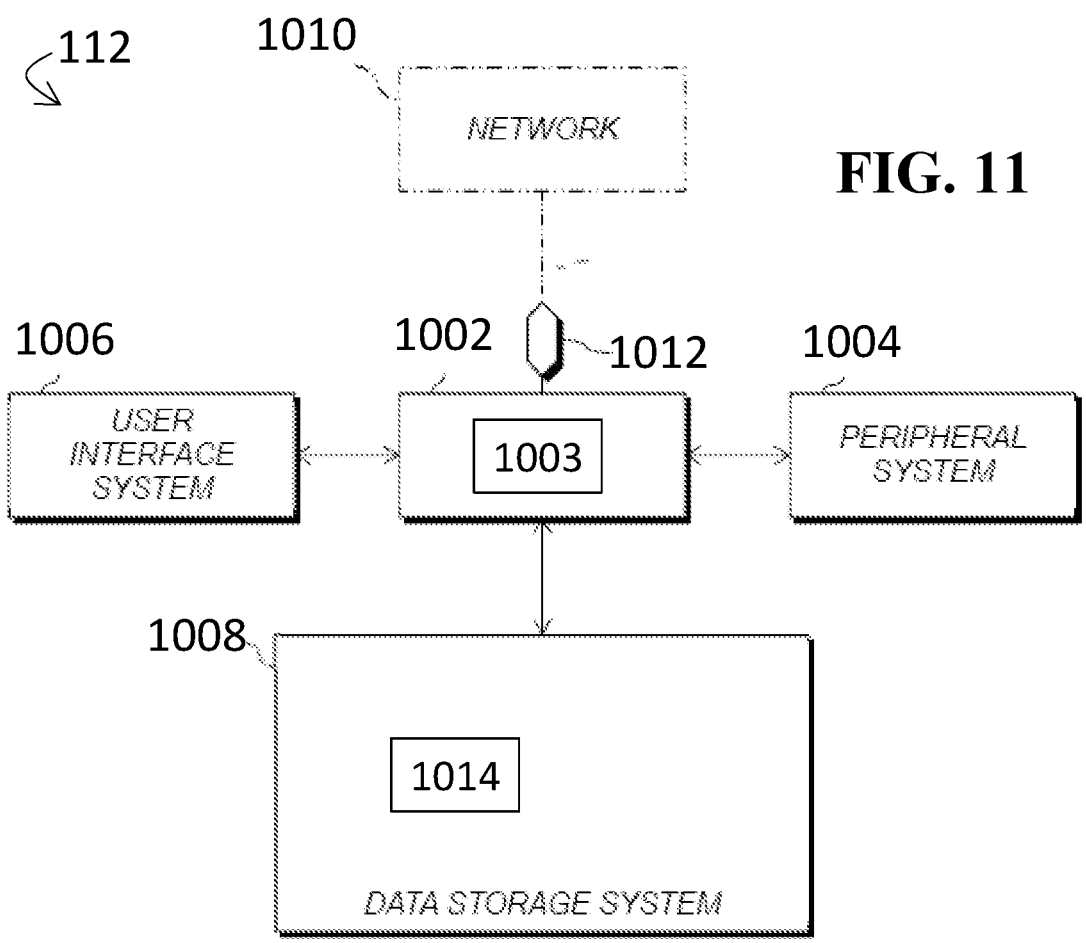
FIG. 11 displays a high-level diagram showing the components and subsystems of an exemplary computing unit for analyzing data and performing the methods hereof according to an exemplary embodiment of the present disclosure.

Referring to FIG. 11, a high-level diagram is provided showing at least one embodiment of various subsystems of the computing unit 112. Generally, the computing unit 112 may comprise one or more microprocessors, personal computers, programmable logic devices, digital signal processors, central processing units, microcontrollers, desktop computers, laptop computers, mainframe computers, personal digital assistants, server computers, cellular phone, smartphone, tablet, or any other device for displaying, processing, managing, or handling data whether implemented with electrical, magnetic, optical, biological components, or otherwise.

In at least one exemplary embodiment of the detection system 100, the computing unit 112 comprises a mobile device running one or more mobile applications. Such mobile applications may be configured for comprehensive and intuitive analysis of the data received from the data transmission unit 110, displaying the same in a user-friendly manner (via graphical user interfaces or otherwise), the execution of interactive communication modalities (such as text, email, instant messaging, and the like), and/or interfacing with one or more health related, third party platforms.

In at least one embodiment, the computing unit 112 comprises a data processing system 1002 for analyzing data and performing other functionality described herein (e.g., power saving operations). The data processing system 1002 comprises a processor 1003 and either additionally comprises or is communicatively connected with a peripheral system 1004, a user interface system 1006, a data storage system 1008, and/or a communication system 1012.

The data processing system 1002 can be communicatively connected to network 1010 (shown in phantom), which may comprise the Internet, an intranet, or any other type of network configuration or resource, through which the processor 1003 can communicate with other devices, systems, and databases. Additionally or alternatively, the data processing system 1002 may be communicatively connected to one or more of a peripheral system 1004, a user interface system 1006, a data storage system 1008, and/or a communication interface 1012 via the network 1010 or otherwise.

The devices and subsystems associated with the computing unit 112 (including the peripheral system 1004, the user interface system 1006, the data storage system 1008, and communication interface 1012) can be located in physical proximity with each other or not. For example, while subsystems 1004, 1006, 1008, and 1012 are shown separately from the data processing system 1002 in FIG. 11, they can be stored completely or partially within the processor 1003 and/or hardware associated with the computing unit 112 or, as is the case with at least one exemplary autonomous embodiment of the detection system 100, the computing unit 112 may be remote with respect to the disposable device 60. In at least one embodiment, processor 1003 can be or include the microprocessor 152 of the sensor signal processing unit 108. In such scenario, the detection system 100 need not comprise a separate computing unit 112 at all, but instead may rely on the microprocessor 152 to provide the functionality described herein.

The peripheral system 1004 can include one or more devices or modules configured to provide digital data to the processor 1003/data processing system 1002 of the computing unit 112. For example, the peripheral system 1004 can include microprocessor 152 of the sensor signal processing unit 108 or any other components of the system 100. The processor 1004, upon receipt of digital data from a device or module of the peripheral system 1004, can store such data in the data storage system 1008.

The user interface system 1006 can include a mouse, a keyboard, another computer (connected, for example, via the network 1010 or a null-modem cable), or any other device or combination of devices from which data is input into the processor 1003. The user interface system 1006 can also include a display device, a processor-accessible memory, or any device or combination of devices to which data is output by the processor 1004 and any related graphical user interfaces ("GUIs") through which a user may access the functionality of and/or interact with the detection system 100. The user interface system 1006 and the data storage system 1008 can, in at least one embodiment, share a processor-accessible memory.

Depending on the desired configuration and implementation of the user interface system 1006, a GUI may be local to the data processing system 1002, provided over the network 1010, or stored within the data storage system 1008. In at least one embodiment, the GUIs are available through a web-based portal that provides functionality for accessing and displaying data received by the data processing system 1002 and/or stored within the data storage system 1008. In at least one exemplary embodiment, the GUIs are part of a mobile application and/or widget designed to run on smartphones, tablet computers, wearables, and/or other mobile devices. In all cases, the GUIs are programmed to activate desired software routines and may provide application-specific instruments to a user using the on-screen representation of buttons, dials, toggles, fields, sliders, and/or the like.

In various aspects, the data processing system 1002 includes or is connected to a communication interface 1012 that is coupled with the network 1010. Communication interface 1012 sends and receives electrical, electromagnetic or optical signals that carry digital or analog data streams representing various types of information to network 1010 (via a network link or as is otherwise known in the art). The processor 1003 of the data processing system 1002 is configured to send messages and receive data, including program code and/or data from the data transmission unit 110 of the detection system 100, through network 1010 and communication interface 1012. For example, a server can store requested code for an application program directed to performing functionality of the detection system (e.g., a JAVA applet), which may comprise a software module, application, code, or the like, on a tangible non-volatile computer-readable storage medium to which it is connected. The server can retrieve the code from the medium and transmit it through network 1010 to communication interface 1012. The received code can be executed by processor 1003 as it is received, or stored in data storage system 1008 for later execution.

Data storage system 1008 can include or be communicatively connected with one or more processor-accessible memories configured to store data. The memories can be, for example, a chassis or as parts of a distributed system. The phrase "processor-accessible memory" includes any data storage device to or from which processor 1003 can transfer data (using appropriate components of peripheral system 1004 or otherwise), whether volatile or nonvolatile; removable or fixed; electronic, magnetic, optical, chemical, mechanical, or otherwise. Exemplary processor-accessible memories include but are not limited to: registers, floppy disks, removable media and/or removable drives, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 1008 can be a tangible non-transitory computer-readable storage medium, i.e., a non-transitory device or article of manufacture that participates in storing instructions that can be provided to processor 1003 for execution.

In an example, data storage system 1008 includes a computer usable medium/disk 1014, e.g., a tangible computer-readable rotational storage device such as a hard drive, and code memory 1016, e.g., a RAM. Computer program instructions (i.e. computer readable program code) are read into code memory 1016 from the computer usable medium 114. The computer readable program code may be for causing the computing unit 112/processor 1003 to, among other things, perform comprehensive and intuitive analysis of data received from the peripheral system 1004 (i.e. sensor signal processing unit 108 and/or data transmission unit 110), display such data in a user-friendly manner (via associated graphical user interfaces of the user interface system 1006 or otherwise), execute communication modalities (such as text, email, instant messaging, and the like using the communication interface 1012), and/or interface with one or more health related, third party platforms and/or databases. Such computer readable program code comprises code associated with each of the foregoing functions, as well as any other functionality that may be appropriate and/or desirable in connection with use of the detection system 100 (either from a patient or healthcare provider perspective).

Processor 1003 executes one or more sequences of the computer readable program code loaded into code memory 1016 and, as a result, causes performance of the method steps described herein. In this way, processor 1003 carries out a computer implemented process of methods 1200, 1600, and 1700. For example, steps of methods described herein, blocks of the flow-chart illustrations or block diagrams herein, and combinations of those, can be implemented by computer program instructions. Code memory 1016 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system." Furthermore, various aspects herein may be embodied as computer program products including computer readable program code stored on a tangible non-transitory computer readable medium. Such a medium can be manufactured as is conventional for such articles. The program code includes computer program instructions that can be loaded into processor 1003 (and possibly also other processors), to cause functions, acts, or operational steps of various aspects herein to be performed by the processor 1003 (or other processor). Computer program code for carrying out operations for various aspects described herein may be written in any combination of one or more programming language(s), and can be loaded from a computer usable medium/disk 1014 or otherwise into code memory 1016 for execution. The program code may execute, e.g., entirely on processor 1003, partly on processor 1003 and partly on a remote computer connected to network 1010, or entirely on the remote computer.

Alternative Embodiments

Figure 12A:
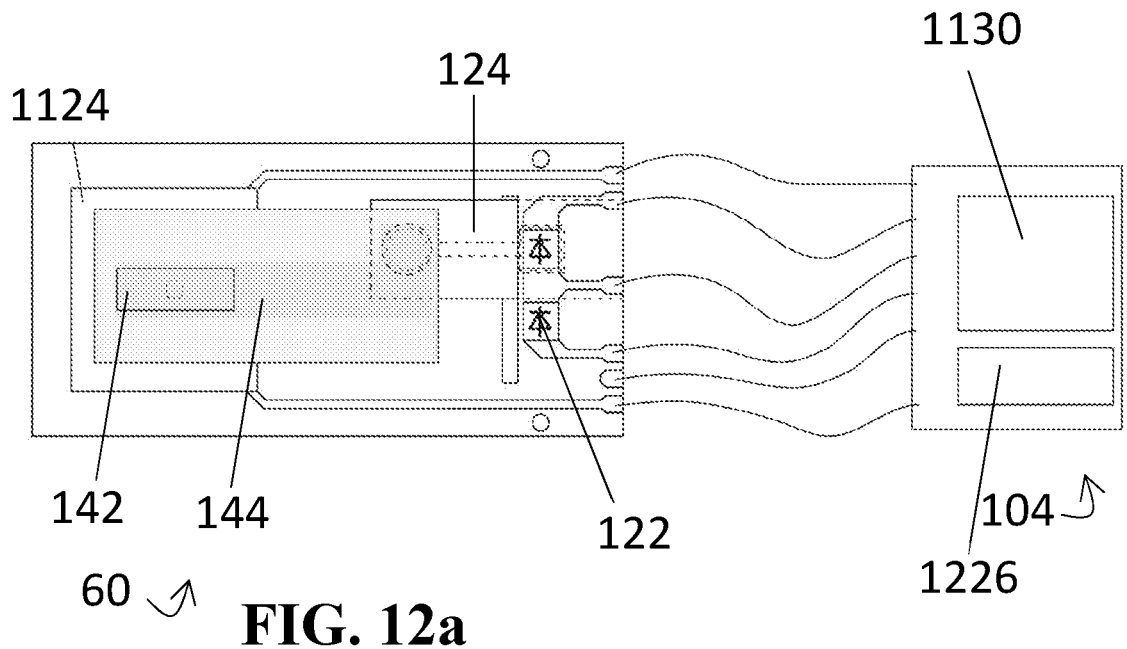
FIGS. 12a, 12b, and 12e show a disposable device according to an exemplary embodiment of the present disclosure, the device coupled with an external, commercial battery, and comprising a wet sensor (FIGS. 12a and 12b) and not comprising a wet sensor (FIG. 12e)
Figure 12B:
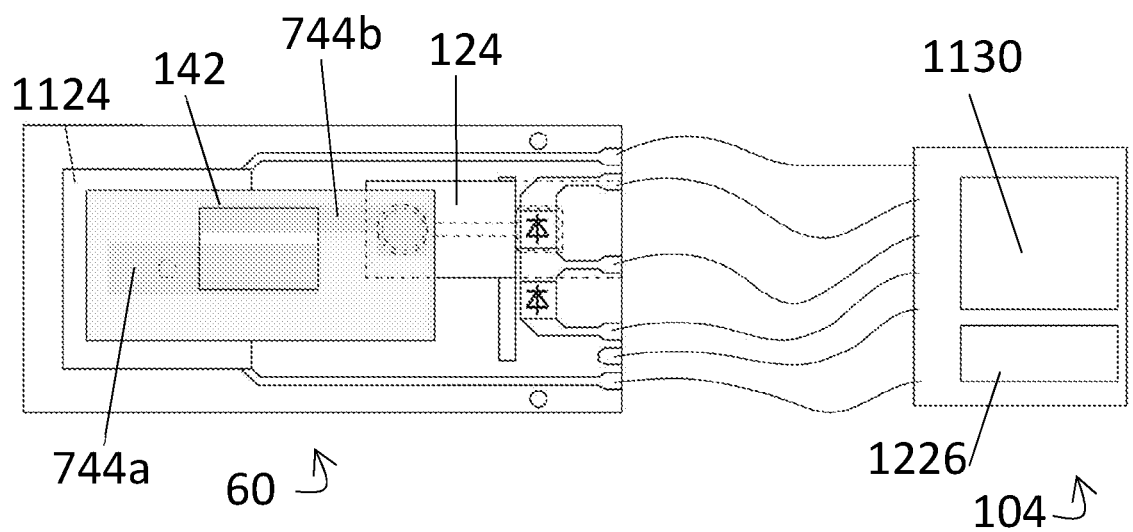
Figure 12C:
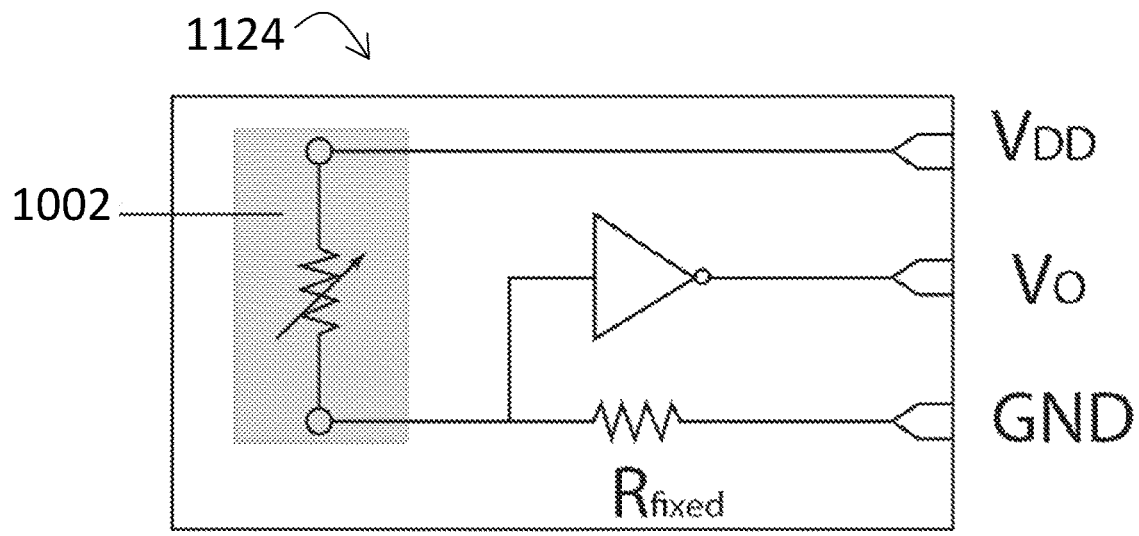
FIGS. 12c and 12d show embodiments of a wet sensor of the device of FIGS. 12a and 12b.

A discussion of various alternative embodiments and modifications of the components of the system 100 and/or disposable device 60 will now be described. As previously noted, certain embodiments of the detection system 100 and/or disposable device 60 can be implemented where the battery 130 comprises an external power supply (such as an external, commercial battery or wall power) as opposed to an on-board, liquid-activated battery. FIGS. 12*a*, 12*b*, and 12*c* illustrate several examples of such embodiments. Here, the power source unit 104 comprises an external power supply 1130 that is positioned outside of (and optionally apart from) the diaper (not shown) and coupled with the appropriate electrical circuitry 1226 (including, for example, a sensor signal processing unit 108, data transmission unit 110, and a power stage 132 and, in this at least one embodiment, the sensor signal processing unit 108 is configured to process not only the optical sensor signal, but also the wet sensor 1124 signal as described below). As the external power supply 1130 is not itself liquid-activated, nor positioned within the diaper 10 to detect urination or the like, without a means to detect when liquid will reach the open area 142 of the system 100, the external power supply 1130 must operate continuously (which is inefficient in terms of energy consumption) or between intermittent intervals to ensure the appropriate measurements can be obtained.

To address the need to "wake up" or otherwise provide power to the system 100 periodically until the liquid reaches the disposable device 60, in at least one embodiment comprising an external power supply 1130 the detection system 100 further comprises a wet sensor 1124. The wet sensor 1124 is designed to wake-up the sensing unit 102 when activated by a liquid akin how the liquid-activated battery 130 is activated by a liquid in previously-described embodiments. The wet sensor 1124 is integrated within the disposable device 60 and in fluid communication with the transport path 144 of the system 100 such that, when liquid 402 (urine) enters the open area 142, the wet sensor 1124 is wetted first, which activates the external power supply 1130 and, thereafter, the liquid 402 is guided via the transport path 144 to the sensing strip 124.

FIG. 12*a* shows an embodiment of the disposable device 60 coupled with an external, external power supply 1130, where the wet sensor 1124 and the sensing strip 124 are in communication with the same transport path 144. Alternatively, as shown in FIG. 12*b*, two separate transport paths 744*a*, 744*b* may be employed (similar to the embodiments described in connection with FIGS. 7*a* and 7*b*). In both scenarios, the time difference between the activation of the wet sensor 1124 and activation of the sensing strip 124 is adjustable.

Figure 12D:
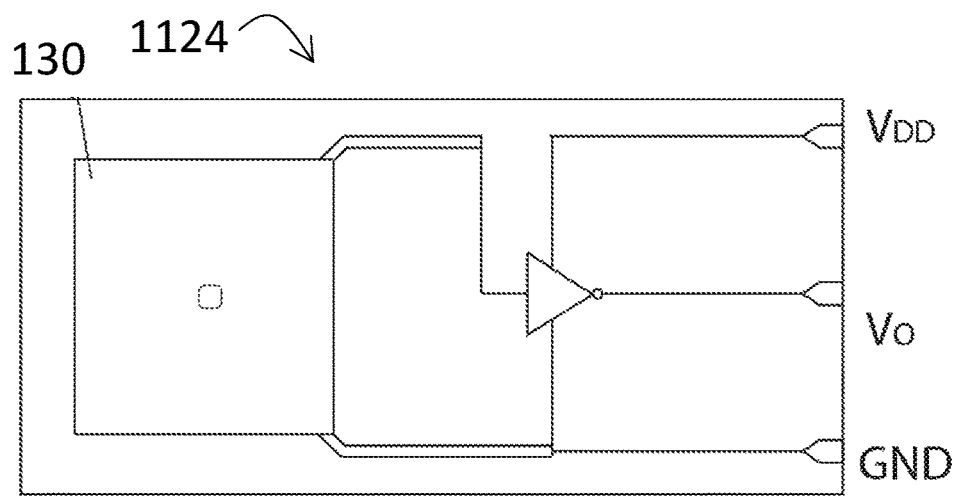

The wet sensor 1124 may be implemented using a variety of designs. For example, in at least one embodiment, the wet sensor 1124 comprises a humidity sensitive resistor (humistor 1002) as shown in FIG. 12*c*. Alternatively, in at least an additional embodiment shown in FIG. 12*d*, a liquid-activated battery 130 can be used as a wet sensor 1124 instead of a battery. To be used as a wet sensor 1124, the size of the liquid-activated battery 130 can be much smaller because it need not provide power to the system 100 (the external power supply 1130 handles that aspect). Indeed, such battery 130 may be operable to generate between about 0.9V to about 1.1V when activated, with the signal from the wet sensor 1124/battery 130 obtained through an inverter comprising a threshold voltage of at or about 0.5V, for example. It will be appreciated that any of the liquid-activated batteries 130 of the previously described embodiments may be used as a wet sensor 1124, with such systems 100 additionally be coupled with an external power supply 1130.

Figure 12E:
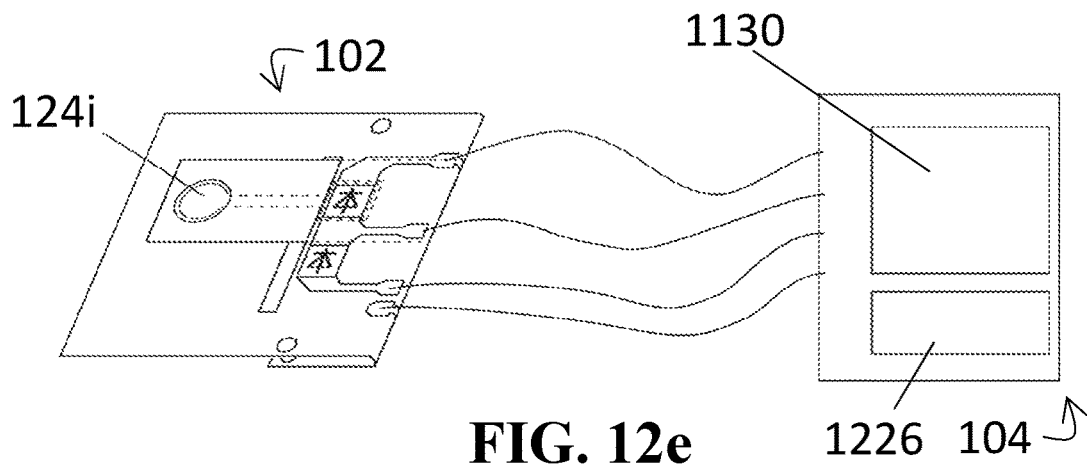

Likewise, it will be appreciated that an external power supply 1130 may be employed with the system 100 and disposable device 60 without using a wet sensor 1124. Examples of such an external power supply 1130 may include an external battery (commercial or otherwise), a generator, wall power (e.g., accessible through an electrical outlet or otherwise), or any other suitable external power source. Indeed, the disposable device 60 may be in electrical communication with an external power supply 1130 (i.e. powered thereby), with the power source unit 104 configured to operate in a periodic checking mode. FIG. 12e illustrates at least one embodiment of such a disposable device 60. There, a user may set the external power supply 1130 (using the timing controller 1652 described below, the computing unit 112, or otherwise) to supply power to the sensing unit 102 in pre-defined intervals that enable the recording of periodic measurements. Accordingly, measurements can be captured from the dry reagent strip 124r as well as the wet and/or reacted reagent strip 124r (i.e. where power is supplied after liquid 402 has been absorbed through the system 100).

Operation and Methods

Figure 13A:
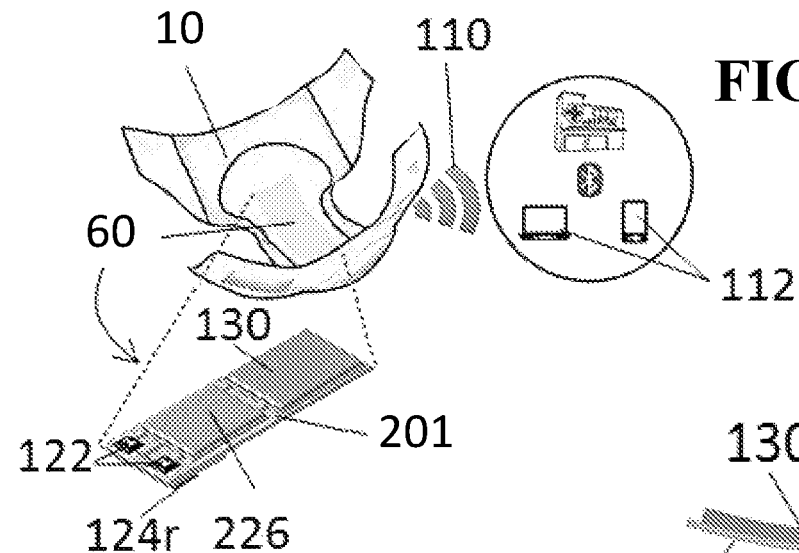
FIGS. 13a and 13b show a perspective view of the components of the system of FIG. 1a implemented via a diaper-embedded detection device of the present disclosure (FIG. 13a) and a schematic view representative of a cross-section of device (FIG. 13b)
Figure 13B:
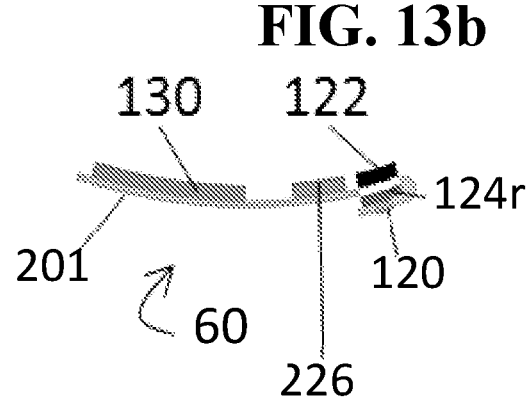

Operation of the system 100 and disposable device 60 will now be described in additional detail in connection with a method 1200 for detection. For reference, FIGS. 13a and 13b show a perspective view of the components of the system 100 comprising a detection disposable device 60 embedded within a diaper 10 (FIG. 13a) and a schematic view representative of a cross-section of the disposable device 60 (FIG. 13b). In this embodiment, the detection disposable device 60 comprises at least one on-board liquid-activated battery 130 and the liquid 402 of interest comprises urine; however, the method 1200 can be employed in connection with any system 100 and/or disposable device 60 configuration and/or to detect any targeted compound/ion desired, provided the reagent strip 124r comprises the appropriate reagents.

Figure 14A:
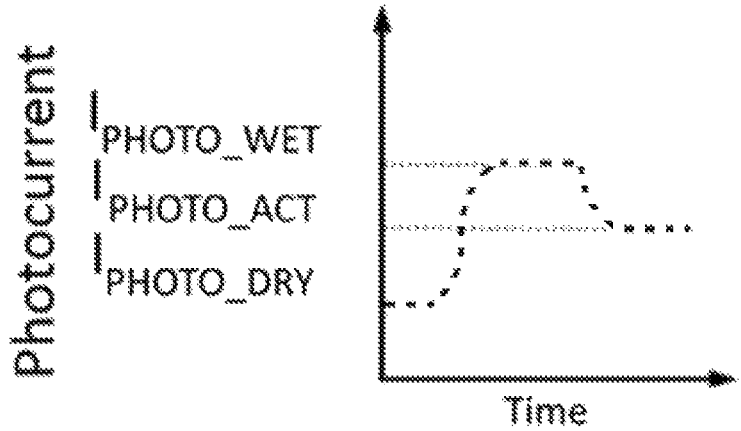
FIGS. 14a-14c show output data measured by the detection system according to an exemplary embodiment of the present disclosure as a function of time.
Figure 14B:
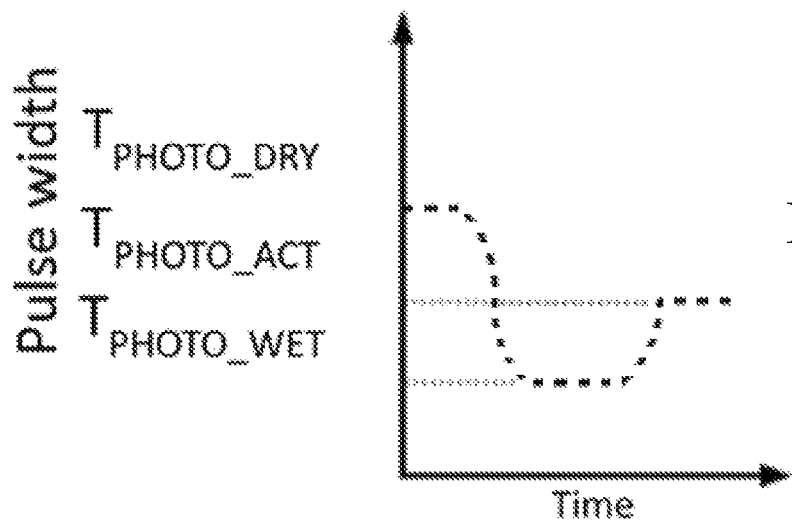
Figure 14C:
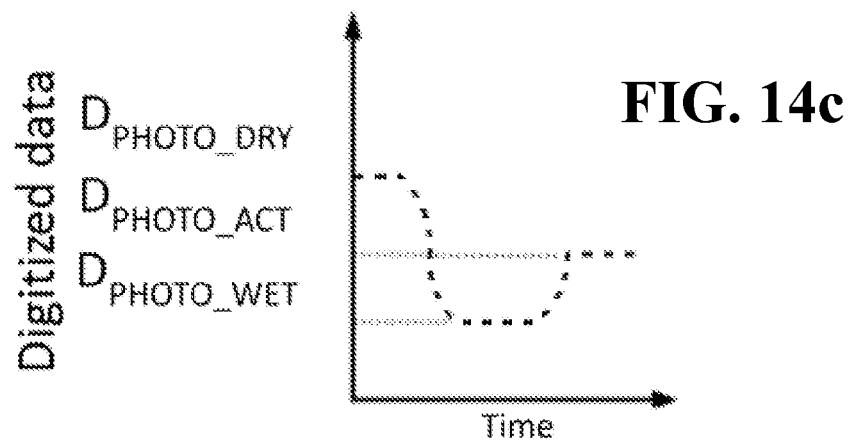
Figure 15A:
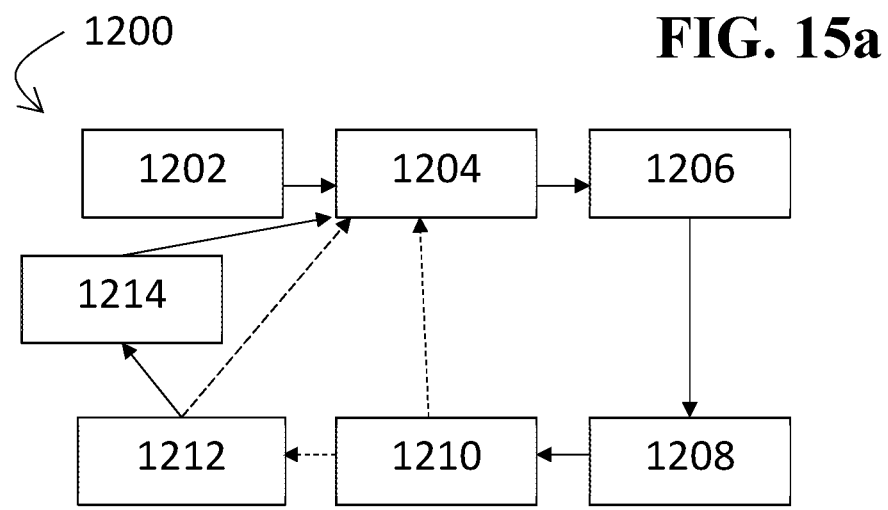
FIGS. 15a and 15b display flow charts of a method of detecting a targeted compound according to an exemplary embodiment of the present disclosure.
Figure 15B:
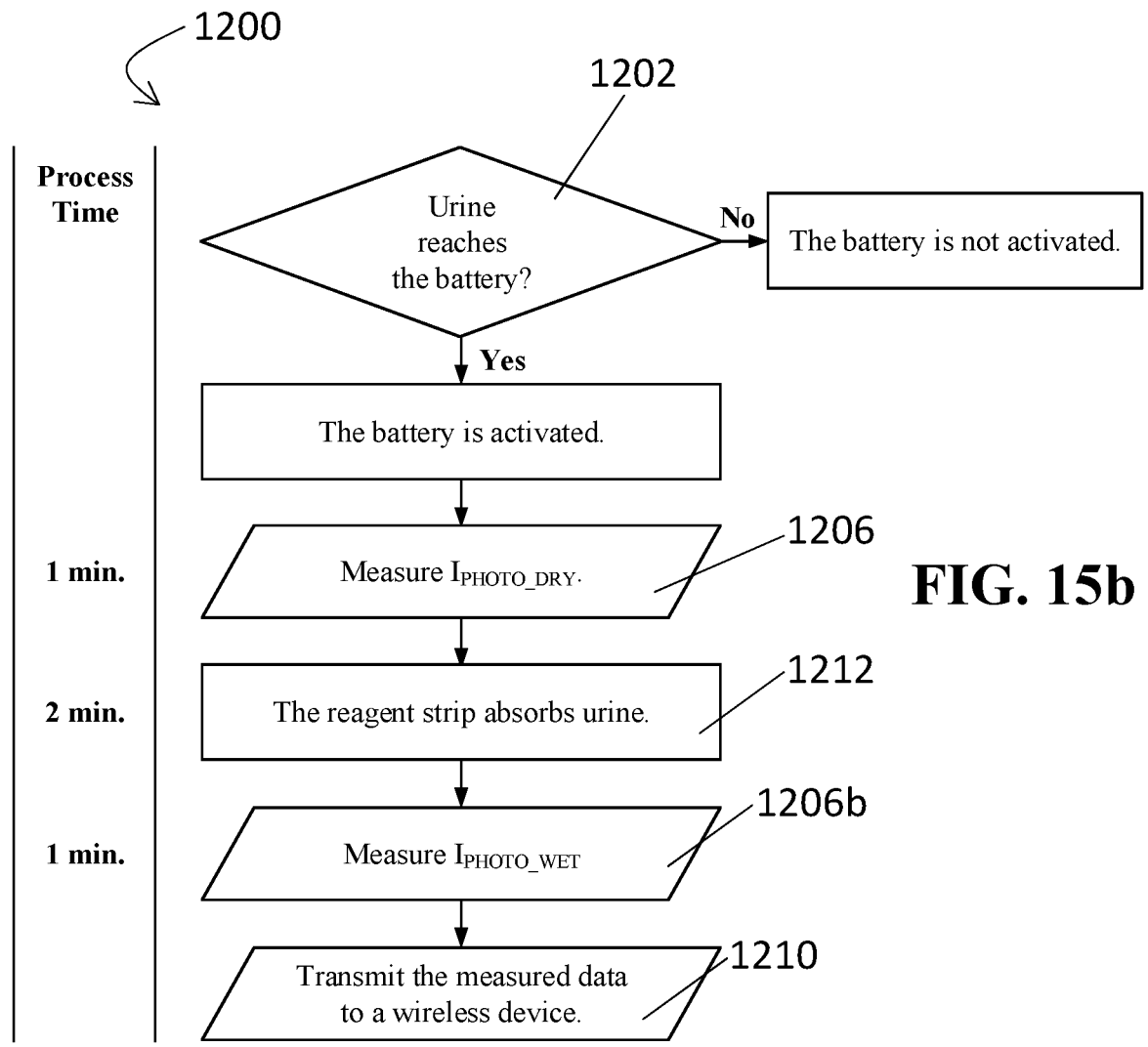
Figure 15C:
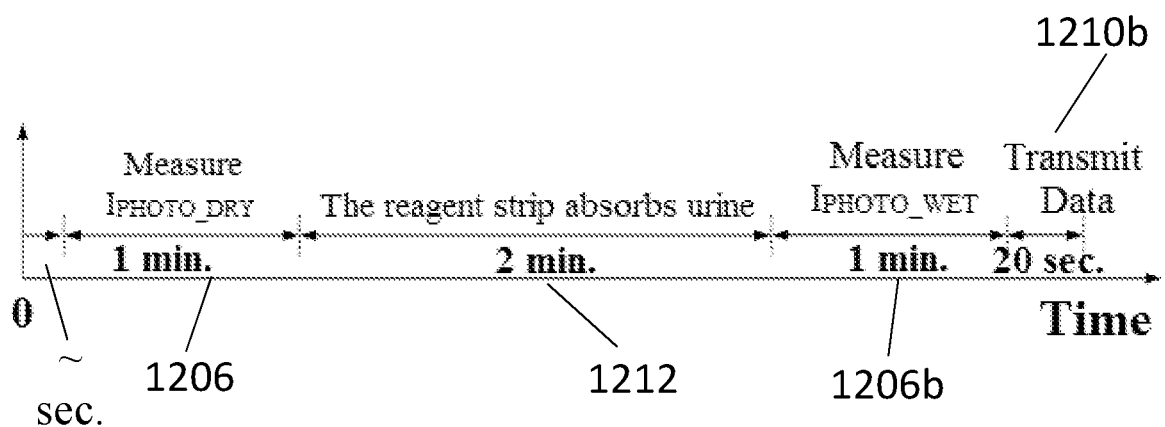
FIG. 15c shows a timing diagram associated the method of detecting of FIGS. 15a and 15b.

Now referring to FIGS. 14a-15c, FIGS. 14a-14c show three graphs representative of photocurrent measurements recorded using the method 1200, FIGS. 15a and 15b show flow-charts depicting the steps of the method 1200, and FIG. 15c shows a timing diagram associated with at least one embodiment of method 1200. In operation, at step 1202 the power source unit 104 of the system 100 is activated and provides power to drive performance of the steps of the method 1200. Where the detection disposable device 60 comprises at least one on-board, liquid-activated battery 130, step 1202 may comprise liquid/urine 402 reaching the open area(s) 142 of the path unit 106, delivering the liquid/urine 402 to the liquid-activated battery 130 via the path unit 106 (by way of the transport path(s) 144), and initiating power to the system 100 via activation of the liquid-activated battery 130. Alternatively, where the system 100 comprises an external, external power supply 1130 and a wet sensor 1124, step 1202 comprises liquid/urine 402 reaching the open area(s) 142 of the path unit 106, delivering the liquid/urine 402 to the wet sensor 1124 via the path unit 106 (by way of the transport path(s) 144 or otherwise), and initiating power to the system 100 via activation of the external power supply 1130. Still further, where the system comprises an external, external power supply 1130 configured and/or programmed for intermittent operation, step 1202 may occur without liquid/urine 402 reaching the open area(s) 142 and/or entering the disposable device 60; instead, power will be delivered to the disposable device 60 at step 1202 pursuant to a predefined schedule established either by a default setting or programmed pursuant to user preference.

When power is provided to the disposable device 60 at step 1202, the method 1200 proceeds to step 1204. At step 1204, light from the light source(s) 120 travels through the reagent strip 124r of the sensing strip 124 (which is currently dry), and reaches the photodetector 122 (i.e. an active photodiode). In response to the light, the photodetector 122a measures the photocurrent ($I_{PHOTO\_DRY}$) at step 1206 (e.g., for at or about 1 minute) and the sensor signal processing unit 108 then converts the photocurrent ($I_{PHOTO\_DRY}$) into a digital signal at step 1208. For example, using a pulse width modulation technique, the sensor interface circuit 150 converts the photocurrent into a square signal where its pulse width ($T_{PHOTO\_DRY}$) is proportional (or inversely proportional) to the photocurrent ($I_{PHOTO\_DRY}$), and the microprocessor 152 digitizes the pulse width ($D_{PHOTO\_DRY}$). (It will be appreciated that the pulse width modulation is only one example of a technique for performing step 1208 and that other technique(s) may be used.) At step 1210, the digitized output ($D_{PHOTO\_DRY}$) may be transmitted to the computing unit 112 or saved in a register (associated with the microprocessor 152 or otherwise) for later transmission.

At step 1212, the liquid/urine 402 reaches the reagent strip 124r of the sensing unit 102, which changes the amount of light from the light source 120 that reaches the photodetector 122a and, thus, changes the photocurrent ($I_{PHOTO\_WET}$) reading. Based on the overall configuration of the disposable device 60 (and, perhaps more specifically, at least the transport path 144), in at least one embodiment, the amount of time it takes for the liquid/urine 402 to traverse the transport path 144 and reach the reagent strip 124r comprises at least 10 seconds, which is enough time for the battery 130 to generate sufficient power to turn on the measurement circuitry (102 and 108). However, in at least one embodiment, the sensor unit 102 waits for at or about 2 minutes for the liquid 402 to reach the reagent strip 124r prior to taking any additional recordings. Thereafter, steps 1204-1210 of the method 1200 repeat (now labeled 1204b-1210b to represent a second round through the method 1200), with the light traveling from the light source 120, through the reagent strip 124r, and to the photodetector 122a at step 1204b, the photodetector 122a generating photocurrent (now $I_{PHOTO\_WET}$ as the sensing strip 124 is currently wet) at step 1206b, and the sensor signal processing unit 108 converting the photocurrent ($I_{PHOTO\_WET}$) into a digital signal at step 1208b. At step 1210b, the digitized output ($D_{PHOTO\_WET}$) may again either be transmitted to the computing unit 112 or saved in a register (associated with the microprocessor 152 or otherwise) for later transmission.

After the reagent strip 124r is wetted by the liquid/urine 402 at step 1202, the chemical/reagent within the reagent strip 124r begins to react with any targeted ion/compound (e.g., nitrite or nitrate) within the liquid/urine 402 and, if present, the color of the sensing strip 124 changes (typically from white to pink when used for the detection of nitrate or nitrite within urine). Notably, however, the chemical reaction between the ion/compound of interest and the chemical/reagent within the reagent strip 124r takes some time after the strip 124 gets wet to complete the reaction. While the reagent strip 124r may be wet when the photocurrent measurement $I_{PHOTO\_WET}$ is generated at the second iteration of step 1206, the reaction has not yet fully occurred. In at least one embodiment, a complete reaction may require between about 60-120 seconds to occur. Accordingly, the previously described photocurrent $I_{PHOTO\_WET}$ is an intermediate (pre-reaction) photocurrent measurement. The additional change in color that occur as the chemicals/reagents react affects the amount of light from the light source 120 that reaches the photodetector 122a and, thus, the resulting photocurrent measurement obtained at step 1206.

The method 1200 may also be used to determine a post-reaction measurement of photocurrent ($I_{PHOTO\_ACT}$). Accordingly, following step 1212 (where the liquid/urine 402 reaches the reagent strip 124r), at step 1214 the reagent strip 124r completes the reaction to achieve its final color. Again, steps 1204-1210 may be repeated to detect the fully-reacted photocurrent $I_{PHOTO\_ACT}$ and compute the corresponding digital data $D_{PHOTO\_ACT}$. Briefly, steps 1204-1210 of the method 1200 are performed, with the light traveling from the light source 120, through the reagent strip 124r, and to the photodetector 122a (step 1204), the photodetector 122a generating photocurrent (now $I_{PHOTO\_ACT}$, as the sensing strip 124 is wet and fully reacted) (step 1206), and the sensor signal processing unit 108 converting the photocurrent ($I_{PHOTO\_ACT}$) into a corresponding digital signal ($D_{PHOTO\_ACT}$) (step 1208). At step 1210, the digitized output ($D_{PHOTO\_ACT}$) may either be transmitted to the computing unit 112 (along with the dry and wet condition data—$D_{PHOTO\_DRY}$ and $D_{PHOTO\_WET}$—if they were stored in registers, or the $D_{PHOTO\_ACT}$ data can be saved in a register for later transmission per to user preference. For proper calibration, it is optimal that the detection system 100 has at least $D_{PHOTO\_DRY}$ and $D_{PHOTO\_WET}$ measurements; however, computation may be performed using at least one of the foregoing.

Measuring nitrite in a liquid using the system 100, disposable device 60, and method 1200 of the present disclosure has multiple applications. It is well known that nitrite in the urine is a surrogate of a UTI. Nitrite is never found naturally in the urine, and many species of gram-negative bacteria convert nitrate to nitrite. Consequently, the detection system 100, disposable device 60, and method 1200 hereof can be used to detect a UTI by detecting nitrite (or nitrate) in the urine. The system 100 can be used as a stand-alone UTI detection system or it can be embedded within a diaper for autonomous UTI sensing (e.g., disposable device 60 embedded within diaper 10). When the presented detection system 100/disposable device 60 is embedded within a diaper for autonomous UTI detection, the urine itself (i.e. liquid 402) activates the battery 130. For diaper 10 embedding, after urination, the urine reaches the battery 130 prior to reaching the sensing strip 124, thereby allowing for the collection of dry, wet, and post-chemical reaction measurements in series.

Figure 16:
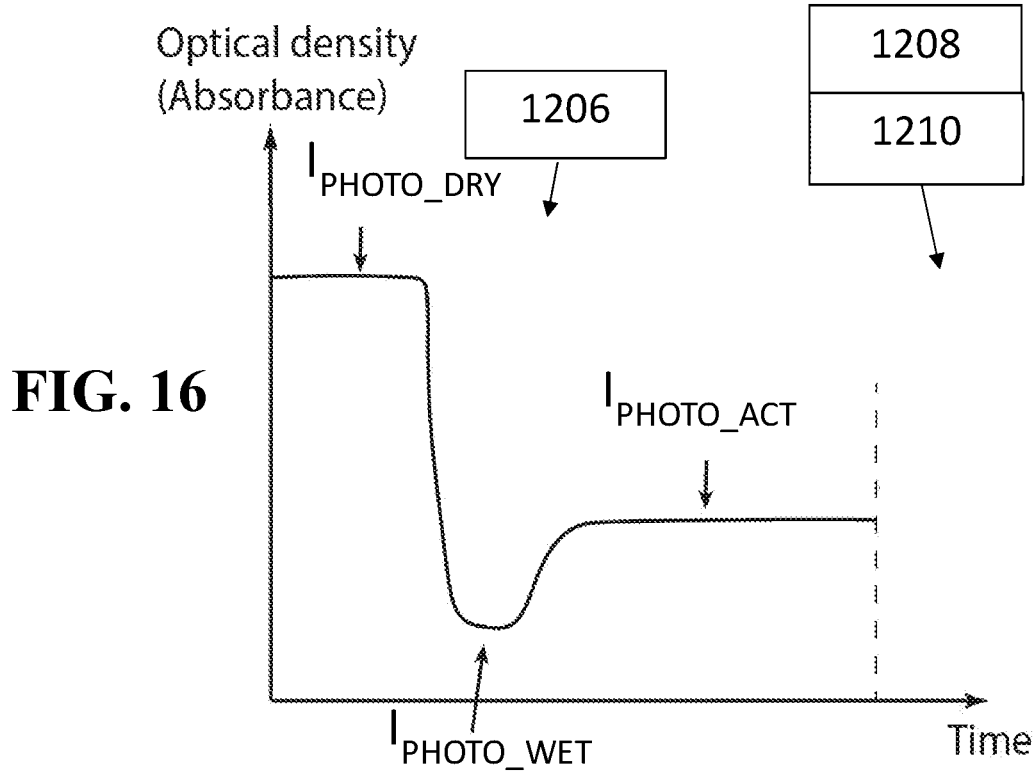
FIG. 16 shows a graphical representation of various optical density measurements generated by repeatedly performing a measurement step of a detection method using an autonomous version of the detection system according to an exemplary embodiment of the present disclosure.

FIG. 16 shows a graphical representation of various optical density measurements generated by repeatedly performing step 1206 of the method 1200 with an autonomous version of system 100 that is implemented using a detection disposable device 60 embedded within a diaper 10. Before urine 402 wets the reagent strip 124r for UTI sensing, the dry state measurement data of the reagent strip 124r impregnated matrix is obtained (step 1206, $I_{PHOTO\_DRY}$). Upon or immediately following the arrival of urine 402 within the disposable device 60 (through open area 142), the transport path 144 and, thus, the sensing strip 124/reagent strip 124r becomes wet (step 1212) and a wet (pre-reaction) measurement results (step 1206, $I_{PHOTO\_WET}$) and corresponding digital signal ($D_{PHOTO\_WET}$) (step 1208). As previously noted, the pre-reaction wet measurement can help evaluate the influence of intrinsic urine color. Thereafter, the reaction proceeds and the color of the reactants on the reagent strip 124r (urine and reagents) develops until a stable point (step 1214). Accordingly, assuming power is provided at step 1202, the steps 1204-1210 are repeated to obtain a post-reaction wet measurement (step 1206, $I_{PHOTO\_ACT}$) and corresponding digital signal ($D_{PHOTO\_ACT}$) (step 1208).

Notably, in those embodiments comprising an external, external power supply 1130 without a wet sensor 1124 (i.e. configured for intermittent operation), the method 1200 automatically cycles through steps 1204-1210 when power is provided at step 1202. As such, in such embodiments, performance of the method 1200 obtains the photocurrent measurement of whatever state the reagent strip 124r is at the time the measurement is generated (e.g., dry, pre-reaction wet, or post-reaction wet) and is not triggered upon any wetting or reaction event.

Figure 17A:
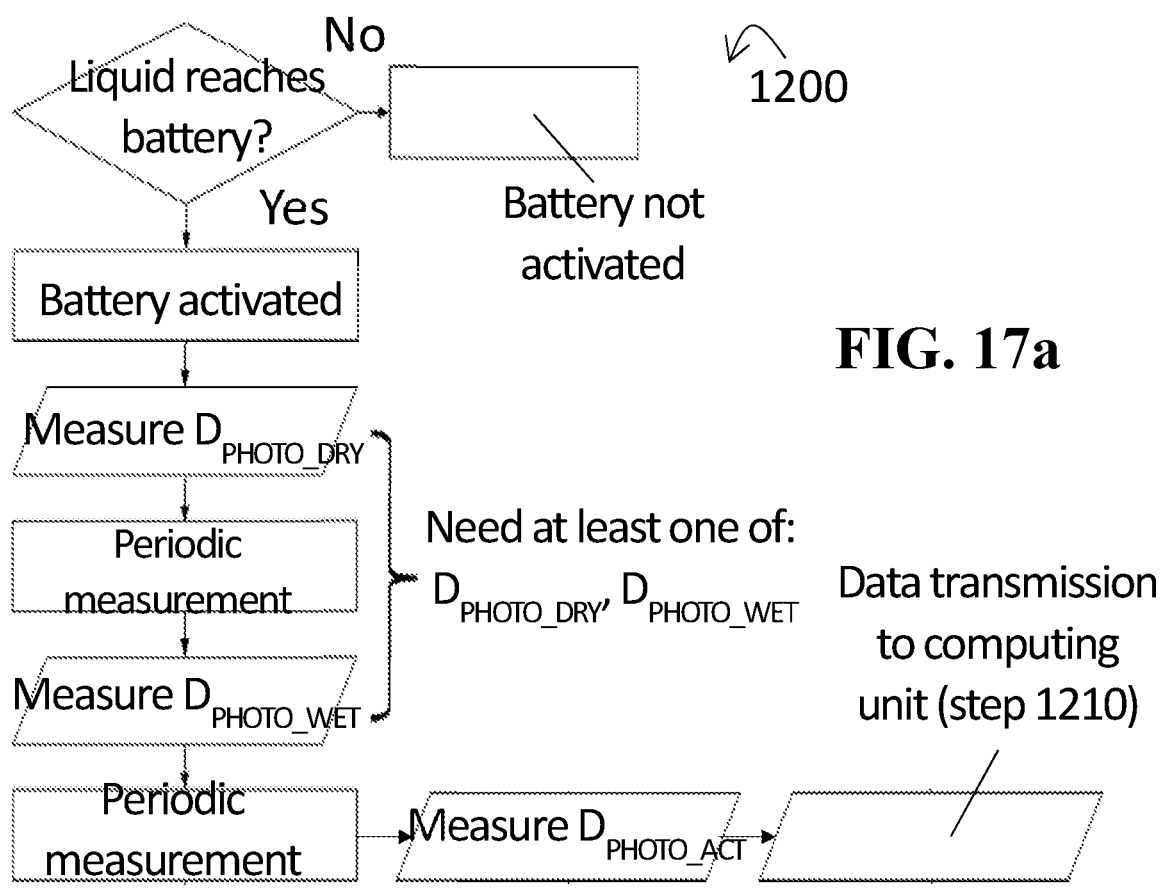
Figure 17B:
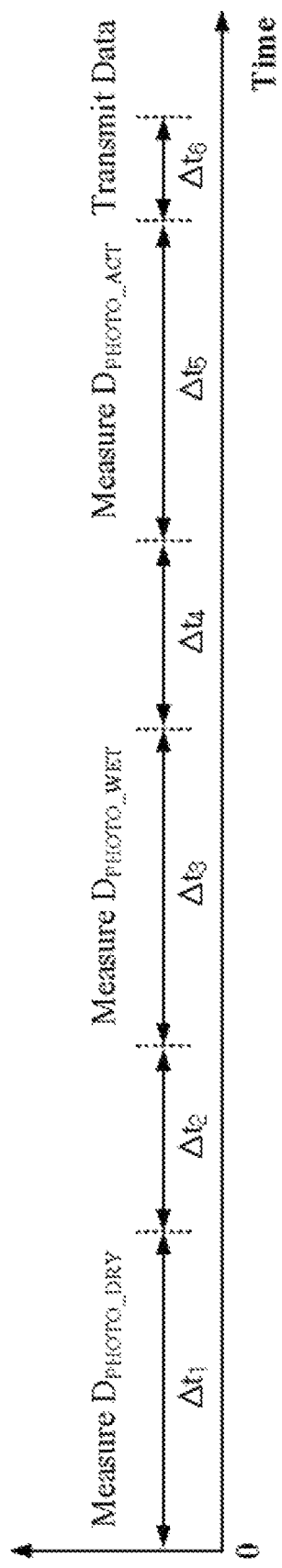

Now referring to FIGS. 17a and 17b, because the photocurrent is a function of the strip 124 color, and strip 124 color represents a targeted ion/compound concentration ("target concentration") within a liquid 402 (i.e. nitrate or nitrite concentration within urine), the computing unit 112 can back annotate the measured photocurrent to the ion/compound concentration. The data measured after the chemical reaction, $D_{PHOTO\_ACT}$, is enough to calculate the target concentration if there are no variations in the consisting elements such as light sources 120, photodetectors 122, sensing strips 124, and the like. However, process variations are often inevitable and, as such, there is a strong need to calibrate the errors introduced thereby to ensure reliable operation of the sensing unit 102. To account for the effect of process variations on the dry, wet, and post-reaction measurements and significantly reduce error, the devices 60, systems 100, and methods 1200 hereof utilize a differential reading technique and effective calibration methodologies. Indeed, the time lapse based differential reading technique and the on-line calibration utilizing a known reference significantly mitigate the adverse effects of process variations in the components without increasing the system complexity or power consumption. With the calibration, the maximum error in nitrite concentration estimation improved from 33% to 3.5%. The sensor unit 102 achieves a sensitivity of 1.35 ms/(mg/L) and a detection limit of 4 mg/L for nitrite.

Primarily, process variations may impact the output pulse width for a dry reagent strip 124r and for a wet reagent strip 124r (post-reaction) in the same manner. Consequently, the differential reading between the pulse width ($T_{PW1}$) for the dry reagent strip 124r and the pulse width ($T_{PW2}$) for the wet, post-reaction reagent strip 124r will suffer significantly less from process variations. To measure the difference, the devices 60/70, systems 100, and methods 1200 hereof allow for the use of a time lapse reading technique that can measure a dry or pre-reaction wet measurement as a reference.

As previously described, the sensing unit 102 and path unit 106 of the disposable device 60 are designed in such a way that the liquid 402 reaches the battery 130 (or wet sensor 1124) first, and the reagent strip 124r later. As soon as the battery(ies) 130 are active, the sensing unit 102 measures the $T_{PW1}$ as a reference, and the sensing unit 102 registers the differential pulse width, $T_{DPW}=T_{PW1}-T_{PW2}$, rather than $T_{PW1}$ (because pulse width T is an analog signal that cannot be processed in digital, its digital version D may be employed, with $T_{DPW}=T_{PW1}-T_{PW2}$ conceptually representative of how the system works; for actual digital signal processing (in the microprocessor or in a computer, $D_{DPW}=D_{PW1}-D_{PW2}$ may be used). Likewise, if the dry measurement is used as a reference, $D_{PHOTO\_ACT}-D_{PHOTO\_DRY}$ can be used to calculate the target concentration in the liquid 402 instead of using $D_{PHOTO\_ACT}$. Additionally or alternatively, $D_{PHOTO\_ACT}-D_{PHOTO\_WET}$ may be used to calculate the target concentration in liquid 402 instead of using $D_{PHOTO\_ACT}$.

FIGS. 17a and 17b show example flow charts depicting embodiments of the operational sequence associated with method 1200 and its timing diagram, respectively. Both FIGS. 15b and 17a assume the measured data are first stored in registers and subsequently transmitted together after finishing the measurements (step 1210). Alternatively, the measurement data can be transmitted after each measurement (dry, pre-reaction wet, post-reaction wet) or periodically without waiting for the final measurement.

Calibration methodologies are also provided in connection with the present disclosure. Assuming the effect of process variations in various components of the system (e.g., photodetector 122, light source 120, sensing strip 124, etc.) to the sensor output signal is linear, the accumulated effect of the process variations on the components can be calibrated using a signal constant. For example, a dry measurement result of a reference sensor module (a universal reference) can be employed for system calibration. For each end-user module, it makes dry and wet (before and/or after chemical reaction) measurements. By comparing the dry measurement of the end-user module with that of the reference module, a calibration constant can be determined. Because dry and wet measurements are affected by the process variations in the same manner, the wet measurement data of the end-user module can then be calibrated using the determined constant. The software (or firmware) of the system that performs the calibration needs to know the dry measurement result of the reference module in addition to the dry and wet measurement results of the end-user module.

Figure 17C:
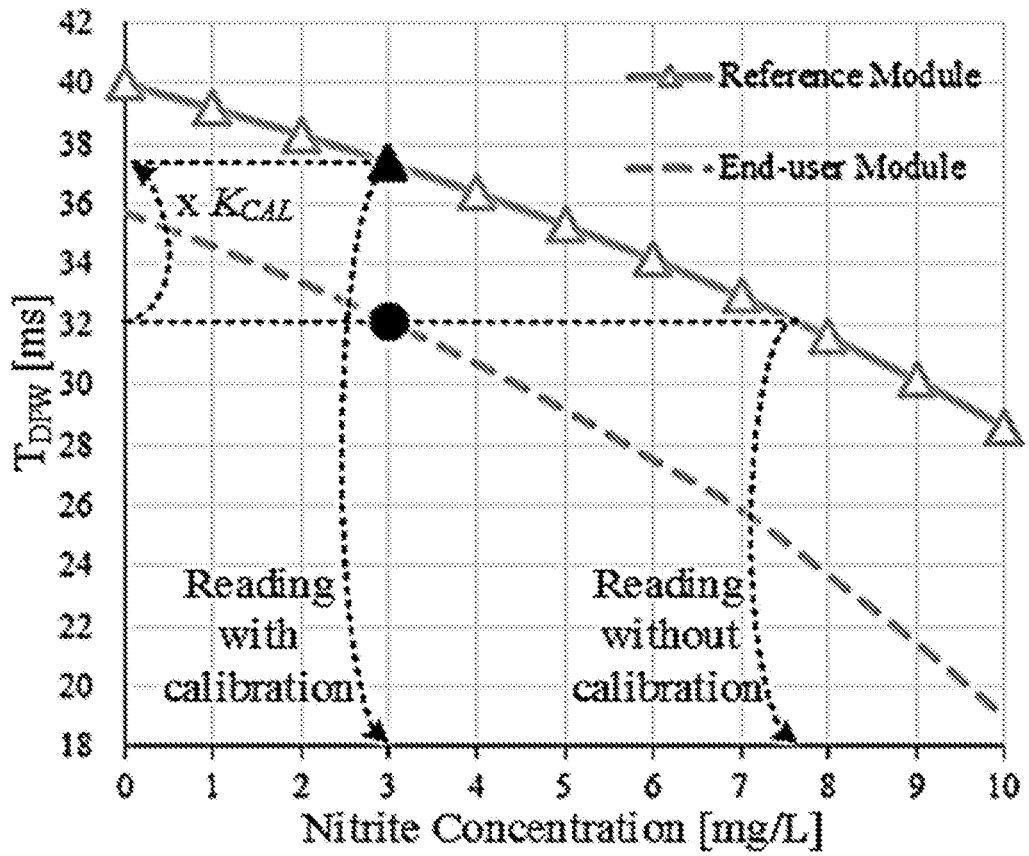
FIG. 17c shows a graph for use in calibration for process variations, the graph indicative of a known reference module.

As shown in FIG. 17c, the calibration finds a process variations constant number $K_{CAL}$ using a known reference and corrects the measured differential pulse width by multiplying by the constant $K_{CAL}$. In this method, as noted above, an arbitrarily selected sensor module may be selected as a known universal reference. The sensing unit 102 of the system 100 will have a performance deviation from the reference module and will show a different output pulse width at the same target concentration. The measured differential pulse width of the sensing unit 102 can be annotated back to the differential pulse width of the reference module by multiplying the constant $K_{CAL}$.

An explanatory example will now be provided in connection with the system 100 and disposable device 60 embedded within a diaper 10 for detecting UTIs from urine 402. Primarily, the nitrite concentration within the urine 402 is measured versus the differential pulse width curve using the known reference module as shown in FIG. 17c. The reference pulse widths ($T_{DPW,REF}$) can be expressed in connection with Equation (6) and using the differential reading technique $$T_{DPW,REF} = \beta_{REF}\left(\frac{1}{I_{DRY,REF}} - \frac{1}{I_{WET,REF}}\right) \quad (20)$$

where $I_{DRY,REF}$ is a reference photocurrent when the reagent strip 124r is dry and $I_{WET,REF}$ is a reference photocurrent when the reagent strip 124r is wet. The data for the reference module is stored in the computing unit 112 or other processor (e.g., a mobile device) that performs the calibration operation. Because each sensing unit 102 of the system 100 has a different constant β, each sensing unit 102 should be able to find its own value of β unless the constant value is measured for each module during the production stage, which is challenging where the disposable device 60 is intended for one-time use and to be disposable. In at least one embodiment of system 100 and disposable device 60, each sensing unit 102 can the value of β autonomously by utilizing the dry condition measurement. For the time lapse based differential measurement, the sensing unit 102 first measures the pulse width $T_{PW1}$. Because the nitrite concentration in the urine should not affect the constant β, the constant $K_{CAL}$ can be calculated using the measured $T_{PW1}$ and the known value of $T_{PW1,REF}$ from the known reference as follows:

$$K_{CAL} = \frac{T_{PW1,REF}}{T_{PW1}} = \frac{\beta_{REF}}{\beta} \cdot \frac{I_{DRY}}{I_{DRY,REF}} \quad (21)$$

As the process variations would impact the output pulse width for the sensing strip 124 in the same manner when it is dry or wet, the relationship between the two reference currents and the two end-user currents can be expressed as:

$$I_{DRY}=\varepsilon I_{DRY,REF}, I_{WET}=\varepsilon I_{WET,REF} \quad (22)$$

where $I_{DRY}$ is an end-user photocurrent when the sensing strip 124 is dry and $I_{WET}$ is an end-user photocurrent when the sensing strip 124 is wet. The calibrated differential pulse width $T_{DPW,CAL}$ can thus be obtained by multiplying the calculated constant $K_{CAL}$ to the measured differential pulse width and using Equation (23):

$$T_{DPW} = \beta\left(\frac{1}{I_{DRY}} - \frac{1}{I_{WET}}\right) \quad (23)$$

$$\begin{aligned}T_{DPW,CAL} &= K_{CAL} \cdot T_{DPW} \\ &= \beta_{REF}\left(\frac{1}{I_{DRY,REF}} - \frac{I_{DRY}}{I_{DRY,REF}}\frac{1}{I_{WET}}\right) \\ &= \beta_{REF}\left(\frac{1}{I_{DRY,REF}} - \frac{1}{I_{WET,REF}}\right)\end{aligned} \quad (24)$$

Power Management

Now referring to FIGS. 18a-19l, embodiments of the system 100 are shown that comprise some form of power management functionality. In embodiments of the detection system 100 that rely upon a liquid-activated battery 130 (see e.g., FIGS. 18a-18d), improving power efficiency is crucial to ensure reliable operation of the system 100 and to reduce the battery size. Accordingly, in at least one embodiment, the system 100 can be configured to utilize one or more sleep modes to significantly reduce its overall power consumption.

In light and/or deep sleep mode scenarios, the system 100 further comprises a switch 1650 electronically coupled with the light source 120 of the sensing unit 102 and a timing control 1652. The sensing unit 102, the sensor signal processing unit 108, and the data transmission unit 110 may each enter a light or deep sleep mode (i.e. a mode of operation that requires reduced or eliminated power consumption) by turning off the switch 1650. When in a sleep mode, the system's 100 functionality (or at least the functionality of the above-listed system units) is disabled except for the timing control 1652, which significantly reduces power consumption. Thereafter, the timing control 1652 may be configured to periodically wake the system 100 up between predefined sleep mode intervals to measure the output signal and ensure operation of method 1200 if urination is detected (i.e. a wet measurement). Accordingly, where sleep mode scenarios are activated, instead of measuring the sensor output signal frequently, the system 100 measures the sensor output at a reduced speed (e.g., instead of reading the output signals 10 times per second, the output signal is read 3 times per second). Between when the measurements are taken, the module/system 100 is in sleep mode so that only small amounts of power are drawn from the battery 130.

Figure 18A:
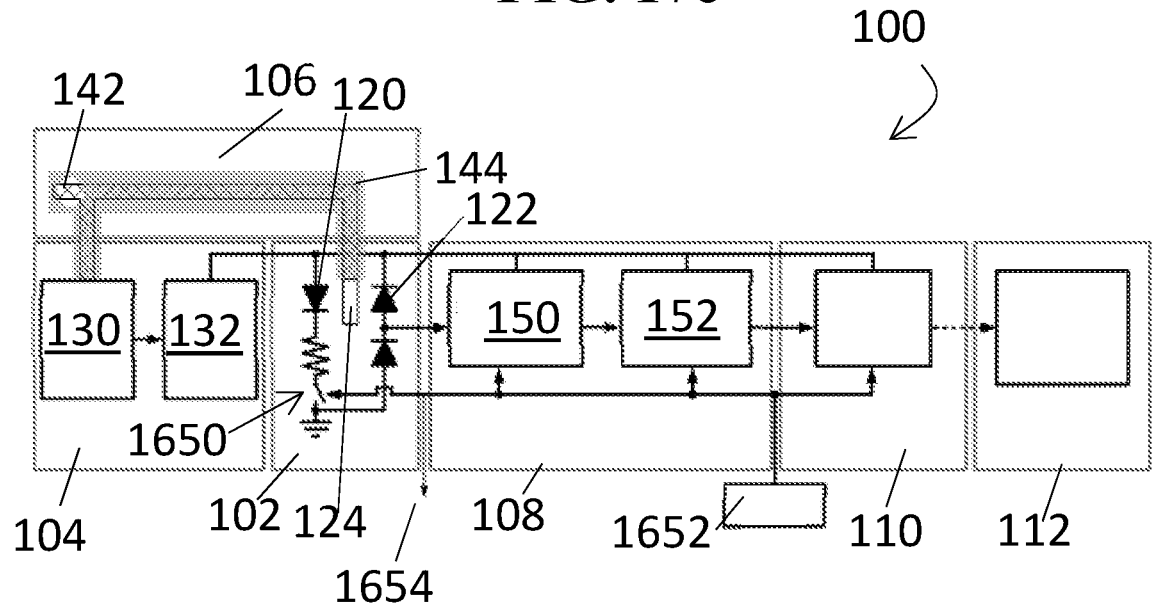
FIGS. 18a and 18b show block diagrams of exemplary embodiments of the detection system of the present disclosure that employ power management techniques to reduce power consumption.
Figure 18B:
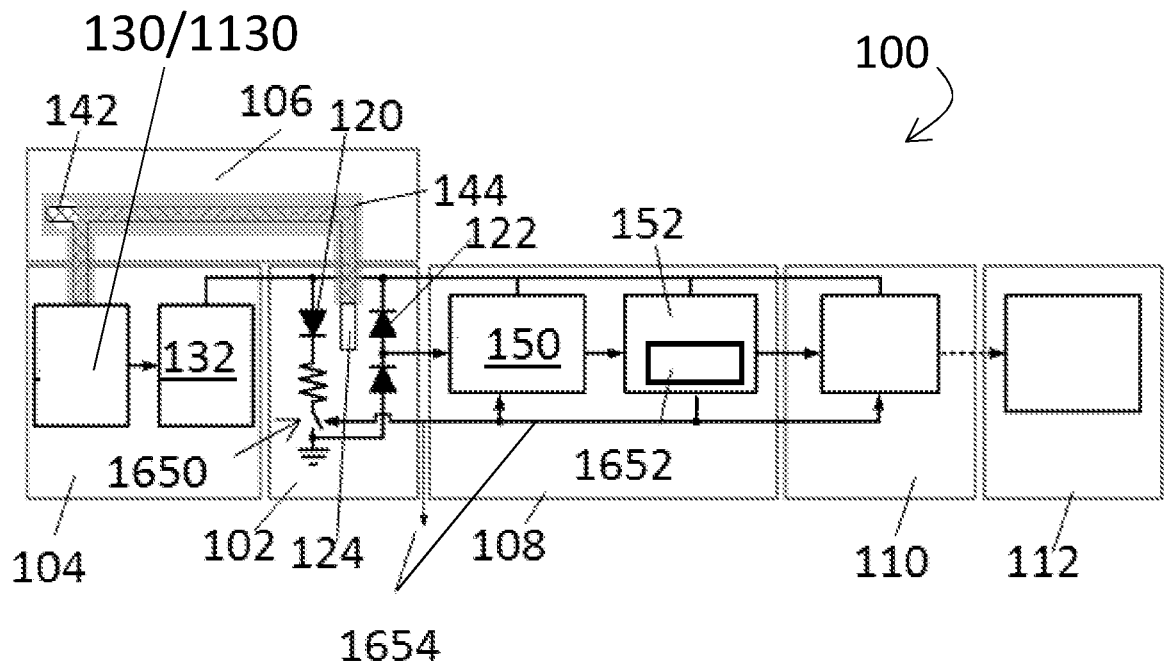

As shown in FIG. 18*a*, a separate timing control 1652 may be used. Alternatively, the timing control 1652 may be part of the microprocessor 152 as shown in FIG. 18*b*. Where the timing control 1652 is separate from the microprocessor 152, the timing control 1652 is nevertheless in operative communication therewith (including the sensor signal processing unit 108 generally), as well as the sensing unit 102, the data transmission unit 110, and the switch 1650.

Figure 18C:
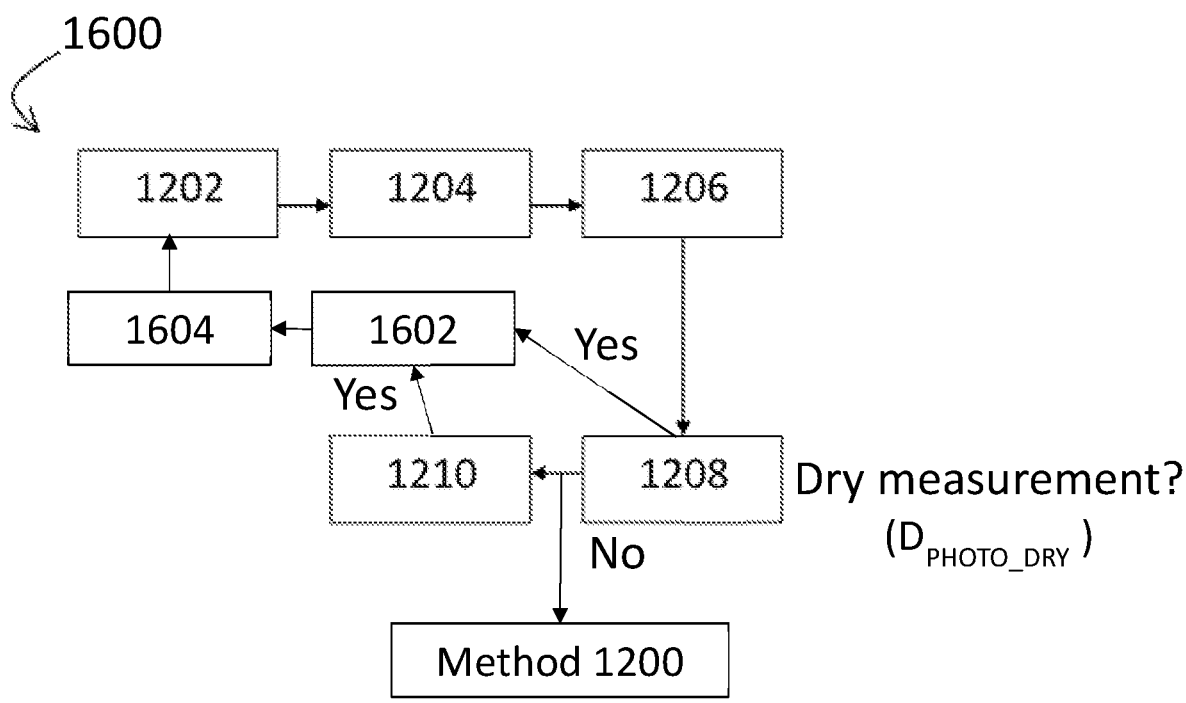
FIGS. 18c and 18d are flow chart of methods comprising power management techniques in connection with operation of a detection system according to an exemplary embodiment of the present disclosure.

Operation of the light sleep mode functionality is described in connection with an alternative embodiment of method 1200, with embodiments of a sleep mode method 1600 shown in the flow charts of FIGS. 18*c* and 16*d*. For the avoidance of doubt, all method steps shown in FIGS. 18*c* and 18*d* that include like reference numerals with those of method 1200 are identical to the corresponding method steps of method 1200 unless specified otherwise.

In at least one embodiment, the system 100 is configured to enter sleep mode when the output signal $D_{PHOTO\_DRY}$ is generated (i.e. indicating a dry sensing strip 124). Because the sensor 124 output signal changes slowly, continuous measurement of the sensor output is unnecessary. Accordingly, in method 1600, when the liquid-activated battery 130 becomes active at step 1202 (i.e. the batter 130 is activated by liquid 402), the detection system 100 performs steps 1204-1208 to generate the output signal $D_{PHOTO\_DRY}$ indicating that the sensing strip 124 is dry. If $I_{PHOTO\_DRY}$ is measured and/or the output signal $D_{PHOTO\_DRY}$ is obtained, the method 1600 proceeds to step 1602 and enters sleep mode by emitting sleep control signal 1654 to turn off the switch 1650. (Additionally, method 1600 may also include step 1210 to store and/or transmit the output signal as desired.) This prevents the system 100 from performing multiple measurements that will ultimately result in a dry output signal and, thus, preserves the power of the system 100.

Figure 18D:
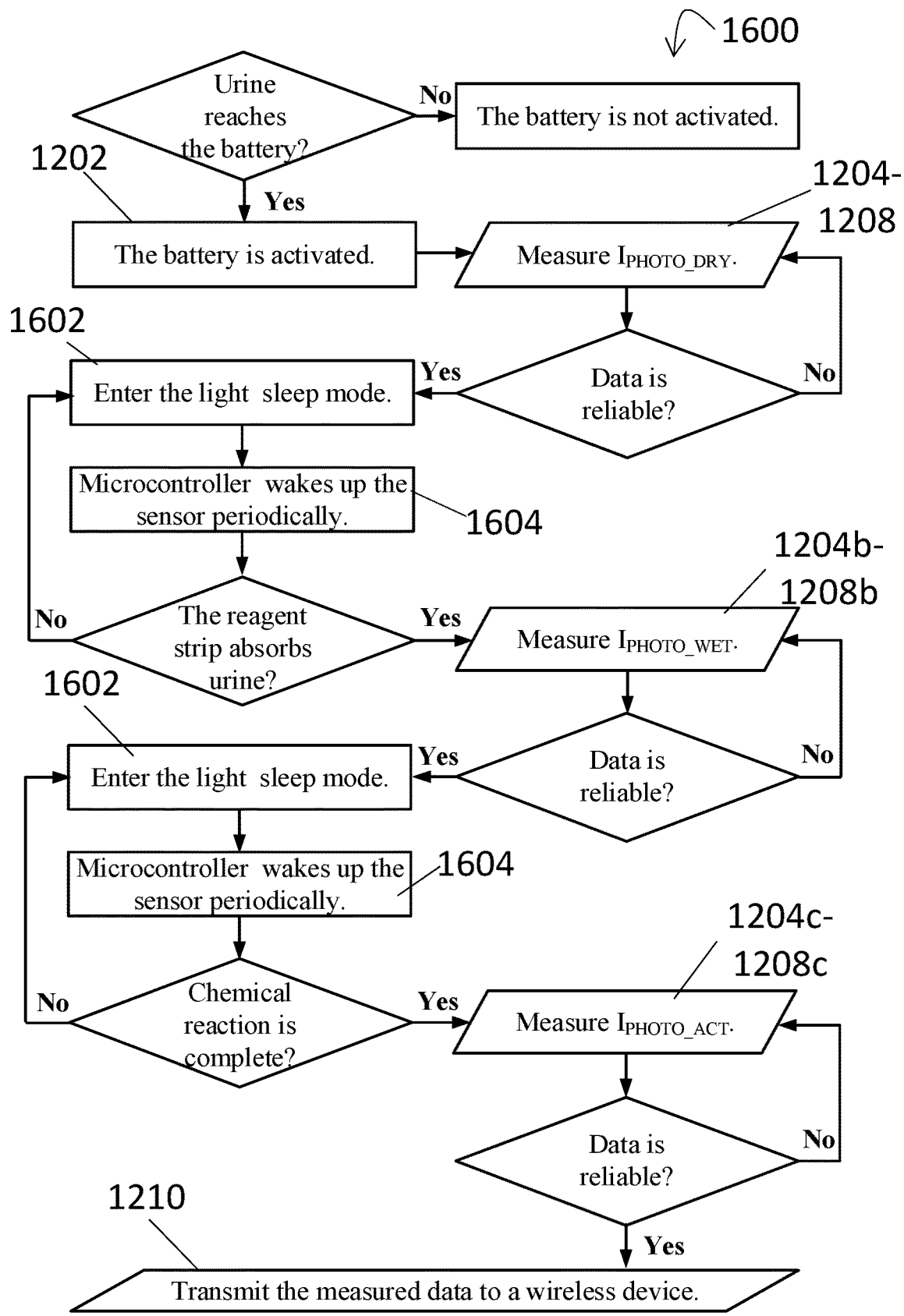

Additionally, in the at least one embodiment shown in FIG. 18*d*, the $I_{PHOTO\_DRY}$ measurement is assessed for reliability prior to the method 1600 advancing to step 1602. As previously mentioned, when in sleep mode, the functionality of the system 100 is significantly reduced or ceased altogether (except for operation of the timing control 1652) to promote the conservation of power and/or energy efficiency. However, after the system 100 is in sleep mode for a defined period of time (the value of which is either set as a system default or established by a user and monitored using the clock source 1030, for example), the method 1600 automatically advances to step 1604 and the microprocessor 152 operates the timing control 1652 to wake the system 100 up. In at least one embodiment, the timing control 1652 ceases providing the sleep control signal 1654, which turns the switch 1650 on and causes the system 100 to again perform at least steps 1204*b*-1208*b* (and, optionally, step 1210 if desired). In this manner, the method 1600 measures output signals periodically as shown in FIGS. 14*a*-14*c* (periodic measurement represented by dashed lines). Implementation of sleep mode functionality enables to the system 100 to go "off-line" to facilitate optimal power consumption, but also ensures that system 100 periodically wakes up to measure output signals and detect any abnormality therein that may be indicative of a UTI or another targeted disorder.

Referring briefly to the operation of the clock source 1030, a clock signal from a clock source 1030 may feed into the sensor interface circuit 150 and/or be utilized by a separate power monitoring unit 1802. There, if the detection system 100 is active at HIGH of the clock signal, LOW of the clock signal turns off all switches (e.g., switch 1650) and puts the microprocessor 152 of the sensor signal processing unit 108 into light sleep or deep sleep mode to save power. As previously described, the clock source 1030 may be integrated with (or a component of) the microprocessor 152, or external to the detection system 100. If a clock source 1030 comprises an external clock source 1030, LOW of the clock signal turns the microprocessor 152 fully off (deep sleep mode); however, if the microprocessor 152 generates the clock signal, in sleep mode the microprocessor 152 will be turned off except for a timer of the clock source 1030 for use in connection with generating a sleep control signal 1654 (e.g., a "wake-up" signal).

Utilization of sleep mode and method 1600 can significantly improve the power efficiency of the system 100, especially when the length of time in between sleep mode intervals is increased. Nevertheless, it is not ideal for sleep mode intervals to be too long to avoid missing a wet (pre-reaction) or post-reaction measurement. It will be appreciated that power consumption of the system 100 versus obtaining accurate and timely measurements should be optimized, and the parameters of the sleep mode intervals may be fully customized by a user.

A variety of system configurations (see, e.g., FIG. 19*a*), timing diagrams (see, e.g., FIG. 19*b*), and operational sequence steps (see, e.g., FIG. 19*c*) associated with method 1600 for implementing various sleep modes using the detection system 100. In these scenarios and as shown in the Figures and in addition to the components associated with the sleep mode approaches (i.e. switch 1650 and timing control 1652), the detection system 100 embodiments may additionally comprise one or more of an external power supply 1130, a wet sensor 1124, a power monitoring unit 1802 and/or a clock source 1030. These embodiments achieve different goals, most relating to power conservation.

Figure 19A:
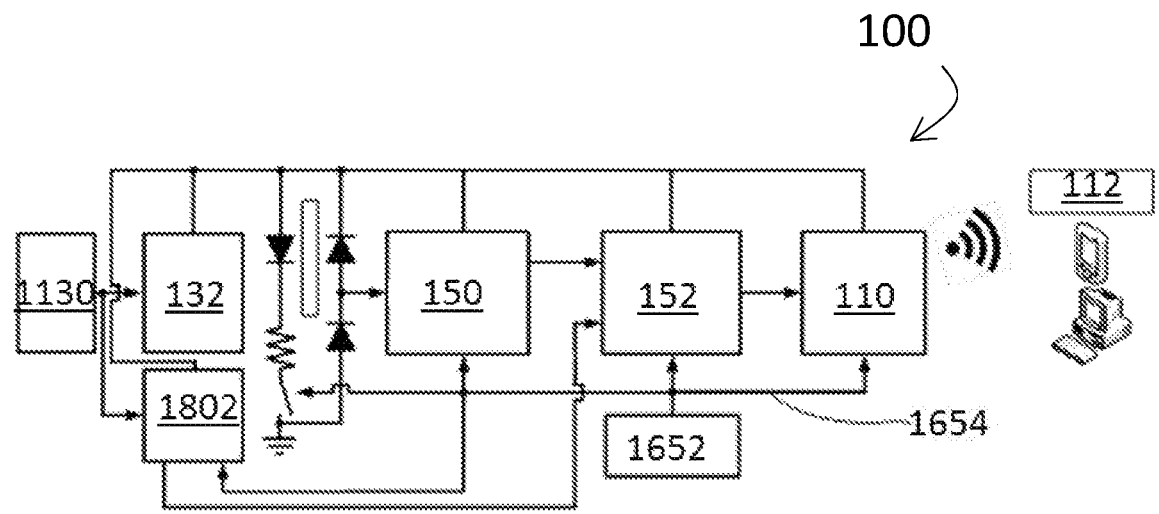
FIGS. 19a-19l show system configurations, operational sequences, and timing diagrams associated with methods comprising power management techniques in connection with operation of a detection system according to an exemplary embodiment of the present disclosure.
Figure 19B:
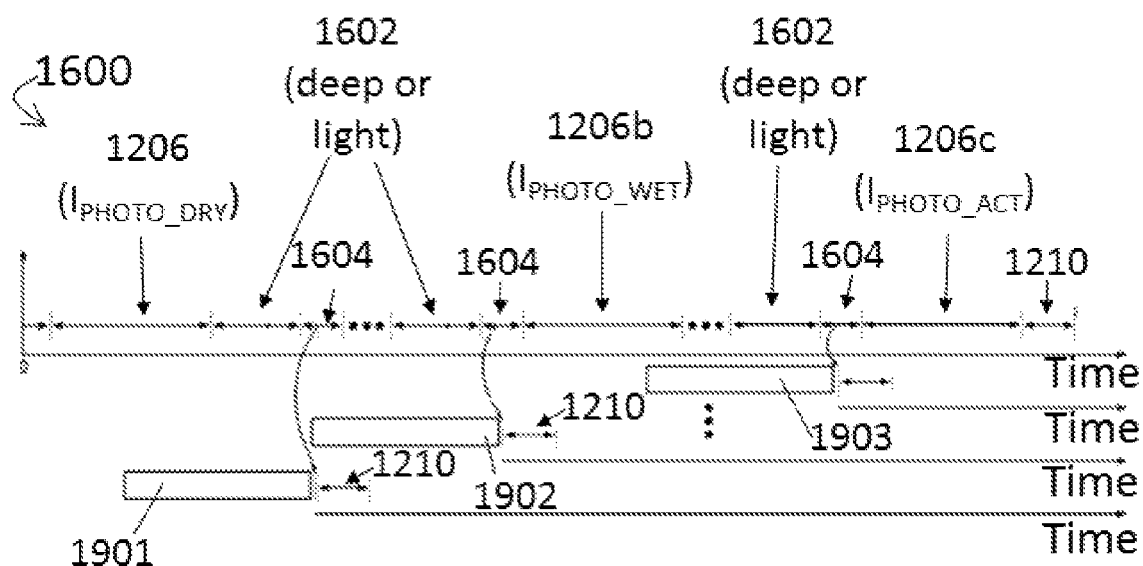
Figure 19C:
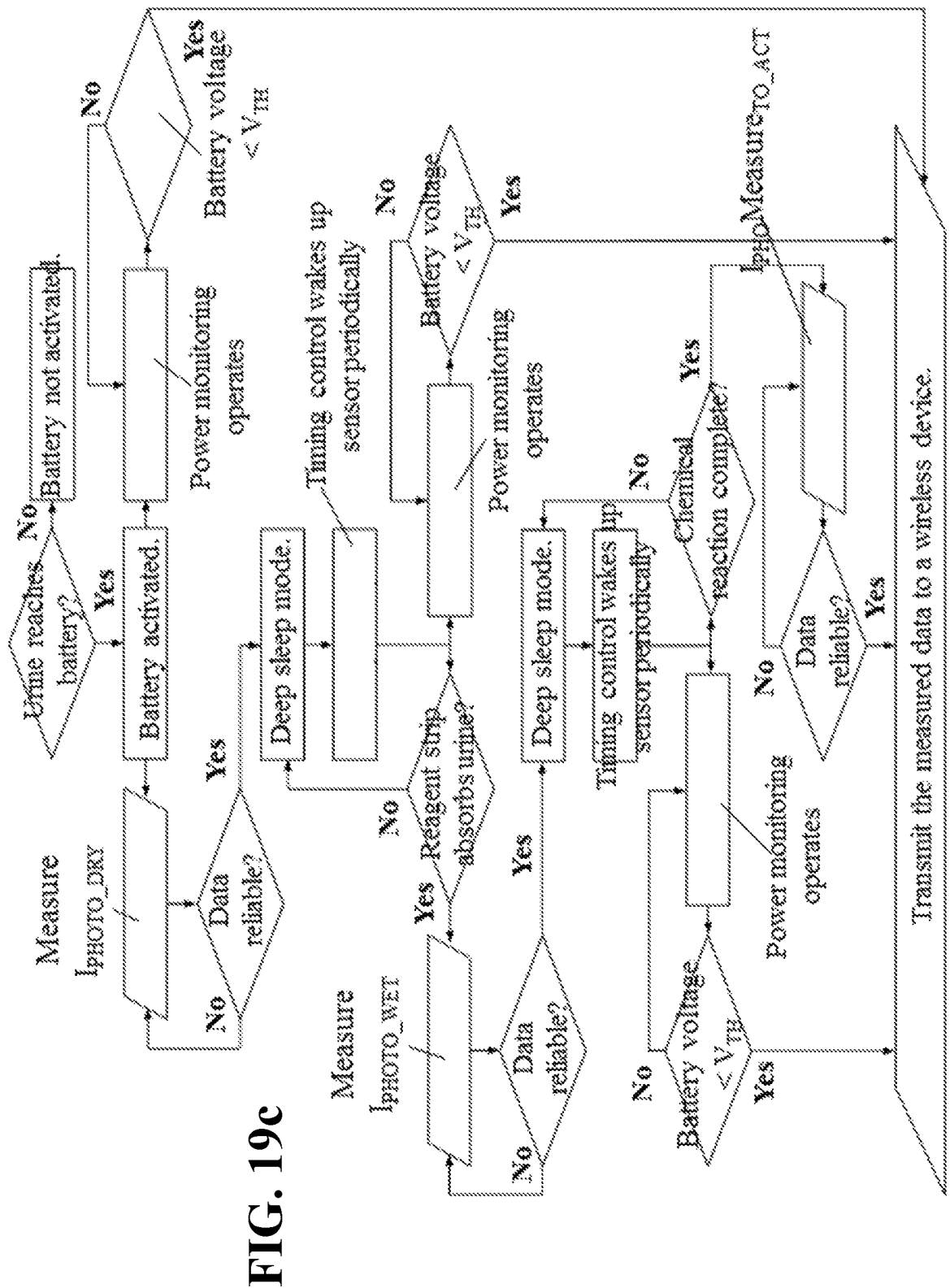

FIGS. 19*a*-19*c* show a system 100 configured for implementation of either a light or deep sleep mode via method 1600. Additionally, here, system 100 further comprises a power monitoring unit 1802 as shown in FIG. 19*a*. Referring to FIGS. 19*b* and 19*c*, the method 1600 comprises the following steps: liquid-activation of the battery 130 at step 1202; performance of steps 1204-1206 to measure $I_{PHOTO\_DRY}$ at step 1206 (performed over a flexible period of time); if the data is reliable, advancing to step 1602 (system 100 enters deep or light sleep mode); and, at step 1604, the timing control 1652 wakes up the sensing unit 102 periodically (intervals established per system 100 settings, but in at least one embodiment may comprise ~ sec. and which may be monitored by the clock source 1030 or otherwise) and cycles back through steps 1602 and 1604 until the sensing unit 102 detects liquids at step 1604.

Concurrent or following battery 130 activation at step 1202, the power monitoring unit 1802 operates to assess the voltage of the battery 130 at step 1901. For example, the unit 1802 may compare the measured battery voltage against an established threshold or conditional parameter. In at least one embodiment, the method 1600 advances to step 1210 if the power monitoring unit 1802 determines that the battery voltage is less than $V_{TH}$ at step 1901. As with method 1200, at step 1210, the collected data is transmitted to the computing unit 112 via the data transmission unit 110. In at least one embodiment, steps 1901 and 1210 (if necessary) may take about 1 second to perform.

Steps 1602 and 1604 repeat until the sensing unit 102 identifies that the reagent strip 124r has absorbed urine/liquid (i.e. is wet), at which point the method 1600 reperforms the measurement steps of method 1200 (steps 1204b-1206b) to measure $I_{PHOTO\_WET}$ at step 1206b (performed over a flexible period of time).

Additionally, at step 1604 (wake-up step), the method 1600 also advances to step 1902 where the power monitoring unit 1802 operates to assess the battery 130 voltage. Step 1902 can be performed concurrently with steps 1602 and 1604 or otherwise. As shown in FIG. 19b, a threshold or conditional parameter may be established for step 1902 with respect to evaluation of the battery 130—for example, if the battery voltage is less than $V_{TH}$, then step 1210 is performed and the collected data is transmitted to the computing unit 112 via the data transmission unit 110. In at least one embodiment, steps 1902 and 1210 (if necessary) may take about 1 second to perform.

Referring back to step 1206b, if the measured data is reliable, the method 1600 again advances to step 1602 (deep or light sleep mode, length of time set per system settings). If the measured data is not deemed reliable, the method 1600 reperforms steps 1204b-1206b until a reliable $I_{PHOTO\_WET}$ measurement is obtained.

At step 1602, the method 1600 cycles through steps 1602 and 1604 until the sensing unit 102 identifies that the chemical reaction on the reagent strip 124r is complete. Until this occurs, each time the method 1600 cycles to step 1604, the method 1600 also advances to step 1903. At step 1903, the power monitoring unit 1802 again operates to assess the battery 130 voltage. In at least one embodiment, such operation includes advancing to step 1210 (transmission of the measured data) if the battery voltage is less than $V_{TH}$.

When the reaction of the reagent strip 124r is complete, the method 1600 performs steps 1204c-1206c to obtain a reliable $I_{PHOTO\_ACT}$ measurement. If the measured $I_{PHOTO\_ACT}$ data is reliable, the method 1600 advances to step 1210 and the measured data is transmitted to the computing unit 112. If the measured data is not deemed reliable, the method 1600 reperforms steps 1204c-1206c until a reliable $I_{PHOTO\_ACT}$ measurement is obtained. Each of the steps of this method 1600 may be performed in about a second (or any other period of time desired), except that the measuring steps 1206, 1206b, 1206c may be performed over a flexible time period.

Figure 19D:
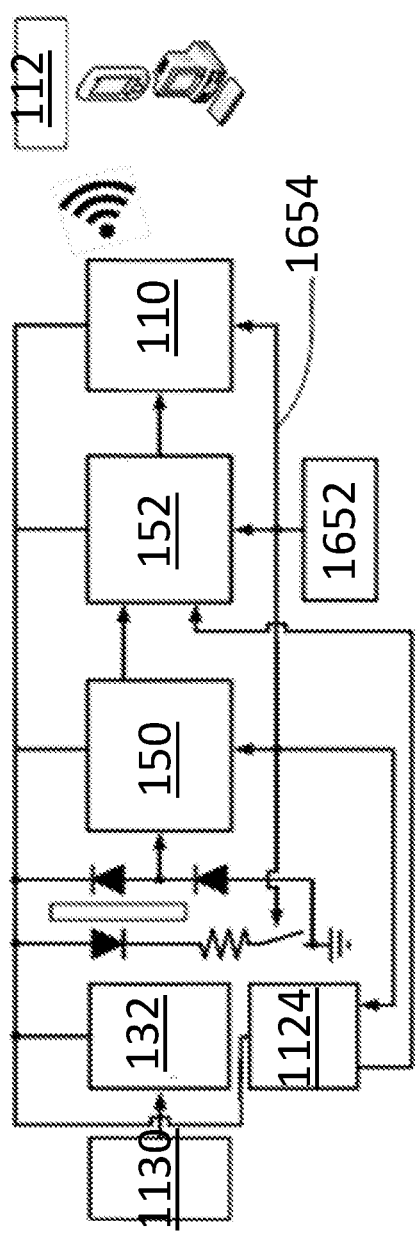
Figure 19E:
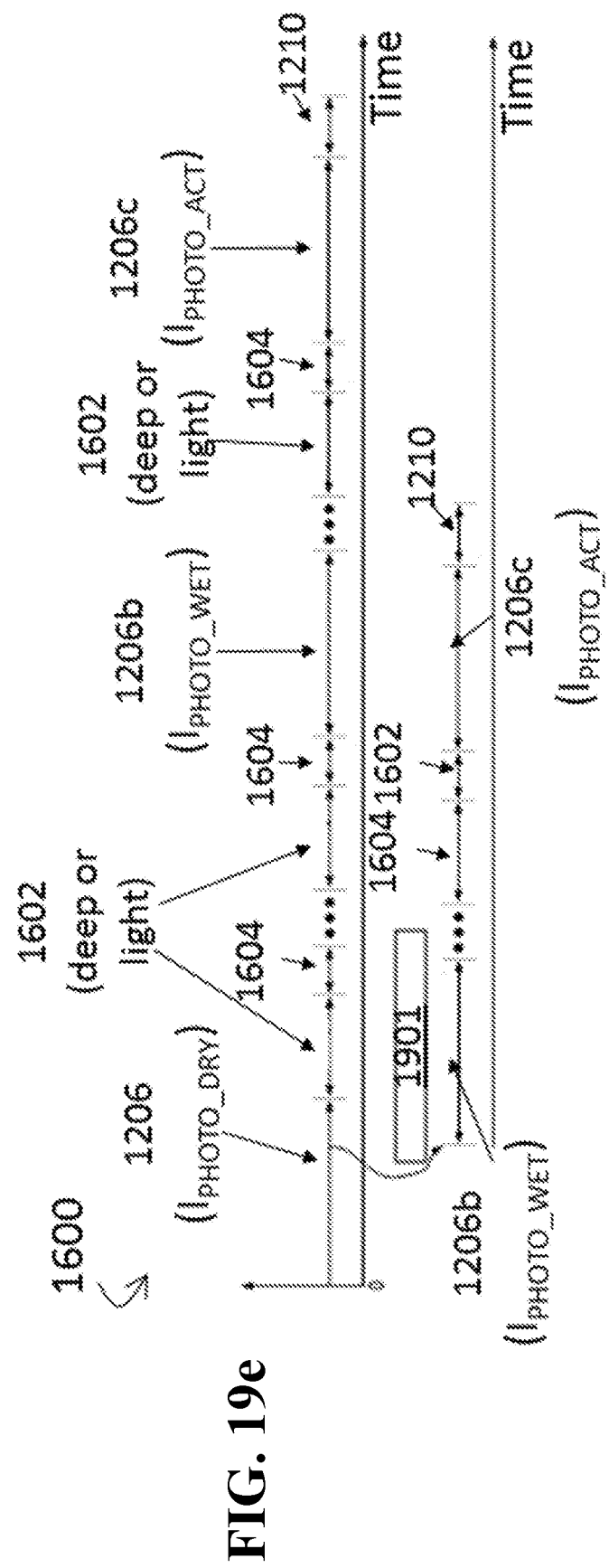
Figure 19F:
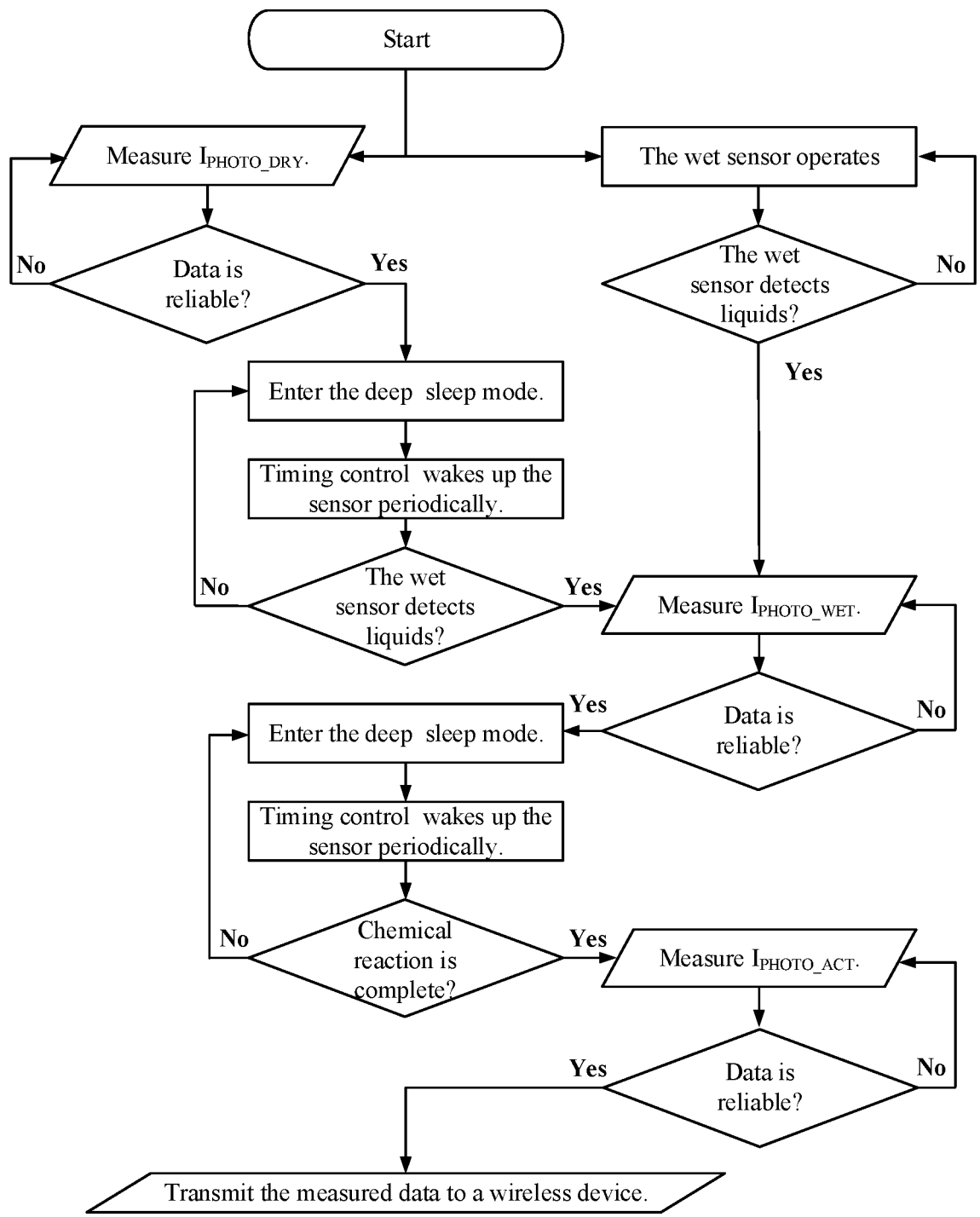

Referring to FIG. 19d, a system 100 comprising an external power source 1130 and a wet sensor 1124 is shown. FIGS. 19e and 19f show a timing sequence and a sequence of steps of method 1600 to implement either a light or deep sleep mode using the system 100 of FIG. 19d. Generally, the wet sensor 1124 activates when wetted (output becomes TRUE as opposed to FALSE), which functions to activate the sensor unit 102, while the power supply unit 104 (in this case, an external power supply 1130 such as a commercial external battery) powers the remainder of the system 100.

Here, the method 1600 starts with operation of the wet sensor 1124 at step 1912 (notably, operation of the wet sensor 1124 is not activated by the presence of liquid; the wet sensor 1124 is powered by the external power source 1130, for example). If, at step 1912, the wet sensor 1124 detects liquids (wet sensor output=TRUE), the method 1600 advances to step 1206b (by performing steps 1204b-1206b or otherwise) to measure $I_{PHOTO\_WET}$ (may be performed over a flexible period of time). However, if the wet sensor 1124 does not detect liquids at step 1912 (wet sensor output=FALSE), the method 1600 performs steps 1204-1206 to measure $I_{PHOTO\_DRY}$ at step 1206 (performed over a flexible period of time). If the data measured at step 1206 is reliable, the method 1600 advances to step 1602 and the detection system 100 enters deep or light sleep mode (as desired). Notably, the wet sensor 1124 is liquid-activated and, as such, activation of the wet sensor 1124 without the detection of liquids on the sensing strip 124 is indicative of liquid being present within the disposable device 60, but not yet traversing the transfer path 144 to the sensing unit 102. Accordingly, any sleep mode entered at step 1602 following activation of the wet sensor 1124 will likely comprise a short duration.

Alternatively, instead of step 1912 (for example, if the wet sensor 1124 is not activated by a liquid), the method 1600 may still proceed to step 1206b. Namely, if the detection system 100 initially collects a reliable $I_{PHOTO\_DRY}$ measurement at step 1206, the detection system 100 enters deep or light sleep mode at step 1602. At step 1604, the timing control 1652 periodically wakes up the sensing unit 102 and cycles back through steps 1602 and 1604 until the sensing unit 102 detects liquid in the reagent strip 124r (at step 1604). The length of sleep mode intervals (i.e. step 1602) may be established per system 100 settings, but in at least one embodiment comprise ~ min. Such intervals may be monitored by the clock source 1030 or otherwise.

Steps 1602 and 1604 repeat at predefined intervals until the wet sensor 1124 detects liquid within the system 100. At that point, $I_{PHOTO\_WET}$ measurements are obtained (by performing steps 1204b-1206b or otherwise). If the $I_{PHOTO\_WET}$ measurement is reliable, the detection system 100 again enters sleep mode at step 1602 and cycles through steps 1604 and 1602 as previously described. When the reagent reaction is complete, $I_{PHOTO\_ACT}$ measurements are obtained (by performing steps 1204c-1206c or otherwise) and, if reliable, the method transmits the measured data to the computing unit 112 via the data transmission unit 110 at step 1210.

Figure 19G:
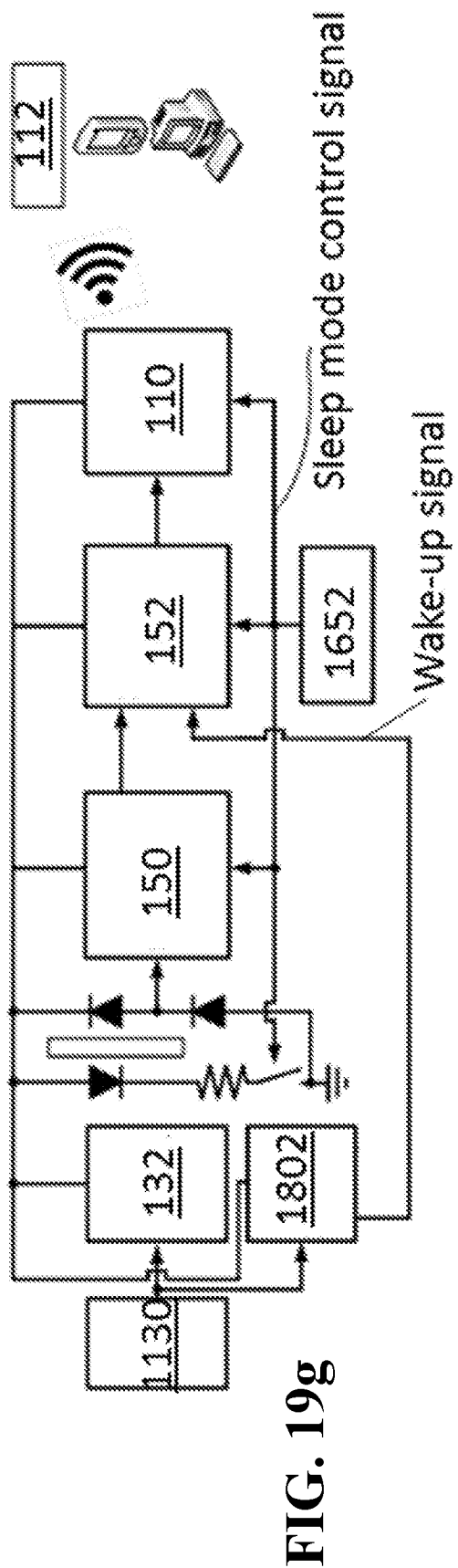
Figure 19H:
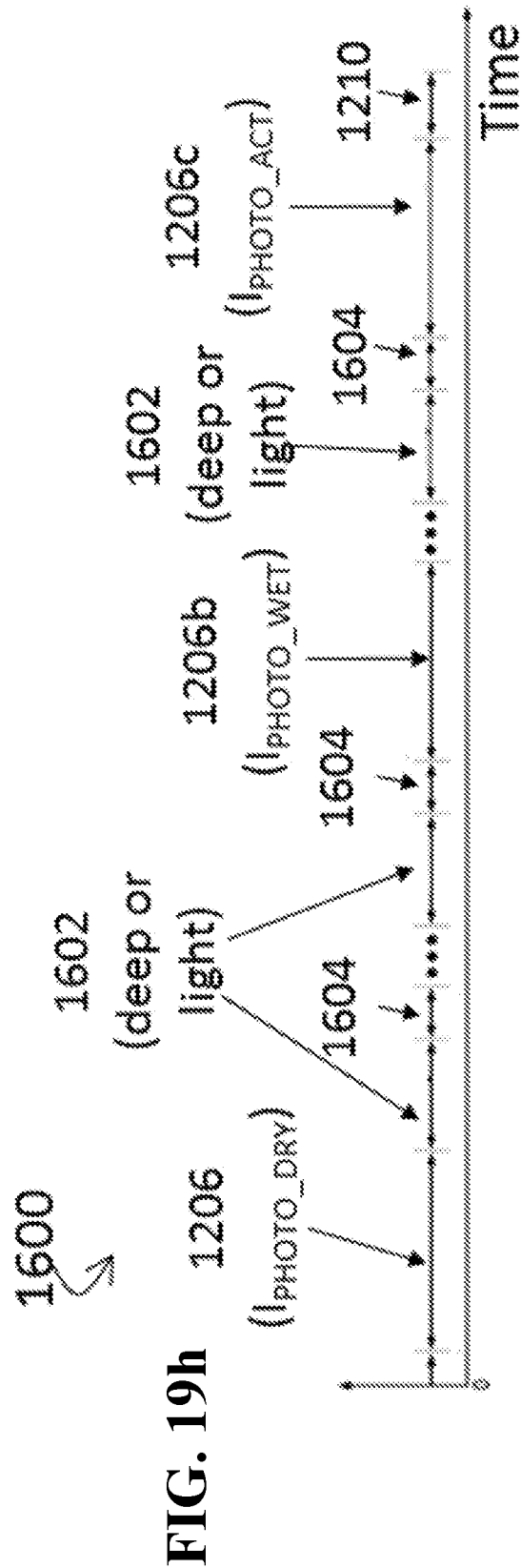
Figure 19I:
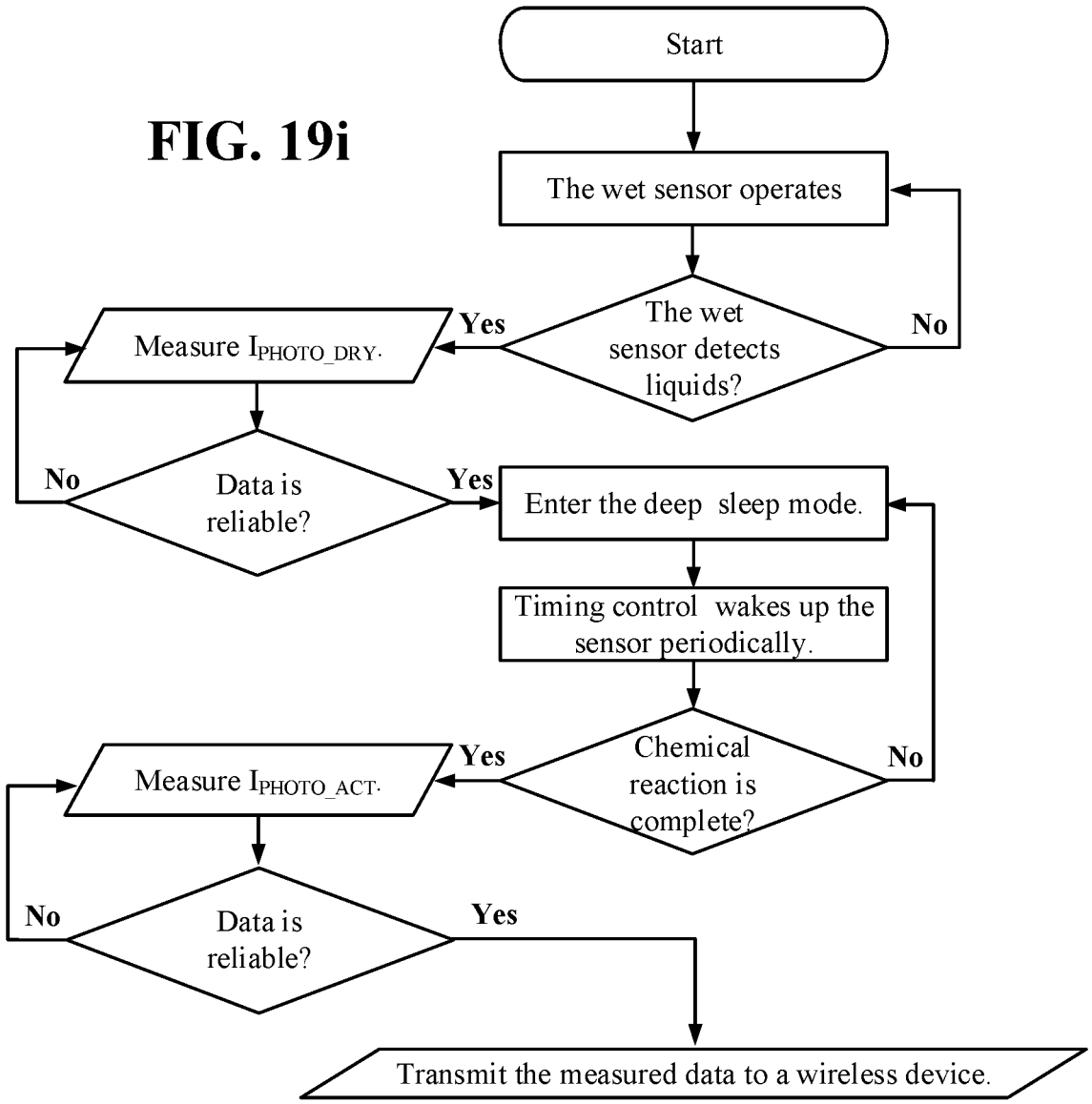

Now referring to FIGS. 19g-19i, a method 1600 that comprises wake-up functionality (a wake-up signal 1950) in addition to the sleep modes is shown in conjunction with the detection system 100 of the previous example (i.e comprising an external power supply 1310 and a wet sensor 1124). FIG. 19g illustrates a schematic of the wake-up signal 1950 communicatively connected to the wet sensor 1124 and the microprocessor 152 of the sensor signal processing unit 108.

Unlike the previously described embodiment, this version of method 1600 starts at step 1922 upon operation of the wet sensor 1124. If the wet sensor 1124 does not detect liquid present on the sensing strip 124 (output=FALSE), the wet sensor 1124 continues to operate until liquid is detected. Upon detection of liquid (output=TRUE), steps 1204-1206 are performed to measure $I_{PHOTO\_DRY}$ at step 1206 (performed over a flexible period of time). If the data measured at step 1206 is reliable, the method advances to step 1602 and the detection system 100 enters deep or light sleep mode. At step 1604, the timing control 1652 periodically wakes up the sensing unit 102 and cycles back through steps 1602 and 1604 until the sensing unit 102 detects liquids at step 1604. The length of the sleep mode intervals (i.e. step 1602) may be established per system 100 settings, but in at least one embodiment comprise ~ sec. Such intervals may be monitored by the clock source 1030 or otherwise.

Steps 1602 and 1604 repeat at predefined intervals until the wet sensor 1124 detects liquid within the system 100. At that point, $I_{PHOTO\_ACT}$ measurements are obtained (by performing steps 1204c-1206c or otherwise). If the $I_{PHOTO\_ACT}$ measurement is reliable, the detection system 100 transmits the measured data to the computing unit 112 via the data transmission unit 110 at step 1210.

Figure 19J:
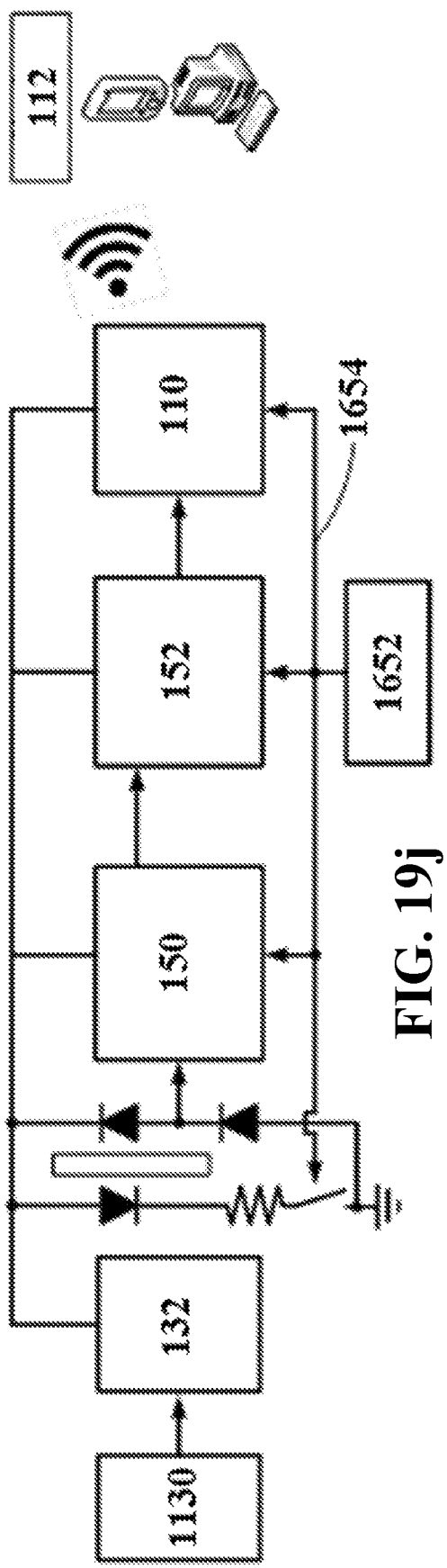
Figure 19K:
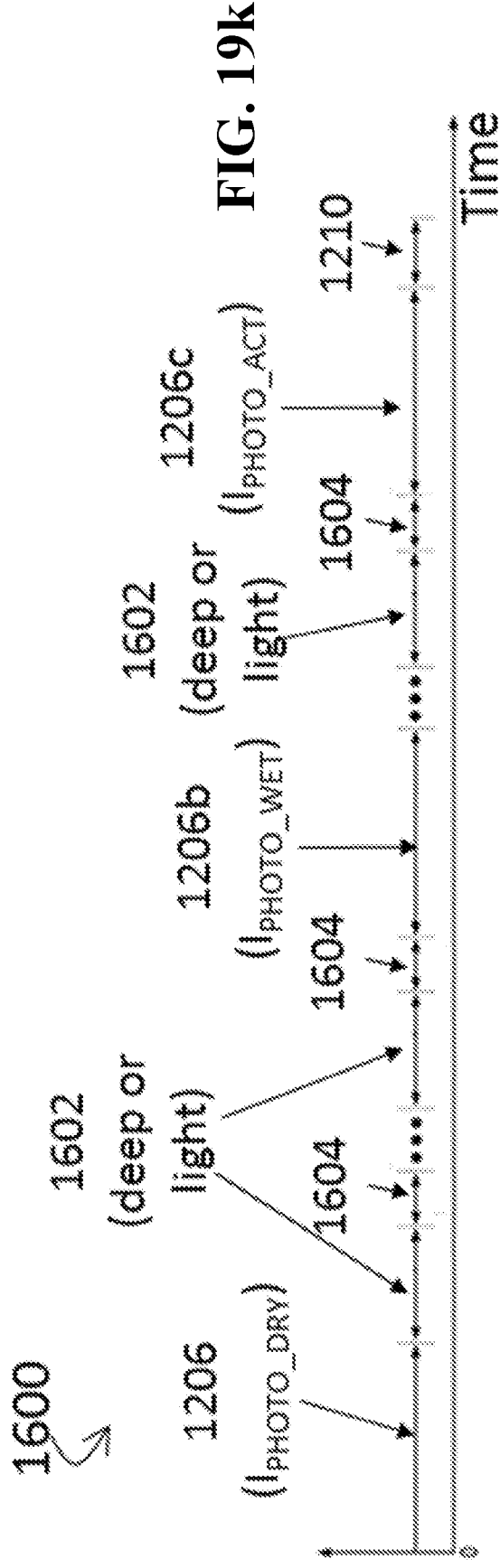
Figure 19L:
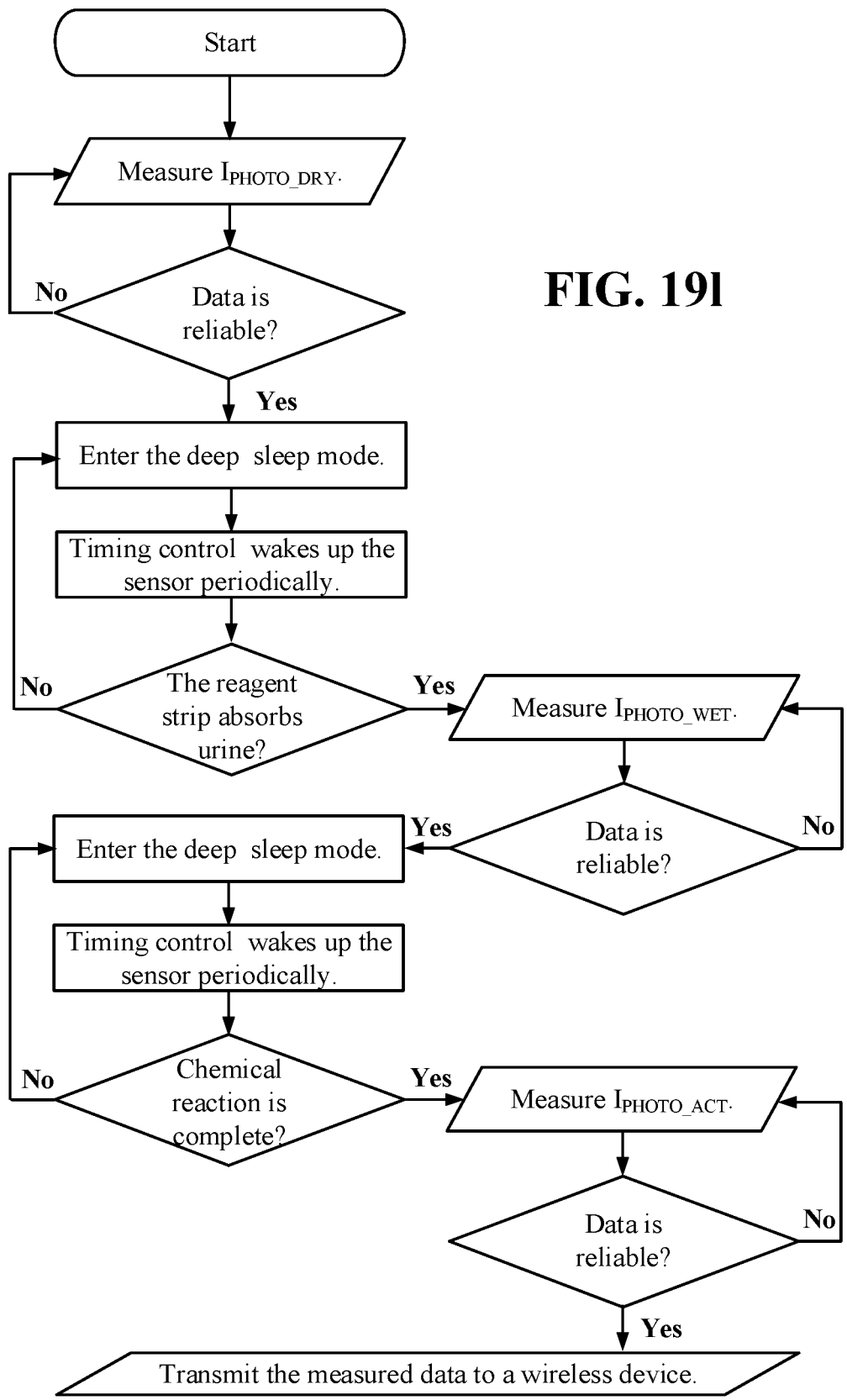

FIGS. 19j-19l illustrate yet another embodiment of the method 1600 for a sleep mode comprising periodic checks using a detection system 100 that has an external power source 1130. Method 1600 beings with the measurement of $I_{PHOTO\_DRY}$ at step 1206 (performed over a flexible period of time). If the data measured at step 1206 is reliable, the method advances to step 1602 and the detection system 100 enters deep or light sleep mode. At step 1604, the timing control 1652 periodically wakes up the sensing unit 102 and cycles back through steps 1602 and 1604 until the sensing unit 102 detects that the sensing strip 124 is absorbing urine or another liquid at step 1604. The length of the sleep mode intervals (i.e. step 1602) may be established per system 100 settings, but in at least one embodiment comprise ~ min. Such intervals may be monitored by the clock source 1030 or otherwise.

Steps 1602 and 1604 are repeated at predefined intervals until sensing unit 102 detects that the sensing strip 124 is absorbing urine or another liquid at step 1604. At that point, $I_{PHOTO\_WET}$ measurements are obtained (by performing steps 1204b-1206b or otherwise) and, if reliable, the system 100 again enters sleep mode at step 1602. Steps 602 and 1604 are repeated until the chemical reaction in the reagent unit 124r is complete and, thereafter, $I_{PHOTO\_ACT}$ measurements are obtained (by performing steps 1204C-1206c or otherwise). If the $I_{PHOTO\_ACT}$ measurement is reliable, the detection system 100 transmits the measured data to the computing unit 112 via the data transmission unit 110 at step 1210.

As described above, in addition to those embodiments of the system 100/disposable device 60 that comprise liquid-activated batteries 130, the sleep mode functionality may also be employed with embodiments of the system 100/disposable device 60 that comprise a power source unit 104 other than a liquid-activated, on-board battery 130 (for example, such as an external power supply 1130 as described in connection with FIG. 12e and other embodiments). Unlike on-board liquid-activated batteries, external power supplies 1130 alone are not configured to allow for the presence of liquid 402 to automatically trigger their operation (i.e. the generation/supply of power). In other words, operation of external power supplies 1130 are not dependent upon urination or another liquid source seeping into the disposable device 60/system 100. Instead, an external power supply 1130 of the detection system 100 may be configured for continuous and/or automatic, intermittent operation. Where an external power supply 1130 is continuously operated (i.e. a user switches external power supply 1130 on or plugs it in), the detection system 100/disposable device 60 can obtain a dry measurement (through performance of the method 1200 steps or otherwise) as soon as the external power supply 1130 is connected to the system 100 and/or operated to produce power. While this may be beneficial in terms of generating a large amount of data, continuous operation may not be desirable in terms of power consumption.

Accordingly, a detection system 100 comprising an external power supply 1130 may also comprise the timing control 1652 and the switch 1650 as was previously described in connection with systems 100 comprising liquid-activated batteries 130. In such scenarios, the switch 1650 and timing control 1652 are used to intermittently initiate operation of (or "switch on") the external power supply 1130 at predefined intervals to enable the periodic recording of measurements and, optionally, transmit data via the data transmission unit 110. In between the intervals of operation when power is not supplied and a sleep control signal 1654 is provided such that the switch 1650 is in the "off" position, the system 100 operates in sleep mode, thus, significantly decreasing or even eliminating its power usage. As in previously described embodiments, in sleep mode, one or more of the sensing unit 102, the sensor signal processing unit 108, and the data transmission unit 110 are disabled or run in a power-saving mode so as not to use energy (although operation of the timing control 1652 continues).

While operation of these embodiments does not allow for the automatic recording of measurements in direct response to a trigger event (such as urination), as the system 100 periodically operates over time, the detection system 100 will make wet and post-reaction wet measurements (assuming that urination and/or other liquid supplying events occur). Accordingly, measurements can be captured from the dry reagent strip 124r as well as the wet and/or reacted reagent strip 124r (i.e. where power is supplied after liquid/urine 402 has been absorbed through the system 100).

Additionally, as used herein, the differentiation between a light sleep mode and a deep sleep mode refers to the number of components (or sub-modules within a module or system component) that fall into sleep status during a sleep mode event. For example, in at least one embodiment, deep sleep mode may mean and include a sleep event where all of the sub-modules (components) of the system 100 fall into sleep status except for those essential to the ongoing functionality of the system 100 itself. Light sleep mode may mean a sleep mode event where many sub-blocks or system components are in sleep mode, but certain system components required for a desired (e.g., minimal) operation remain awake and functional. Typically, waking up from a deep sleep mode may take more time than waking the system 100 up from a light sleep mode event and when a module is in a deep sleep mode, it may consume less power than when in a light sleep mode.

Operation of the system 100 comprising an external power supply 1130 and a wet sensor 1124 can also be optimized to provide power-saving benefits (for wet sensor 1124 detail, refer to FIG. 12e). This is especially beneficial when used in conjunction with an external power supply 1130, as the wet sensor 1124 allows for operation of the external power supply 1130 in response to a trigger event (urination or the like).

Figure 20A:
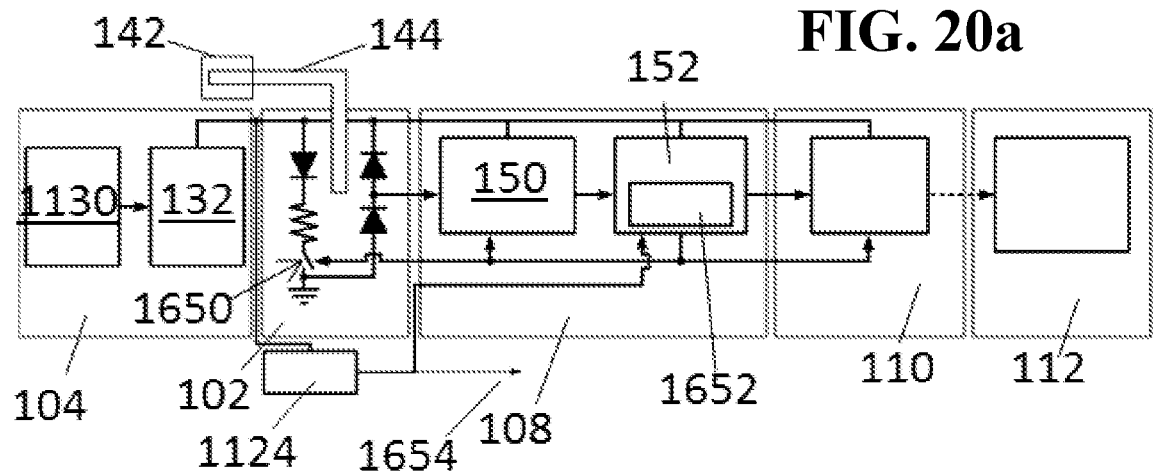
FIG. 20a shows a detection system according to an exemplary embodiment of the present disclosure comprising an external power supply, at least one wet sensor 114, a switch, and a timing control.
Figure 20B:
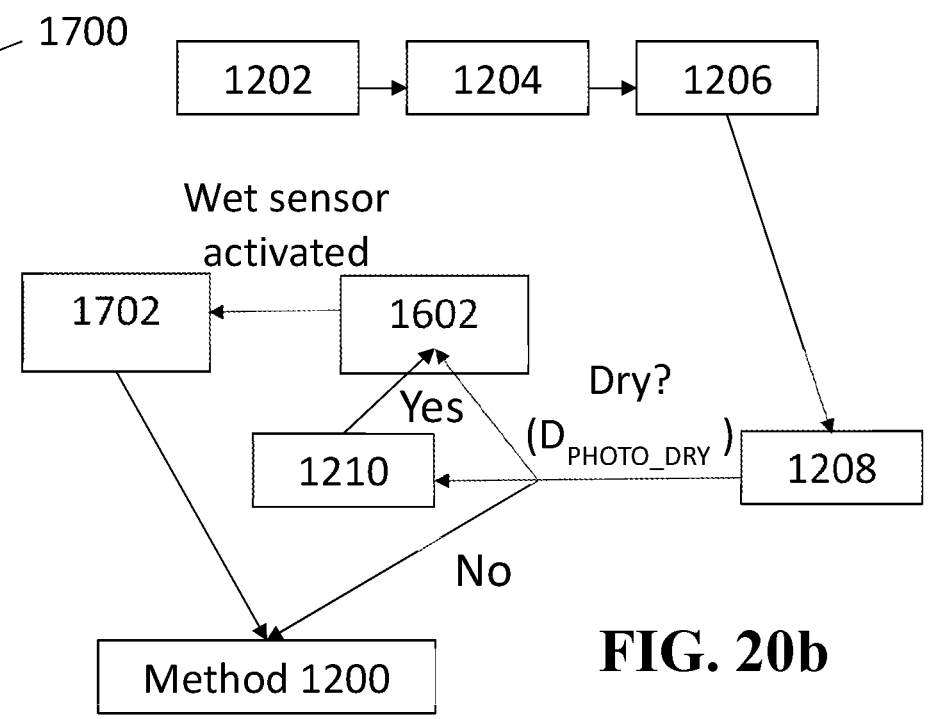

FIG. 20a shows an embodiment of system 100 comprising an external power supply 1130, at least one wet sensor 1124, a switch 1650, and a timing control 1652. Operation of the sleep mode functionality can be executed by performing method 1700 shown in the flow chart of FIG. 20b (like reference numerals with those of methods 1200 and 1600 referring to steps identical to the corresponding method steps of such methods unless modifications are expressly specified).

In method 1700, when power is supplied to the detection system 100 by forming a connection with the external power supply 1130 at step 1202, the system 100 takes a measurement when the sensing strip 124 is dry (the initial measurement) by performing steps 1204-1208. (Additionally, method 1700 may also include step 1210 to store and/or transmit the output signal as desired.) After the dry measurement is obtained, the method 1700 advances to step 1602 and enters sleep mode by emitting sleep control signal 1652 to turn off the switch 1650. This reduces the functionality of the system 100 and reduces or ceases its power consumption.

When and if the wet sensor 1124 output indicates the arrival of a liquid 402 within the disposable device 60/system 100, the method 1700 advances to step 1702 where the sensing unit 102 periodically wakes up to make measurements—specifically, at least a wet (pre-reaction) measurement and a post-reaction measurement. For optimal calibration, it is beneficial for the detection system to measure both $D_{PHOTO\_DRY}$ and $D_{PHOTO\_WET}$, or at least one of the foregoing. The measured data is then saved and/or transmitted at step 1210.

Experiments

To show enablement, various embodiments of the detection system 100 were implemented in connection with the methods hereof and measurement results were assessed. In one embodiment, the measurement setup used for the sensing unit (102) was as follows: colorimetric nitrite sensor (124), 2.5 cm×3.5 cm, 3 g; DC-DC boost converter (132) and sensor interface (150), 2.7 cm×3.6 cm, 6 g; urine-activated batteries 130, 15 cm×3.5 cm, 6 g; BLE module (108), 2.286 cm×2.8956 cm, 5 g; software (80) of computing unit 112, mobile app displaying nitrite concentration in real time. The boost DC-DC converter 132 and the PWM sensor interface 150 were mounted on a custom printed circuit board (PCB).

During measurements, the colorimetric nitrite sensor (124) was placed in a box to ensure that the active photodetector (122a) only responded to the LED light from the LED light source (120), but not to the ambient light. An LED light source (120) with the peak emission wavelength of 572 nm was chosen because of its high sensitivity to pink color. Two photodiodes (photodetectors 122) with the peak sensitivity wavelength of 540 nm were used and the LED bias current was set to 0.5 mA while the PWM sensor interface draws 0.008 mA from the regulated 2V supply. The microcontroller in the BLE module (data transmission unit 110; RFD22102 from RFDuino) provided the CLK signal and converted the pulse width output of the PWM sensor interface (150) into digital data using the built-in counter that was transmitted to a paired mobile device (computing unit 112; an Android tablet). The BLE module (108) drew 4 mA in transmission mode.

Figure 21:
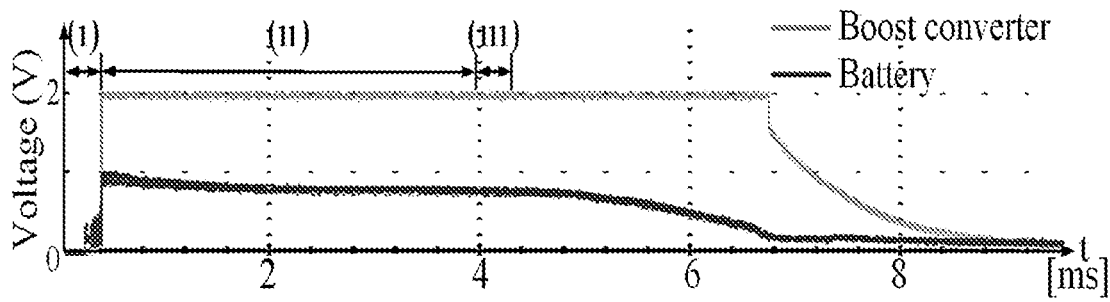
FIG. 21 is a graphical representation of measured battery voltage and boost converter voltage using the detection system according to an exemplary embodiment of the present disclosure, with (i) initial urine exposure and battery activation; (ii) DC-DC boost convert start and sensor reading; and (iii) BLE transmission.
Figure 22:
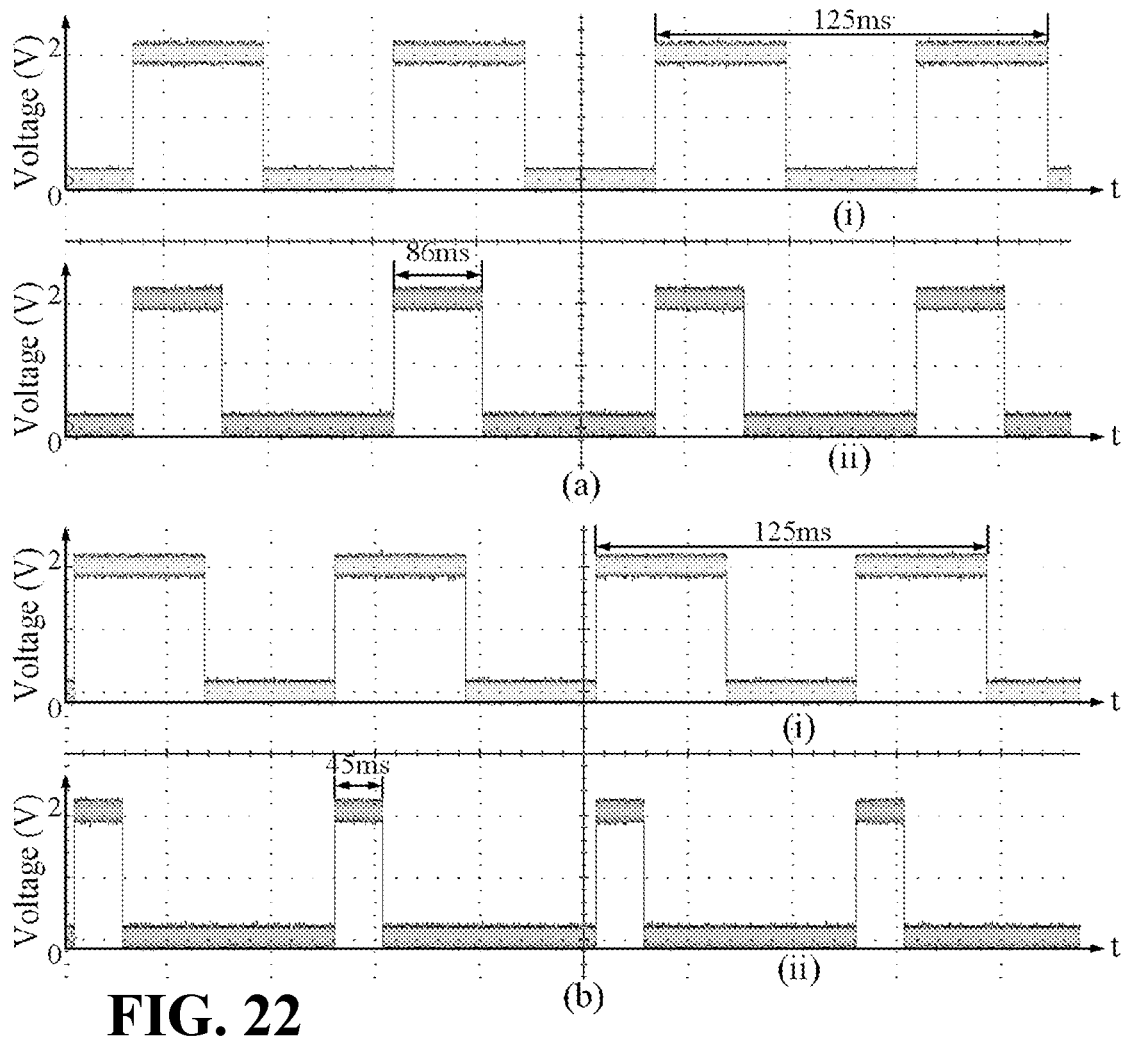
FIG. 22 is a graphical representation of measured PWM signals, (a) pulse width for a dry reagent strip: (i) clock signal, and (ii) Output $V_{PWM}$ signal; and (b) pulse width for the wet reagent strip: (i) clock signal, and (ii) (ii) Output $V_{PWM}$ signal.
Figure 23:
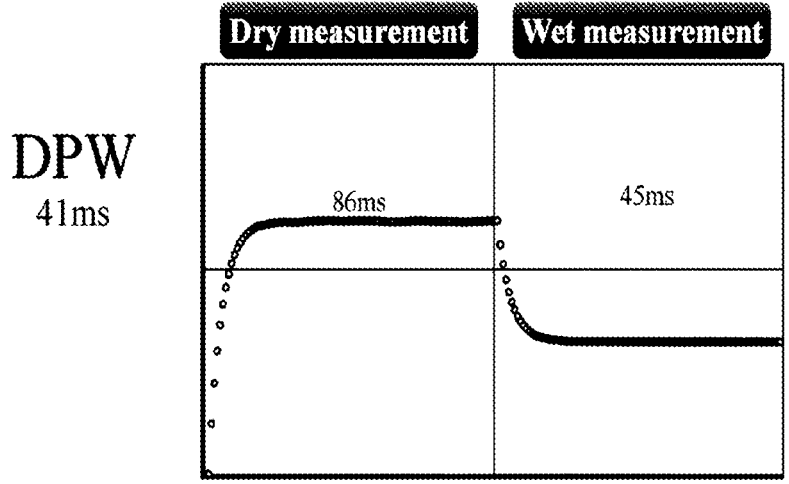
FIG. 23 shows data resulting from operation of a detection system according to an exemplary embodiment of the present disclosure displayed on a mobile device.

Synthetic urine samples with nitrite concentrations of 0 mg/L, 4 mg/L, 6 mg/L, 8 mg/L, and 10 mg/L were used for the measurements. To perform the tests, urine samples (402) were dropped onto the sensors (124) and the urine-activated batteries at the same time. FIG. 21 shows the voltage variation of the urine-activated batteries (130) and the regulated voltage of the boost DC-DC converter (132). The batteries (130) were activated in 10 seconds after initial urine exposure and the boost DC-DC converter (132) started operation when the voltage of batteries (130) reached 0.5V, at which time the colorimetric sensor (124) starts reading. The PWM signals for the dry reagent strip and for the wet reagent strip were measured and are shown in FIG. 22. The BLE module (108) digitized the PWM signals and transmitted them. FIG. 23 shows $T_{PW1}$, $T_{PW2}$, and the differential pulse width displayed on the mobile device (112) at real-time.

Figure 24A:
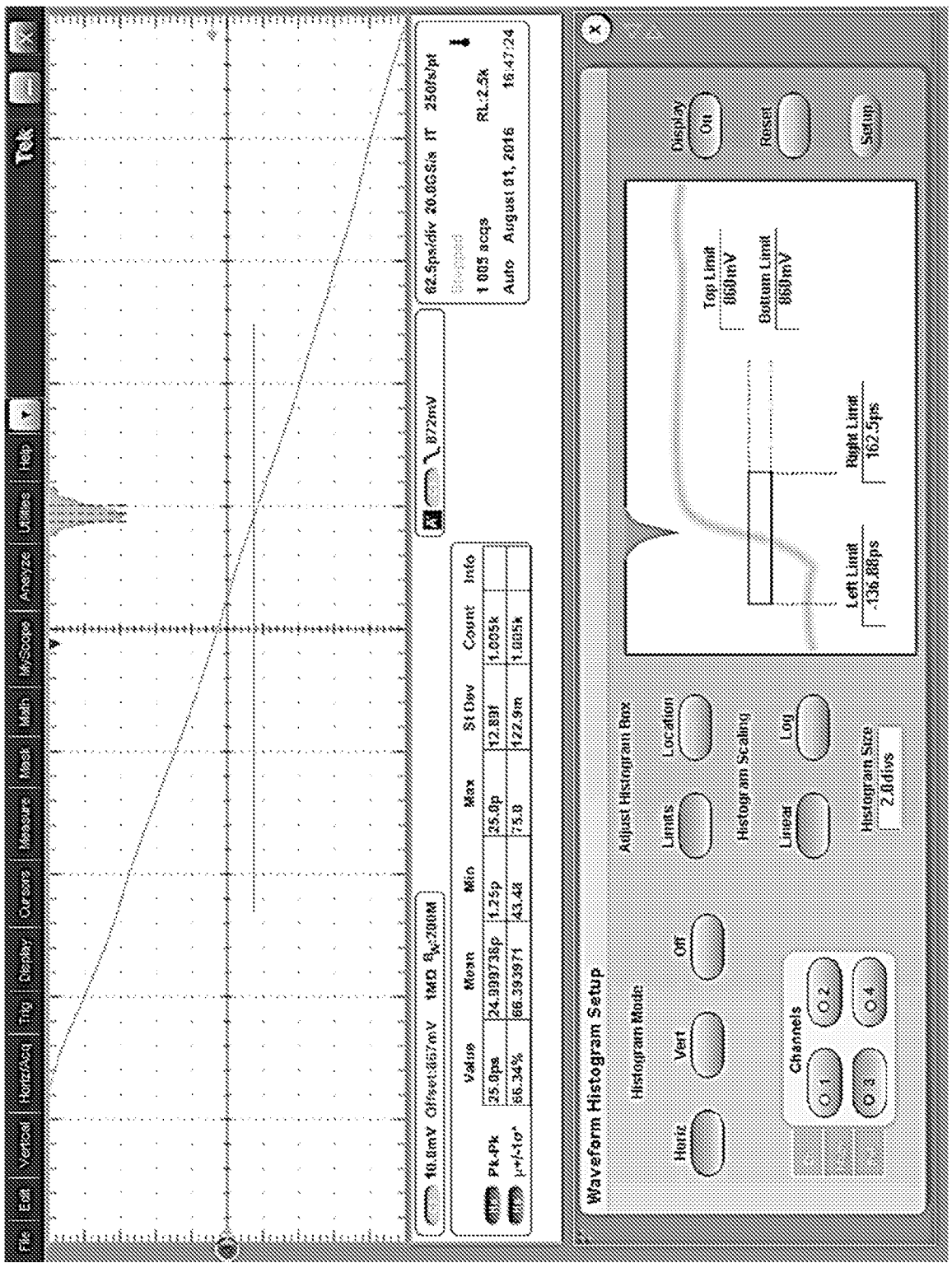
FIGS. 24a and 24b show jitter measurements of the PWM output signal falling edge (FIG. 24a) and RMS jitter on rising and falling edges of the PWM output signal versus nitrite concentration (FIG. 24b)
Figure 24B:
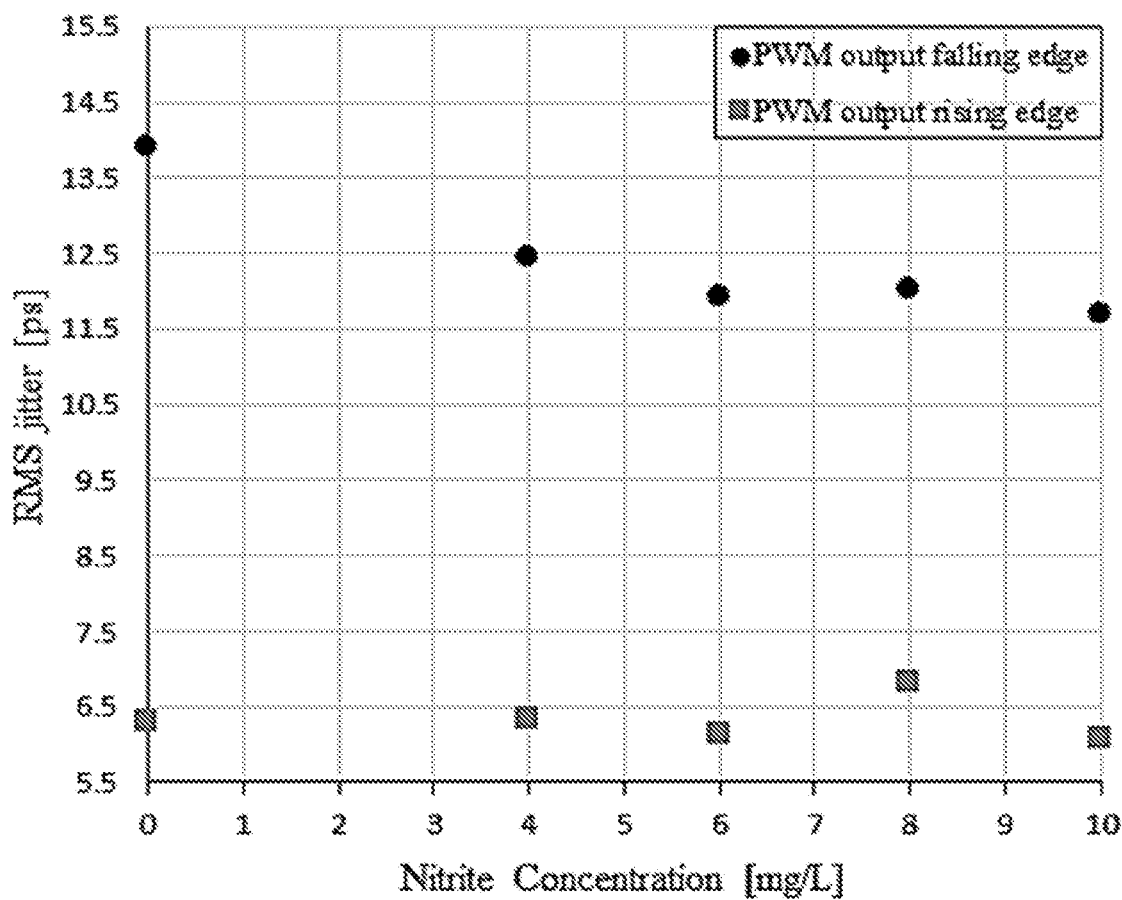

The jitter on the rising and falling edges of PWM signal were measured using a high-speed oscilloscope as shown in FIG. 24a. FIG. 24b shows the measured jitter on the rising and falling edges of PWM signal in the presence of different nitrite concentrations. As described by Equations (12)-(18), the falling edge jitter is bigger than the rising edge jitter and the falling edge jitter is inversely proportional to the nitrite concentrations because the photodiode (122) currents decreases while the rising edge jitter remains constant.

Figure 25A:
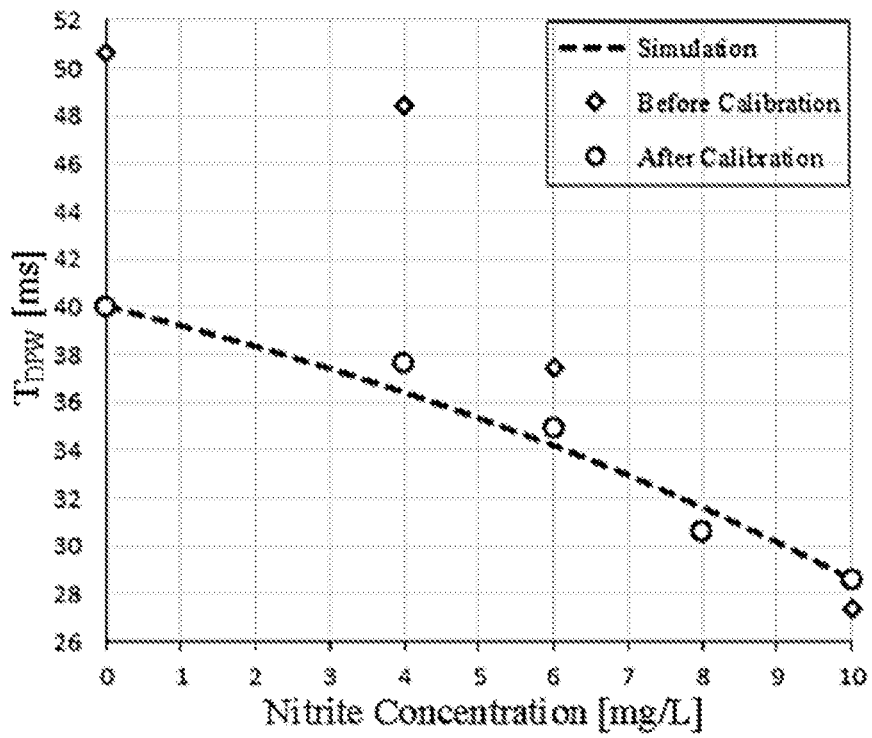
FIGS. 25a and 25b show measured differential pulse width versus nitrite concentrations (FIG. 25a) and a conventional dipstick color chart for comparison purposes (FIG. 25b)
Figure 25B:
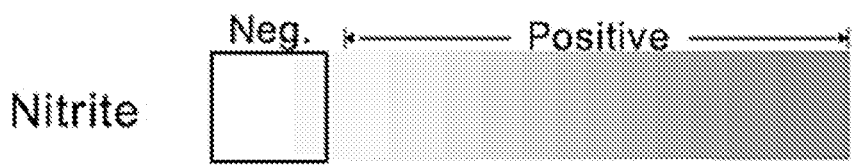

FIG. 25a illustrates the differential pulse width versus nitrite concentrations curves for an ideal case simulation and measurements before and after the calibration. For the ideal case simulation, SPICE simulations were used. Inverters (902) and NAND gates (904) of the sensor interface (150) were modeled based on IBIS model provided by TI. The voltage dependent parasitic capacitance was implemented with Verilog-A. The active photodiode (122a) was replaced with a current source, which current was changed according to previously performed studies and a voltage dependent parasitic capacitance. As a simplification, the dark current of the active photodiode (122a) was assumed to be canceled out by the reference photodiode (122r) that was replaced with a voltage dependent parasitic capacitance. For the measured differential pulse width $T_{DPW}$ before the calibration, the maximum error from the ideal case simulation reached up to 33%, while the $T_{DPW}$ after the calibration showed a maximum error of 3.5%, which corresponds to almost 10 folds of improvement. The sensor module (102) achieved a sensitivity of 1.35 ms/(mg/L) and a detection limit of 4 mg/L for nitrite. Because nitrite is never found naturally in urine, and many species of gram-negative bacteria convert nitrate to nitrite, the $T_{DPW}$ of urine from a person without a UTI will show 40 ms. Accordingly, the $T_{DPW}$ of the urine of a person with UTI will be smaller than 40 ms, with the difference increasing with an increasing amount of nitrite in the urine. FIG. 25b shows a reference color chart of typical urine dipsticks designed for nitrite detection. To the untrained eyes, a quantitative analysis on nitrite concentration, beyond the decision on positive or negative, is not feasible for dipsticks. This additional quantitative information can be beneficial for a health information technology. The comparison demonstrates the effectiveness of the proposed autonomous sensing utilizing the developed sensor module (102).

Figure 26:
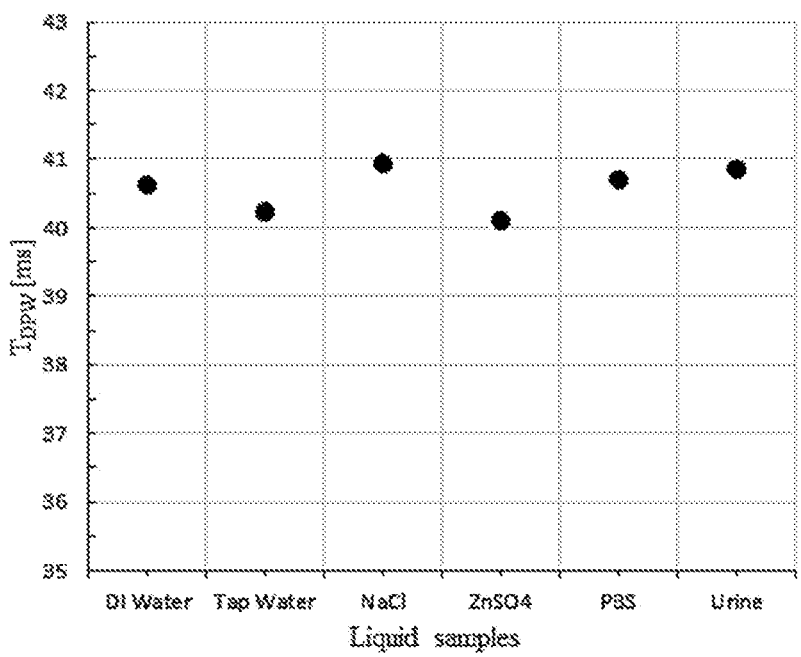
FIG. 26 shows a plot of measured differential pulse width liquid samples.

FIG. 26 presents the measured differential pulse width with liquid samples, showing that the differential pulse width changes by 2.03%. Although the urine composition varies among patients, the sensor module (102) should correctly detect only nitrite for UTI. To verify the sensor module specificity to nitrite, different types of solutions such as deionized (DI) water, tap water, NaCl of 500 mg/L, $ZnSO_4$ of 500 mg/L, phosphate-buffered saline (PBS), and fresh urine sample were used. These experimental results prove that the sensor module (102) can detect nitrite reliably regardless of liquid samples.

While various embodiments of compositions, systems, and methods hereof have been described in considerable detail, the embodiments are merely offered by way of non-limiting examples. Many variations and modifications of the embodiments described herein will be apparent to one of ordinary skill in the art in light of the disclosure. It will therefore be understood by those skilled in the art that various changes and modifications may be made, and equivalents may be substituted for elements thereof, without departing from the scope of the disclosure. Indeed, this disclosure is not intended to be exhaustive or to limiting. The scope of the disclosure is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure. It is therefore intended that this description and the appended claims will encompass, all modifications and changes apparent to those of ordinary skill in the art based on this disclosure.

While embodiments of the devices, kits, systems and methods herein have been described in considerable detail, such embodiments are merely offered by way of non-limiting examples. It will be understood that various changes and modifications may be made, and equivalents substituted for elements thereof, without departing from the scope of the disclosure. This disclosure is not intended to be exhaustive or to limit its scope. Further, in describing representative embodiments, the disclosure may have presented a method and/or process as a particular sequence of steps; however, to the extent that the method/process does not rely on the particular order of steps set forth herein, it should not be limited to the particular sequence of steps described as other sequences may be possible. Therefore, the particular order of the steps disclosed herein should not be construed as limiting. In addition, disclosure directed to a method and/or process should not be limited to the performance of their steps in the order written. Such sequences may be varied and still remain within the scope of the present disclosure.

The invention claimed is:

1. A detection system comprising:
   a first disposable device for embedding or placement within a diaper, the first disposable device comprising:
      a sensing unit integrated onto a flexible substrate, the sensing unit comprising:
         at least one light source,
         a sensing strip comprising at least one reagent strip containing one or more colorimetric reagents for reacting with a targeted compound, and
         at least one sensor for measuring color density data from the at least one reagent strip and generating photocurrent data related thereto,
         wherein the color density data correlates with a concentration of the targeted compound detected on the sensing strip,
      a power source unit in electrical communication with the sensing unit, the power source unit comprising at least one battery operable to power at least the sensing unit, and
      a transport path unit defining at least one open area for receiving liquid therethrough and comprising a transport path comprising a channel extending between the at least one open area and the sensing unit, between the at least one open area and the power source unit, or between the at least one open area, the sensing unit, and the power source unit;
   a second device configured for wired communication with the first disposable device and comprising:
      a signal processing unit comprising a sensor interface circuit in operative communication with a microprocessor and configured to convert the photocurrent data received from the sensing unit into one or more output signals, and
      a data transmission unit in operable communication with the signal processing unit; and
   a computer readable program code executable by a computer to analyze the one or more output signals received from the data transmission unit and calculate the concentration of the targeted compound in liquid received through the transport path based on the one or more output signals.

2. The detection system of claim 1, wherein:
   the transport path comprises a first transport path and a second transport path, the first transport path comprising a first channel extending for a first length between the at least one open area and the at least one battery and the second transport path comprising a second channel extending for a second length extending between the at least one open area and the sensing unit; and
   parameters of the transport path unit are selected such that liquid received through the at least one open area and absorbed into the first transport path travels along the first length and reaches the at least one battery of the power source prior to when such received liquid reaches the reagent strip of the sensing unit via the second transport path such that the at least one battery of the power source unit activates the sensing unit and the at least one sensor measures color density data from the at least one reagent strip both before and after the liquid reaches a portion of the at least one reagent strip adjacent to the at least one sensor.

3. The detection system of claim 1, wherein:
   the transport path unit further comprises a pad positioned between the at least one open area and the transport path, the pad comprising an absorbent material; and
   the sensing strip is sandwiched between the at least one light source and at least one of the at least one sensor such that the at least one light source is aligned with at least one sensor, the at least one reagent strip, or both.

4. The detection system of claim 1, wherein:
   at least one of the at least one sensors is configured to measure color density data from the at least one reagent strip when the at least one reagent strip is dry, when the at least one reagent strip that is wet from absorbing a liquid, and after the one or more reagents of the at least one reagent strip that has reacted with the liquid; and
   the concentration of the targeted compound is calculated using the difference between a first output signal corresponding with photocurrent data from the at least one reagent strip that is wet and a second output signal corresponding with photocurrent data from the at least one reagent strip that has reacted with the liquid.

5. The detection system of claim 1, wherein:
   the at least one reagent strip of the sensing strip comprises a first reagent strip containing one or more colorimetric reagents for reacting with a first targeted compound and a second reagent strip containing one or more colorimetric reagents for reacting with a second targeted compound, the first and second targeted compounds are not the same compound; and the first and second targeted compounds are each selected from a group consisting of nitrite, nitrate, protein, albumin, red blood cells, hemoglobin, white blood cells, and leucocyte esterase.

6. The detection system of claim 1, wherein the power source unit comprises at least one liquid-activated battery such that when liquid is received within the at least one liquid-activated battery, the liquid-activated battery generates power and the sensing unit measures color density data from the at least one reagent strip.

7. The detection system of claim 1, wherein the at least one light source of the sensing unit comprises at least one light emitting diode or at least one laser.

8. The detection system of claim 1, wherein the at least one sensor comprises an active photodetector.

9. The detection system of claim 1, wherein the liquid comprises urine or soil, the targeted compound comprises a nitrite or a nitrate, and the concentration of the targeted compound calculated is used to detect a urinary tract infection.

10. The detection system of claim 1, wherein the computer readable program code is further executable to issue a notification if the concentration of the targeted compound is outside of a defined parameter.

11. A detection system comprising:
a first disposable device for embedding or placement within a diaper, the first disposable device comprising:
a sensing unit integrated onto a flexible substrate, the sensing unit comprising:
at least one light source,
a sensing strip comprising at least one reagent strip containing one or more colorimetric reagents for reacting with a targeted compound and an open area where the sensing strip may receive liquid, and
at least one sensor for measuring color density data from the at least one reagent strip and generating photocurrent data related thereto,
wherein the color density data correlates with a concentration of the targeted compound detected on the sensing strip; and
a transport path unit defining at least one open area for receiving liquid therethrough and comprising at least one transport path comprising a microfluidic channel extending at least between the at least one open area and the sensing unit;
a second device for removable attachment to a diaper, the second device configured for wired communication with the first disposable device and comprising:
a signal processing unit comprising a sensor interface circuit in operative communication with a microprocessor and configured to convert photocurrent data received from the sensing unit into one or more output signals, and
a data transmission unit in operable communication with the signal processing unit;
a power source unit in electrical communication with the first and second devices, the power source unit comprising a power source for providing power to the sensing unit and a power stage for regulating voltage produced by the power source;
a power control unit communicatively coupled with one or more of the sensing unit, the signal processing unit, and the data transmission unit, the power control unit configured to initiate one or more sleep mode events, each sleep mode event comprising a reduction or cessation of power to the units with which the power control unit is communicatively coupled to disable functionality thereof; and
a computer readable program code executable by a computer to analyze the one or more output signals received from the data transmission unit and calculate a concentration of the targeted compound in liquid received through the at least one transport path based on the one or more output signals;
wherein when the sensing unit receives power from the power source, the at least one sensor measures photocurrent data from the at least one reagent strip.

12. The detection system of claim 11, wherein the power control unit is further configured to conclude a sleep mode event by restoring power to the one or more units with which the power control unit is communicatively coupled, thereby activating the functionality thereof.

13. The detection system of claim 12, where the sensing unit measures color density data from the at least one reagent strip when the at least one reagent strip is dry, the power control unit is configured to initiate and cycle through one or more sleep mode events, the conclusion of each sleep mode event allowing for at least measurement of color density data by the at least one sensor and/or activation of the data transmission unit.

14. The detection system of claim 11, further comprising a computing unit comprising a processor operable to execute the computer readable program code, wherein the computer readable program code is accessible by or stored on the computing unit.

15. The detection system of claim 14, wherein the computing unit comprises a mobile device.

16. The detection system of claim 15, wherein at least one of the at least one sensor is configured to measure color density data from the at least one reagent strip when the at least one reagent strip is dry, when the at least one reagent strip is wet from absorbing a liquid, and after the one or more reagents of the at least one reagent strip have reacted with the liquid.

17. The detection system of claim 16, wherein the concentration of the targeted compound is calculated using the difference between a first output signal corresponding with photocurrent data from the at least one reagent strip that is wet and a second output signal corresponding with photocurrent data from the at least one reagent strip that has reacted with the liquid.

18. A kit for the autonomous detection of a health condition within a patient, the kit comprising:
one or more first disposable devices for embedding or placement within a diaper, each of the first disposable devices comprising:
a sensing unit integrated onto a flexible substrate, the sensing unit comprising:
at least one light source,
a sensing strip comprising at least one reagent strip containing one or more colorimetric reagents for reacting with a targeted compound, and
at least one sensor for measuring color density data from the at least one reagent strip and generating photocurrent data related thereto,
wherein the color density data correlates with a concentration of a targeted compound detected on the sensing strip,
wherein the sensing strip is positioned between the at least one light source and at least one of the sensors such that the at least one light source is aligned with at least one sensor, the at least one reagent strip, or both, and the at least one light source, the at least one sensor, and at least a portion of the sensing strip are all sandwiched between the flexible substrate when the flexible substrate is folded upon itself, a power source unit in electrical communication with the sensing unit, the power source unit comprising at least one battery operable to power at least the sensing unit, and a transport path unit defining at least one open area for receiving liquid therethrough and comprising at least one transport path comprising a channel extending between the at least one open area and the sensing unit, between the at least one open area and the power source unit, or between the at least one open area, the sensing unit, and the power source unit; and a second device comprising:

a signal processing unit comprising a sensor interface circuit in operative communication with a microprocessor and configured to convert photocurrent data received from the sensing unit into one or more output signals, and a data transmission unit in operable communication with the signal processing unit.

19. The kit of claim 18, further comprising one or more diapers.

20. The kit of claim 18, wherein the second device is configured to be communicatively coupled with a computing unit comprising a computer readable program code executable to analyze the one or more output signals received from the data transmission unit and calculate a concentration of the targeted compound in liquid received through the transport path based on the one or more output signals, the computer readable program code stored on a storage device, the computer readable program code for use with a mobile device.

* * * * *